(12) United States Patent
Liao et al.

(10) Patent No.: US 7,521,192 B2
(45) Date of Patent: Apr. 21, 2009

(54) EDG: MODULATORS OF LYMPHOCYTE ACTIVATION AND MIGRATION

(75) Inventors: X. Charlene Liao, Palo Alto, CA (US); Esteban Masuda, Menlo Park, CA (US); Peter Chu, San Francisco, CA (US); Jorge Pardo, San Francisco, CA (US); Congfen Li, Davis, CA (US); Haoran Zhao, Foster City, CA (US); Ying-Ping Jiang, Lafayette, CA (US); Collin Spencer, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/971,228

(22) Filed: Oct. 3, 2001

(65) Prior Publication Data

US 2002/0155512 A1 Oct. 24, 2002

Related U.S. Application Data

(60) Provisional application No. 60/284,763, filed on Apr. 18, 2001.

(51) Int. Cl.
*G01N 33/53* (2006.01)
(52) U.S. Cl. .................. 435/7.1; 435/7.21; 435/7.24
(58) Field of Classification Search .................. 435/7.1, 435/7.24; 424/9.1
See application file for complete search history.

(56) References Cited

U.S. PATENT DOCUMENTS

| 5,508,384 | A | | 4/1996 | Murphy et al. |
| 5,580,720 | A | * | 12/1996 | Jonak et al. .................. 435/5 |
| 5,585,476 | A | | 12/1996 | MacLennan |
| 6,037,136 | A | | 3/2000 | Beach et al. |
| 6,207,393 | B1 | | 3/2001 | Shaw et al. |
| 6,656,695 | B2 | * | 12/2003 | Berg et al. .................. 435/7.21 |

FOREIGN PATENT DOCUMENTS

| WO | WO 91/15583 A1 | 10/1991 |
| WO | WO 94/05695 A1 | 3/1994 |
| WO | WO 99/19513 A2 | 4/1999 |
| WO | WO 99/19513 A3 | 4/1999 |
| WO | WO 99/46277 A1 | 9/1999 |

OTHER PUBLICATIONS

Lazar E et al., Transforming growth factor alpha: mutation of aspartic acid 47 and leucine 48 results in different biological activities. Mol Cell Biol. 8:1247-1252, 1988.*
Burgess et al Possible dissociation of the heparin-binding and mitogenic activities of heparin-binding growth factor-1 from its receptor-binding activities by site-directed mutagenesis of a single lysine residue. J Cell Biol. 111:2129-2138, 1990.*
Bowie JU, et al Deciphering the message in protein sequences: tolerance to amino acid substitutions. Science. 247(4948):1306-1310, 1990.*
Matloubian et al. Lymphocyte egress from thymus and peripheral lymphoid organs is dependent on S1P receptor 1. Nature. Jan. 22, 2004;427(6972):355-60.*
Binderup et al. 20-epi-vitamin D3 analogues: a novel class of potent regulators of cell growth and immune responses. Biochem Pharmacol. Sep. 27, 1991;42(8):1569-75.*
Skolnick et al. From genes to protein structure and function: novel applications of computational approaches in the genomic era. Trends Biotechnol. 18(1):34-9, 2000.*
Hertweck et al. Asymmetric alph-chloroallylboration of Amino Aldehydes: A novel and Highly Versatile Route to D- an L-erythrosphingold bases. J, Org. Chem. 1999, 64:4426-4430.*
Wang et al. A single amino acid determines lysophospholipid specificity of the S1P1 (EDG1) and LPA1 (EDG2) phospholipid growth factor receptors. J Biol Chem. Dec. 28, 2001;276(52):49213-20.*
Kuntz. Structure-based strategies for drug design and discovery. Science. 1992 257(5073):1078-1082.*
Miller et al Ligand binding to proteins: the binding landscape model. Protein Sci. Oct. 1997;6(10):2166-79.*
Parrill et al., 2000. Identification of Edg1 Receptor Residues That Recognize Sphingosine 1-Phosphate. J. of Biological Chemistry 275: 39379-39384.*
Bornfeldt, K.E. et al. "Sphingosine-1-Phosphate Inhibits PDGF-Induced Chemotaxis of Human Arterial Smooth Muscle Cells: Spatial and Temporal Modulation of PDGF Chemotactic Signal Transduction," *J. Cell Biol.* Jul. 1995, pp. 193-206, vol. 130, No. 1.
Brinkmann, V. et al. "FTY720: A Novel Transplantation Drug that Modulates Lymphocyte Traffic Rather than Activation," *TIPS* Feb. 2000, pp. 49-52, vol. 21.
Chen, J.K. et al. "The Identification of Myriocin-Binding Proteins," *Chemistry and Biology* Apr. 1999, pp. 221-235, vol. 6.
Goetzl, E.J. et al. "Cutting Edge: Differential Constitutive Expression of Functional Receptors for Lysophosphatidic Acid by Human Blood Lymphocytes," *J. Immunol.* 2000, pp. 4996-4999, vol. 164.
Lee, M. et al. "Lysophosphatidic Acid Stimulates the G-Protein-Coupled Receptor EDG-1 as a Low Affinity Agonist," *J. Biol. Chem.* Aug. 21, 1998, pp. 22105-22112, vol. 273, No. 34.

(Continued)

*Primary Examiner*—Maher M Haddad
(74) *Attorney, Agent, or Firm*—Klarquist Sparkman, LLP

(57) ABSTRACT

The present invention relates to regulation of lymphocyte activation and migration. More particularly, the present invention is directed to nucleic acids encoding EDG family GPCR proteins, e.g., EDG-1, 2, 3, 4, 5, 6, 7, or 8, which are involved in modulation of lymphocyte activation and migration. The invention further relates to methods for identifying and using agents, including small organic molecules, antibodies, peptides, cyclic peptides, nucleic acids, antisense nucleic acids, sphingolipid analogs, and ribozymes, that modulate lymphocyte activation or migration via modulation of EDG GPCRs and EDG related signal transduction; as well as to the use of expression profiles and compositions in diagnosis and therapy related to lymphocyte activation and suppression, and lymphocyte migration.

23 Claims, 47 Drawing Sheets

OTHER PUBLICATIONS

Lee, M. et al. "Sphingosine-1-Phosphate as a Ligand for the G Protein-Coupled Receptor EDG-1," *Science* Mar. 6, 1998, pp. 1552-1555, vol. 279.

Mandala, S. et al. "Alteration of Lymphocyte Trafficking by Sphingosine 1-Phosphate Receptor Agonists," *Sciencexpress report* Mar. 28, 2002, 9 pages total.

Okamoto, H. et al. "EDG1 is a Functional Sphingosine-1-Phosphate Receptor that is Linked via a $G_{i/o}$ to Multiple Signaling Pathways, Including Phospholipase C Activation, $Ca^{2+}$ Mobilization, Ras-Mitogen-Activated Protein Kinase Activation, and Adenylate Cyclase Inhibition," *J. Biol. Chem.* Oct. 16, 1998, pp. 27104-27110, vol. 273, No. 42.

Pinschewer, D.D. et al. "FTY720 Immunosuppression Impairs Effector T Cell Peripheral Homing Without Affecting Induction, Expansion, and Memory," *J. of Immunol.* 2000, pp. 5761-5770, vol. 164.

Prieschl, E.E. and Baumruker, T. "Sphingolipids: Second Meesengers, Mediators and Raft Constituents in Signaling," *Immunology Today* Nov. 2000, pp. 555-560, vol. 21, No. 11.

Pyne, S. and Pyne, N.J. "Sphingosine 1-Phosphate Signaling in Mammalian Cells," *Biochem. J.* 2000, pp. 385-402, vol. 349.

Wang, F. et al. "Sphingosine 1-Phosphate Stimulates Cell Migration Through a $G_i$-Coupled Cell Surface Receptor," *J. Biol. Chem.* Dec. 10, 1999, pp. 35343-35350, vol. 274, No. 50.

Windh, R.T. et al. "Differential COupling of the Sphingosine 1-Phosphate Resceptors Edg-1, Edg-3, and H218/Edg-5 to the $G_j$, $G_q$, and $G_{12}$ Families of Heterotrimeric G Proteins," *J. Biol. Chem.* Sep. 24, 1999, pp. 27351-27358, vol. 274, No. 39.

An, Songzhu et al.; "Identification of cDNAs encoding two G protein-coupled receptors for lysosphingolipids"; 1997, *FEBS Letters*, vol. 417, pp. 279-282.

An, Songzhu et al.; "Transduction of Intracellular Calcium Signals through G Protein-Mediated Activation of Phospholipase C by Recombinant Sphingosine 1-Phosphate Receptors"; 1999, *Molecular Pharmacology*, vol. 55, pp. 787-794.

Chan, Andrew C. et al.; "ZAP-70: A 70 kd Protein-Tyrosine Kinase That Associates with the TCR ξ Chain"; 1992, *Cell*, vol. 71, pp. 649-662.

Chu, Peter et al.; "Systematic Identification of regulatory proteins critical for T-cell activation"; 2003, *Journal of Biology*, vol. 2, No. 3, article 21, 16 pages.

Goetzl, Edward J. et al.; "Diversity of cellular receptors and functions for the lysophospholipid growth factors lysophosphatidic acid and sphingosine 1-phosphate"; 1998, *The FASEB Journal*, vol. 12, pp. 1589-1598.

Hobson, John P. et al.; "Role of the Sphingosine-1-Phosphate Receptor EDG-1 in PDGF-Induced Cell Motility"; 2001, *Science*, vol. 291, pp. 1800-1803.

Holland, Sacha J. et al.; "Functional Cloning of Src-like Adaptor Protein 2 (SLAP-2), a Novel Inhibitor of Antigen Receptor Signaling"; 2001, *J. Exp. Med.*, vol. 194, No. 9, pp. 1263-1276.

Zheng, Yuhua et al.; "Lysophosphatidic Acid Receptor-Selective Effects on Jurkat T Cell Migration Through a Matrigel Model Basement Membrane"; 2001, *The Journal of Immunology*, vol. 166, No. 4, pp. 2317-2322.

Database EMBL, EDG1 human, Dec. 1, 1991, retrieved from EBI, Database accession No. P21453, XP002301458.

Database EMBL, Human EDG-1c receptor DNA, Nov. 18, 1999, retrieved from EBI, Database accession No. AAZ09756, XP002301459.

Beck, T.W. et al.; "The complete coding sequence of the human A-*raf*-1 oncogene and transforming activity of a human A-*raf* carrying retrovirus"; 1987, *Nucleic Acids Research*, vol. 15, No. 2, pp. 595-609.

Gjorloff-Wingren, Anette et al.; "Subcellular localization of intracellular protein tyrosine phosphatases in T cells"; 2000, *Eur. J. Immunol.*, vol. 30, pp. 2412-2421.

Tong, Yiai et al., "Cloning and Characterization of a Novel Mammalian PP2C Isozyme," *J. Biol. Chem.* 273(52):35282-35290 (1998).

\* cited by examiner

Coding region of full-length EDG1
SEQ ID NO:1

Met
[ATG]GGGCCCACCAGCGTCCCGCTGGTCAAGGCCCACCGCAGCTCGGTCTC
TGACTACGTCAACTATGATATCATCGTCCGGCATTACAACTACACGGGAA
AGCTGAATATCAGCGCGGACAAGGAGAACAGCATTAAACTGACCTCGGTG
GTGTTCATTCTCATCTGCTGCTTTATCATCCTGGAGAACATCTTTGTCTT
GCTGACCATTTGGAAAACCAAGAAATTCCACCGACCCATGTACTATTTTA
TTGGCAATCTGGCCCTCTCAGACCTGTTGGCAGGAGTAGCCTACACAGCT
AACCTGCTCTTGTCTGGGGCCACCACCTACAAGCTCACTCCCGCCCAGTG
GTTTCTGCGGGAAGGGAGTATGTTTGTGGCCCTGTCAGCCTCCGTGTTCA
GTCTCCTCGCCATCGCCATTGAGCGCTATATCACAATGCTGAAAATGAAA
CTCCACAACGGGAGCAATAACTTCGCCTCTTCCTGCTAATCAGCGCCTG
CTGGGTCATCTCCCTCATCCTGGGTGGCCTGCCTATCATGGGCTGGAACT
GCATCAGTGCGCTGTCCAGCTGCTCCACCGTGCTGCCGCTCTACCACAAG
CACTATATCCTCTTCTGCACCACGGTCTTCACTCTGCTTCTGCTCTCCAT
CGTCATTCTGTACTGCAGAATCTACTCCTTGGTCAGGACTCGGAGCCGCC
GCCTGACGTTCCGCAAGAACATTTCCAAGGCCAGCCGCAGCTCTGAGAAG
TCGCTGGCGCTGCTCAAGACCGTAATTATCGTCCTGAGCGTCTTCATCGC
CTGCTGGGCACCGCTCTTCATCCTGCTCCTGCTGGATGTGGGCTGCAAGG
TGAAGACCTGTGACATCCTCTTCAGAGCGGAGTACTTCCTGGTGTTAGCT
GTGCTCAACTCCGGCACCAACCCCATCATTTACACTCTGACCAACAAGGA
GATGCGTCGGGCCTTCATCCGGATCATGTCCTGCTGCAAGTGCCCGAGCG
GAGACTCTGCTGGCAAATTCAAGCGACCCATCATCGCCGGCATGGAATTC
AGCCGCAGCAAATCGGACAATTCCTCCACCCCAGAAAGACGAAGGGGA
CAACCCAGAGACCATTATGTCTTCTGGAAACGTCAACTCTTCTTCCTAG

EDG-1 mutant 1
SEQ ID NO:2

```
         Met
TTGGCACC ATG GGGCCCACCAGCGTCCCGCTGGTCAAGGCCCACCGCAGC
TCGGTCTCTGACTACGTCAACTATGATATCATCGTCCGGCATTACAACTA
CACGGGAAAGCTGAATATCAGCGCGGACAAGGAGAACAGCATTAAACTGA
CCTCGGTGGTGTTCATTCTCATCTGCTGCTTTATCATCCTGGAGAACATC
TTTGTCTTGCTGACCATTTGGAAAACCAAGAAATTCCACCGACCCATGTA
CTATTTTATTGGCAATCTGGCCCTCTCAGACCTGTTGGCAGGAGTAGCCT
ACACAGCTAACCTGCTCTTGTCTGGGGCCACCACCTACAAGCTCACTCCC
GCCCAGTGGTTTCTGCGGGAAGGGAGTATGTTTGTGGCCCTGTCAGCCTC
CGTGTTCAGTCTCCTCGCCATCGCCATTGAGCGCTATATCACAATGCTGA
AAATGAAACTCCACAACGGGAGCAATAACTTCCGCCTCTTCCTGCTAATC
AGCGCCTGCTGGGTCATCTCCCTCATCCTGGGTGGCCTGCCTATCATGGG
CTGGAACTGCATCAGTGCGCTGTCCAGCTGCTCCACCGTGCTGCCGCTCT
ACCACAAGCACTATATCCTCTTCTGCACCACGGTCTTCACTCTGCTTCTG
CTCTCCATCGTCATTCTGTACTGCAGAATCTACTCCTTGGTCAGGACTCG
GAGCCGCCGCCTGACGTTCCGCAAGAACATTTCCAAGGCCAGCCGCAGCT
CTGAGAAGTCGCTGGCGCTGCTCAAGACCGTAATTATCGTCCTGAGCGTC
TTCATCGCCTGCTGGGCACCGCTCTTCATCCTGCTCCTGCTGGATGTGGG
CTGCAAGGTGAAGACCTGTGACATCCTCTTCAGAGCGGAGTACTTCCTGG
TGTTAGCTGTGCTCAACTCCGGCACCAACCCCATCATTTACACTCTGACC
AACAAGGAGATGCGTCGGGCCTTCATCCGGATCATGTCCTGCTGCAAGTG
CCCGAGCGGAGACTCTGCTGGCAAATTCAAGC
```

EDG-1 mutant 2
SEQ ID NO:3

GCGGCCGCGTCGACGTGCGTCTCAGCAGTTCAGATCCGGGGGCC
CCCAGCTGACAGAGGGCGTGGGGGGTTAAGGCATTAACCCCTCCCAGCCT
CTTCCTGAAGAAACCACCCAGCCTTGGCGCGGCGCTGGGTGACTTCGCGT
AGCAGGCAGGGAACTGGCCGCGGCGAGCGGGACTGGCCATTGGAGTGCTC
CGCTGCGGAGGGAGGGGACCCCGACTCGAGTAAGTTTGCGAGAGCACTAC
GCAGTCAGTCGGGGGCAGCAGCAAGATGCGAAGCGAGCCGTACAGATCCC
GGGCTCTCCGAACGCAACTTCGCCCTGCTTGAGCGAGGCTGCGGTTTCCG
AGGCCCTCTCCAGCCAAGGAAAAGCTACACAAAAGCCTGGATCACTCAT
CGAACCACCCCTGAAGCCAGTGAAGGCTCTCTCGCCTCGCCCTCTAGCGT
TCGTCTGGAGTAGCGCCACCCCGGCTTCCTGGGGACACAGGGTTGGCACC
Met
ATG GGGCCCACCAGCGTCCCGCTGGTCAAGGCCCACCGCAGCTCGGTCTC
TGACTACGTCAACTATGATATCATCGTCCGGCATTACAACTACACGGGAA
AGCTGAATATCAGCGCGGACAAGGAGAACAGCATTAAACTGACCTCGGTG
GTGTTCATTCTCATCTGCTGCTTTATCATCCTGGAGAACATCTTTGTCTT
GCTGACCATTTGGAAAACCAAGAAATTCCACCGACCCATGTACTATTTTA
TTGGCAATCTGGCCCTCTCAGACCTGTTGGCAGGAGTAGCCTACACAGCT
AACCTGCTCTTGTCTGGGGCCACCACCTACAAGCTCACTCCGCCCAGTG
GTTTCTGCGGGAAGGGAGTATGTTTGTGGCCCTGTCAGCCTCCGTGTTCA
GTCTCCTCGCCATCGCCATTGAGCGCTATATCACAATGCTGAAAATGAAA
CTCCACAACGGGAGCAATAACTTCCGCCTCTTCCTGCTAATCAGCGCCTG
CTGGGTCATCTCCCTCATCCTGGGTGGCCTGCCTATCATGGGCTGGAACT
GCATCAGTGCGCTGTCCAGCTGCTCCACCGTGCTGCCGCTCTACCACAAG
CACTATATCCTCTTCTGCACCACGGTCTTCACTCTGCTTCTGCTCTCCAT
CGTCATTCTGTACTGCAGAATCTACTCCTTGGTCAGGACTCGGAGCCGCC
GCCTGACGTTCCGCAAGAACATTTCCAAGGCCAGCCGCAGCTCTGAGAAG
TCGCTGGCGCTGCTCAAGACCGTAATTATCGTCCTGAGCGTCTTCATCGC
CTGCTGGGCACCGCTCTTCATCCTGCTCCTGCTGGATGTGGGCTGCAAGG
TGAAGACCTGTGACATCCTCTTCAGAGCGGAGTACTTCCTGGTGTTAGCT
GTGCTCAACTCCGGCACCAACCCCATCATTTACACTCTGACCA

EDG-1 mutant 3
SEQ ID NO:4

GGCACGAGGCGAGCGGGACTGGCCATTGGAGTGCTCCGCTGCGGAGGGAG
GGGACCCCGTACTCGAGTAAGTTTGCGAGAGCACTACGCAGTCAGTCGGG
GGCAGCAGCAAGATGCGAAGCGAGCCGTACAGATCCCGGGCTCTCCGAAC
GCAACTTCGCCCTGCTTGAGCGAGGCCGCGGTTTCCGAGGCCCTCTCCAG
CCAAGGAAAAGCTACACAAAAGCCTGGATCACTCATCGAACCACCCCTG
AAGCCAGTGAAGGCTCTCTCGCCTCGCCCTCTAGCGTTCGTCTGGAGTAG
                                            Met
CGCCACCCCGGCTTCCTGGGGACACAGGGTTGGCACC<u>ATG</u>GGGCCCACCA
GCGTCCCGCTGGTCAAGGCCCACCGCAGCTCGGTCTCTGACTACGTCAAC
TATGATATCATCGTCCGGCATTACAACTACACGGGAAAGCCGAATATCAG
CGCGGACAAGGAGAACAGCATTAAACTGACCTCGGTGGTGTTCATTCTCA
TCTGCTGCTTTATCATCCTGGAGAACATCTTTGTCTTGCTGACCATTTGG
AAAACCAAGAAATTCCACCGACCCATGTACTATTTTATTGGCAATCTGGC
CCTCTCAGACCTGTTGGCAGGAGTAGCCTACACAGCTAACCTGCTCTTGT
CTGGGGCCACCACCTACAAGCTCACTCCCGCCCAGTGGTTTCTGCGGGAA
GGGAGTATGTTTGTGGCCCTGTCAGCCTCCGTGTTCAGTCTCCTCGCCAT
CGCCATTGAGCGCTATATCACAATGCTGAAAATGAAACTCCACAACGGGA
GCAATAACTTCCGCCTCTTCCTGCTAATCAGCGCCTGCTGGGTCATCTCC
CTCATCCTGGGTGGCCTGCCTATCATGGGCTGGAACTGCATCAGTGCGCT
GTCCAGCTGCTCCACCGTGCTGCCGCTCTACCACAAGCACTATATCCTCT
TCTGCACCACGGTCTTCACTCTGCTTCTGCTCTCCATCGTCATTCTGTAC
TGCAGAATCTACTCCTTGGTCAGGACTCGGAGCCGCCGCCTGACGTTCCG
CAAGAACATTTCCAAGGCCAGCCGCAGCTCTGAGAAGTCGCTGGCGCTGC
TCAGGACCGTAATTATCGTCCTGAGCGTCTTCATCGCCTGCTGGGCACCG
CTCTTCATCCTGCTCCTGCTGGATGTGGGCTGCAAGGTGAAGACCTGTGA
CATCCTCTTCAGAGCGGAGTACTTCCTGGTGTTAGCTGTGCTCAACTCCG
GCACCAACCCCATCATTTACACTCTGACCAACAAGGAGATGCGTCGGGCC
TTCATCCGGATCATGTCCTGCTGCAAGTGCCCGAGCGGAGACTCTGCTGG
CAAATTCAAGCGACCCATCATCGCCG

```
                                    . . . . . . . . . . . . . . . . . . . . . Y . . . . . . . . . . . . . . . . . . . . . . .   Consensus #1
                                                                                                                    60
  1  -----MGPTSVPLVKAHRSSVSDYVNYDIVRHYNYTGKINIS-ADKENSIKITSVVFIL                                                           huEDG1.pep
  1  MAAISTSIPVISQPQFTAMNEPQCFYNESIAFFYNRSGKHIATEWN--TVSKLVMGLIT                                                           huEDG2.pep
  1  -----MATALPPRLQEVRGNETLREHYQYVGKLAGRLKEASEGSTLTTVLFLV                                                                 huEDG3.pep
  1  -----MVIMGQCYNETIGEEHNNSGKETSHMR--PKDVVMALGIT                                                                         huEDG4.pep
  1  -----MGSLYSEYLNPNKVQE----HYNYTKETLET--QETTSRQVASAFIVI                                                                 huEDG5.pep
  1  -----MNATGTPVAPESCQQLAAGGHSRLIVLHYNHSGRIAGRGGPEDGGIGALRGISVA                                                          huEDG6.pep
  1  -----MNECHYMDKHMDFYNRSNTDTVDDWT-GTKLVIILCVGTF                                                                         huEDG7.pep
  1  -----MESGLLRAPVSEMIVLHYNYTGKIRGARYQPGAGIRADAAVCLA                                                                     ratEDG8.pep . . . . . N . . V . . . . . . . . . . . . . D . . . G . A . . . . . . . . . . . G . . . . . . L . .   Consensus #1
                                                                                                                    120
 55  ICCFILENLEVLTIWKTKFHRPMYYFIGNLAISDLLAGVAYTANLLLSGATTYKLTP                                                              huEDG1.pep
 59  VCIFIMIANLIVMVAIYVNRFHFETYYIMANLAAADFFAGLAYFYLMFNTGPNTRRLTV                                                            huEDG2.pep
 49  ICSFIVLENLMVLIAIWKNNKFHNRMYFFIGNLALCDLLAGIAYKVNILMSGKKTFSLSE                                                           huEDG3.pep
 42  VSVLVLLFNLIVLLTIAAIASNRRFHQPIYYLLGNLAAADLFAGVAYLFLMFHTGPRTARLSL                                                        huEDG4.pep
 43  LCCAIVVENLIVILTIAVDRSKFHSAMYLFIGNLAASMLFLGNIAASMLFHGNIAASLFLGNIAASLFLGNIAASLFLGNIAASLFLGNIAAS                          huEDG5.pep
 56  ASCIVVLENLIVLAAITSHMRSRRWVYYCIVNITLSDLITGAAYIANVLLSGARDFRLAE                                                           huEDG6.pep
 40  FCLFIFFSNSLVIAAVIKNRKFHFFFYLLANLAAADFFAGIAYFLMFNTGPVSKTLTV                                                             huEDG7.pep
 46  VCAFIVLENLAVILVLGRHPRFHAPMFILLGSLTISDLLAGAAYANILLSGRITLRLSE                                                            ratEDG8.pep
```

FIG. 2.

```
        .W...R.G.....L.AS...LL..A.ER..........R........W.......  Consensus #1
                                                        180
115 AQWFLREGSMEVALSASVFSLLAIAIERYIITMLK-MKLHNGSNNFRLFLLISACWVISLI  huEDG1.pep
119 STWFLRQGLIDTSLTASVANLLAIAIERHLTVFR-MQLHTRMSNRRVVVTVVIWTMAIV   huEDG2.pep
109 TVWFLREGSMEVALGASTCSLIAIAIERHLTMIK-MRPYDANKRHRVELLIGMCWLIAFT  huEDG3.pep
102 EGWFLRQGLLDTSLTASVATLLAIAIERHRSVMA-VQLHSRLPRGRVVMLIVGVWVAAIG  huEDG4.pep
103 VQWFAREGSASITLSASVFSLLAIAIERHVAIAK-VKLYGSDKSCRMLLIGASWLISLV   huEDG5.pep
116 AQWFLREGLLFTALAASTESLLFTAGEREFATMVRPVAESGATKTSRVYGFIGCWLLAAL  huEDG6.pep
100 NRWFLRQGLLDSSLTASLTNLLVIAVERHMSIMR-MRVEHSNLTKKRVTLLLLVWALAIF  huEDG7.pep
106 ALWFAREGGVEVALAASVISLLAIAIERHLTMAR-RGPARAASRARTLAMAVAAWGLSLL  ratEDG8.pep .G..P....W.C........CS.....P......Y....Y..i....V.......  Consensus #1
                                                        240
174 LGGLPIMGWNCISALSSCSTVLPLYHKHYILFCT-TVFTLLILSIVIIYCRIYSLVRTRS  huEDG1.pep
178 MGALIPSVGWNCICDIENCSNMAPLYSDSYLVFWAIFNLVTFVV-MVVLYAHIFGYVRQRT  huEDG2.pep
168 LGALPILGWNCICHNLPDCSTILPLYSKKYIAFCI-SIFTAIIVTIVILLI-MVVLHYASS  huEDG3.pep
161 LGILPAHSWHCLCAIDRCSRMAPLISRSYLPLYAKHYVL-CVVTIFSIILLAICALYARII  huEDG4.pep
162 LGGLPILGWNCLCGHLEACSTVLPLYAKHYVLYSKRYILFCLV-IFAGVIATIMGLVRBSH  huEDG5.pep
176 LGMLPLLGWNCLCAFDRCSSILPLYSKRYILFCLV-IFAGVIATIMGLYGAIFRLVQASG  huEDG6.pep
159 MGAVPTLGWNCLCNISACSSLAPIYSRSYLMFWTVSNLMAFLI-MVVYLRIHYVYVKRKT  huEDG7.pep
165 LGILPALGWNCLGRLEACSTVLPLYAKAYMVLFCVLAFLGI-LAAICALYARIIYCQVRANA  ratEDG8.pep
```

FIG. 2. (CONTINUED)

```
                                                          .     Consensus #1
                                                          420
343 PIIAG------MEFSRKS---DNSSHPQKDEGDNPETIMSSGNVNSSS.            huEDG1.pep
329 ---------QRS------ENPTGPTESSDRSASSINHTILAGVHSNDHSVV.         huEDG2.pep
327 PIQPA-----TDPSRSKSSSNNSSHSPKVKEDLPHTDPSSCIMDKNAALQNGIFCN.   huEDG3.pep
314 ---------CLRQS---TRESVHYTSSAQGGASTRIMLPENGHPLMDSTL.          huEDG4.pep
309 GVGVQG---RR------RVGTPGHHLLPLRSSSSLERGMHMPTSPTFLEGNTVV.      huEDG5.pep
329 -LGMRGPG--DCIARAVEAHSGASTTDSSLRPRDSFRGSRSISFRMREPLSSISSVRSI. huEDG6.pep
312 ---------SQENP---ERRPSRIPSTVLSRSDTGSQYIEDSISQGAVCNKSTS.      huEDG7.pep
343 AVGPSGGLRRCIPPTLDRSSSPSEHSCPQRDGMDTSCSTGSPGAATANRTIVPDATD.   ratEDG8.pep Consensus 'Consensus #1': When all match the residue of the Consensus show the
residue of the Consensus, otherwise show '.'.

Decoration 'Decoration #1': Box resideues that match the Consensus exactly.
```

FIG. 2. (CONTINUED)

Known TCR Regulators Uncovered from CD69 cDNA Screen c3.1

| Identity | Classification | Protein Family | Successful Phenotype Transfer of DNA | Direction | Length |
|---|---|---|---|---|---|
| TCRβ (multiple) | Known | receptor | on-hold | Sense | Partial |
| LCK | Known | Tyr kinase | Yes | Sense | Partial |
| ZAP70 | Known | Tyr kinase | Yes | Sense | Partial |
| SYK | Known | Tyr kinase | Yes | Sense | Partial |
| PLCγ1 | Known | phospholipase | Yes | Sense | Partial |
| PAG/cbp | Known | TM adaptor | on-hold | Sense | Partial |
| A-raf-1 | Known | Ser/Thr kinase | on-hold | Sense | Partial |
| SHP/PTP1C | Known | Ser/Thr phosphatase | on-hold | Sense | Partial |
| CSK | Known | Tyr kinase | on-hold | Sense | Partial |
| Nucleolin | Known | RNA-binding | on-hold | Sense | Partial |

FIG. 13

Primary Potential Hits from CD69 cDNA Screen c3.1

| Identity | Protein Family | Successful Phenotype Transfer | Direction | Length |
|---|---|---|---|---|
| Novel 1 | Ser/Thr kinase | Yes | Sense | Partial |
| Novel 2 | Tyr phosphatase | Yes | Sense | Partial |
| Novel 3 | GPCR (receptor) | Yes | Sense | Partial |
| Novel 4 | cytokine receptor | Yes | Sense | Partial |
| Novel 5 | trans-membrane receptor | Yes | Sense | Partial |
| Novel 6 | TNF-α induced mRNA | Yes | Sense | full-length |
| Novel 7 | Zinc finger | Yes | Sense | Partial |

FIG. 14

EDG: MODULATORS OF LYMPHOCYTE ACTIVATION AND MIGRATION

CROSS-REFERENCES TO RELATED APPLICATIONS

The present application claims priority to U.S. Ser. No. 60/284,763, filed Apr. 18, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of lymphocyte activation and migration. More particularly, the present invention is directed to nucleic acids encoding EDG family GPCR proteins, e.g., EDG-1, 2, 3, 4, 5, 6, 7, or 8, which are involved in modulation of lymphocyte activation and migration. The invention further relates to methods for identifying and using agents, including small organic molecules, antibodies, peptides, cyclic peptides, nucleic acids, antisense nucleic acids, sphingolipid analogs, and ribozymes, that modulate lymphocyte activation or migration via modulation of EDG GPCRs and EDG related signal transduction; as well as to the use of expression profiles and compositions in diagnosis and therapy related to lymphocyte activation and suppression, and lymphocyte migration.

BACKGROUND OF THE INVENTION

The immune response includes both a cellular and a humoral response. The cellular response is mediate largely by T lymphocytes (alternatively and equivalently referred to herein as T cells), while the humoral response is mediated by B lymphocytes (alternatively and equivalently referred to herein as B cells). Lymphocytes play a number of crucial roles in immune responses, including direct killing of virus-infected cells, cytokine and antibody production, and facilitation of B cell responses. Lymphocytes are also involved in acute and chronic inflammatory disease; asthma; allergies; autoimmune diseases such as scleroderma, pernicious anemia, multiple sclerosis, myasthenia gravis, IDDM, rheumatoid arthritis, systemic lupus erythematosus, and Crohn's disease; and organ and tissue transplant disease, e.g., graft vs. host disease.

B lymphocytes produce and secrete antibodies in response to the concerted presentation of antigen and MHC class II molecules on the surface of antigen presenting cells. Antigen presentation initiates B cell activation through the B cell receptor (BCR) at the B cell surface. Signal transduction from the BCR leads to B cell activation and changes in B cell gene expression, physiology, and function, including secretion of antibodies.

T cells do not produce antibodies, but many subtypes of T cells produce co-stimulatory molecules that augment antibody production by B cells during the humoral immune response. In addition, many T cells engulf and destroy cells or agents that are recognized by cell surface receptors. Engagement of the cell surface T cell receptor (TCR) initiates T cell activation. Signal transduction from the TCR leads to T cell activation and changes in T cell gene expression, physiology, and function, including the secretion of cytokines.

Identifying ligands, receptors, and signaling proteins downstream of TCR, as well as BCR, activation is important for developing therapeutic regents to inhibit immune response in inflammatory disease, autoimmune disease, and organ transplant, as well as to activate immune response in immunocompromised subjects, and in patients with infectious disease and cancer (see, e.g., Rogge et al., *Nature Genetics* 25:96-101 (2000)). In addition, identification of molecules participating in lymphocyte migration is important for developing therapeutic reagents, as described above,

SUMMARY OF THE INVENTION

The present invention therefore provides nucleic acids encoding EDG G-protein coupled receptors (GPCRs), e.g., EDG-1, 2, 3, 4, 5, 7, and 8, which are involved in modulation of lymphocyte activation and migration. The invention therefore provides methods of screening for compounds, e.g., SPP and LPA analogs, including sphingolipid-like compounds, small organic molecules, antibodies, peptides, lipids, peptides, cyclic peptides, nucleic acids, antisense molecules, and ribozyme, that are capable of modulating lymphocyte activation and lymphocyte migration, e.g., either activating or inhibiting lymphocytes and their ability to migrate. Therapeutic and diagnostic methods and reagents are also provided.

In one aspect of the invention, nucleic acids encoding EDG GPCRs, e.g., EDG-1, 2, 3, 4, 6, 7, and 8 protein, are provided. In another aspect, the present invention provides nucleic acids, such as probes, antisense oligonucleotides, and ribozymes, that hybridize to a gene encoding an EDG protein, e.g., EDG-1, 2, 3, 4, 6, 7, or 8. In another aspect, the invention provides expression vectors and host cells comprising EDG-encoding nucleic acids, e.g., EDG-1, 2, 3, 4, 6, 7, or 8. In another aspect, the present invention provides EDG protein, e.g., EDG-1, 2, 3, 4, 6, 7, or 8, and antibodies thereto.

In another aspect, the present invention provides a method for identifying a compound that modulates lymphocyte activation or lymphocyte migration, the method comprising the steps of: (i) contacting a cell comprising an EDG polypeptide or fragment thereof with the compound, the EDG polypeptide or fragment thereof encoded by a nucleic acid that hybridizes under stringent conditions to a nucleic acid comprising a nucleotide sequence of EDG 1, 2, 3, 4, 5, 6, 7, or 8; and (ii) determining the chemical or phenotypic effect of the compound upon the cell comprising the EDG polypeptide or fragment thereof, thereby identifying a compound that modulates lymphocyte activation or migration.

In another aspect, the present invention provides a method for identifying a compound that modulates lymphocyte activation or migration, the method comprising the steps of: (i) contacting the compound with an EDG polypeptide or a fragment thereof, the EDG polypeptide or fragment thereof encoded by a nucleic acid that hybridizes under stringent conditions to a nucleic acid comprising a nucleotide sequence of EDG 1, 2, 3, 4, 5, 6, 7, or 8; (ii) determining the physical effect of the compound upon the EDG polypeptide; and (iii) determining the chemical or phenotypic effect of the compound upon a cell comprising an EDG polypeptide or fragment thereof, thereby identifying a compound that modulates lymphocyte activation or migration.

In one embodiment, the EDG polypeptide or fragment thereof is encoded by a nucleic acid that hybridizes under stringent conditions to a nucleic acid comprising a sequence of SEQ ID NO:1-4.

In another embodiment, the host cell is a B lymphocyte or a T lymphocyte. In another embodiment, the host cell is a primary or cultured cell, e.g., a BJAB or Jurkat cell.

In one embodiment, the chemical or phenotypic effect is determined by measuring CD69 expression, IL-2 production, intracellular Ca2+ mobilization, or lymphocyte proliferation.

In another embodiment, modulation is inhibition of T or B lymphocyte activation or migration.

In another embodiment, the polypeptide is recombinant.

In another embodiment, the EDG polypeptide is selected from the group consisting of EDG-1, 3, 5, 6, 7, or 8. In another embodiment, the EDG polypeptide is an EDG-1 polypeptide encoded by a nucleic acid selected from the group consisting of SEQ ID NOS:1,2,3, and 4.

In one embodiment, the EDG-1 fragment is an extracellular domain. In another embodiment, the EDG-1 fragment is a cytoplasmic domain. In another embodiment, the polypeptide further comprises at least one transmembrane domain of an EDG polypeptide.

In another embodiment, the EDG polypeptide or fragment thereof has GPCR activity.

In another embodiment, the compound is an antibody, an antisense molecule, a peptide, a circular peptide, a small organic molecule, a sphingolipid, a sphingolipid analog, either naturally occurring or synthetic, e.g., 2-amino-2(2-[4-octylphenyl]ethyl)-1,3-propanediol hydrochloride or an analog thereof.

In one embodiment, the chemical or phenotypic effect is determined by measuring lymphocyte migration in vitro toward an EDG ligand, e.g., SPP or LPA.

In one aspect, the present invention provides a method of modulating lymphocyte activation or migration in a subject, the method comprising the step of administering to the subject a therapeutically effective amount of a compound identified using the methods described above.

In one embodiment, the subject is a human.

In another aspect, the present invention provides a composition comprising a therapeutically effective amount of an analog of 2-amino-2(2-[4-octylphenyl]ethyl)-1,3-propanediol hydrochloride and a physiologically acceptable carrier.

In one embodiment, the present invention provides method of modulating lymphocyte activation or migration in a subject, the method comprising the step of administering to the subject a therapeutically effective amount of an EDG polypeptide, the polypeptide encoded by a nucleic acid that hybridizes under stringent conditions to a nucleic acid comprising a nucleotide sequence of EDG 1, 2, 3, 4, 5,6 ,7, or 8.

In one embodiment, the EDG polypeptide or fragment thereof is encoded by a nucleic acid that hybridizes under stringent conditions to a nucleic acid comprising a sequence of SEQ ID NO:1-4. In another embodiment, the EDG polypeptide is selected from the group consisting of EDG-1, 3, 5, 6, 7, and 8. In another embodiment, the EDG polypeptide is an EDG-1 polypeptide encoded by a nucleic acid selected from the group consisting of SEQ ID NO:1, 2, 3, and 4.

In another aspect, the present invention provides a method of modulating lymphocyte activation or migration in a subject, the method comprising the step of administering to the subject a therapeutically effective amount of a nucleic acid encoding an EDG polypeptide or fragment thereof, wherein the nucleic acid hybridizes under stringent conditions to a nucleic acid encoding a polypeptide comprising a nucleotide sequence of EDG 1, 2, 3, 4, 5, 6, 7, or 8.

In one embodiment, the EDG nucleic acid or fragment thereof is encoded by a nucleic acid that hybridizes under stringent conditions to a nucleic acid comprising a sequence of SEQ ID NO:1-4. In another embodiment, the EDG nucleic acid is selected from the group consisting of EDG-1, 3, 5, 6, 7, and 8. In another embodiment, the EDG nucleic acid is an EDG-1 nucleic acid selected from the group consisting of SEQ ID NO:1, 2, 3, and 4.

In one aspect, the present invention provides a method of modulating T lymphocyte migration and activation in a subject, the method comprising the step of administering to the subject a therapeutically effective amount of a first compound identified using the methods described above, which first compound modulates activation, and administering to the subject a therapeutically effective amount of a second compound identified using the methods described above, which second compound modulates migration.

In another aspect, the present invention provides a method of modulating T lymphocyte migration and activation in a subject, the method comprising the step of administering to the subject a therapeutically effective amount of a compound identified using the methods described above, which compounds modulates both activation and migration.

In another aspect, the present invention provides a method of screening for modulators of lymphocyte activation, the methods comprising the steps of: (i) transfecting into lymphocytes a cDNA library; (ii) stimulating T or B cell receptors of the lymphocytes; (iii) screening for modulation of lymphocyte activation by detecting the level of CD69 cell surface expression via FACS; and (iv) rescuing cDNAs that modulate lymphocyte activation.

In one embodiment, the lymphocytes are T cells, e.g., cultured T cells, e.g., Jurkat cells.

In another embodiment, cDNAs of the library are operably linked to an inducible promoter, e.g., a tetracycline regulatory element and a thymidine kinase promoter.

In another embodiment, the library is transfected by retroviral vectors. In another embodiment, the cDNA library is from a primary lymphocyte organ, e.g., thymus, spleen, lymph node, and bone marrow.

In another embodiment, the modulation is inhibition of T lymphocyte activation.

BRIEF DESCRIPTION OF THE DRAWINGS

FIG. 1 provides the nucleotide sequence that encodes four EDG-1 proteins. SEQ ID NO:1 is the nucleotide sequence of wild-type EDG-1 (382 amino acids in length; SEQ ID NO:5); SEQ ID NO:2 is the nucleotide sequence of mutant #1 (341 amino acids in length; SEQ ID NO:13); SEQ ID NO:3 is the nucleotide sequence of mutant #2 (314 amino acids in length; SEQ ID NO:14); and SEQ ID NO:4 is the nucleotide sequence of mutant #3 (346 amino acids in length; SEQ ID NO:15). Each of the mutant EDG-1 polypeptides is truncated at the C-terminus relative to the wild-type EDG-1.

FIG. 2 shows a sequence comparison of EDG family proteins (SEQ ID NOS:5-12).

FIG. 13 shows known TCR regulators identified from a CD69 cDNA screen.

FIG. 14 shows primary, novel TCR regulators identified from a CD69 cDNA screen.

DETAILED DESCRIPTION OF THE INVENTION

Introduction

Figure 3:
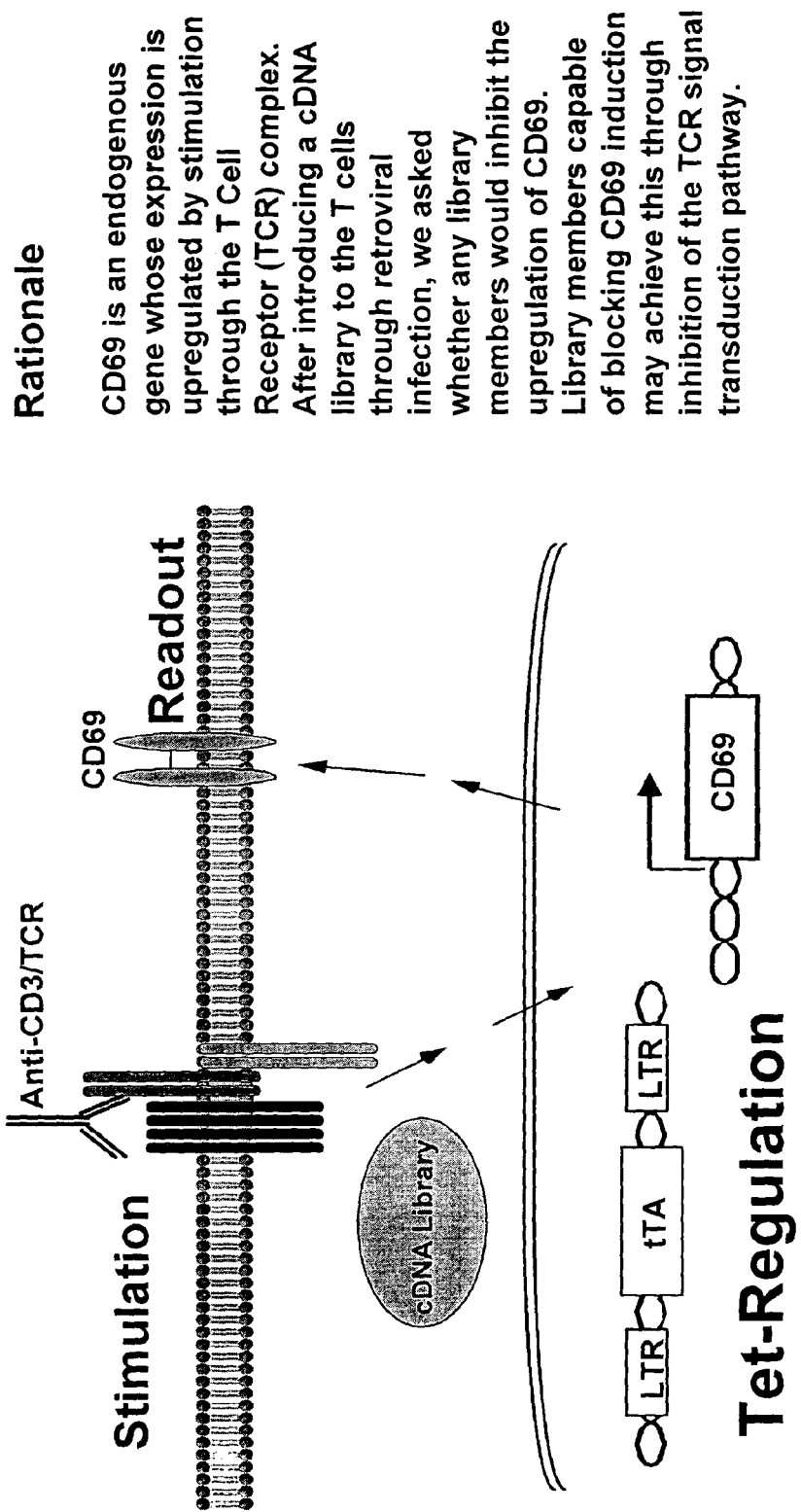
FIG. 3 shows a schematic of identification of regulatory proteins that affect T cell activation.
Figure 4:
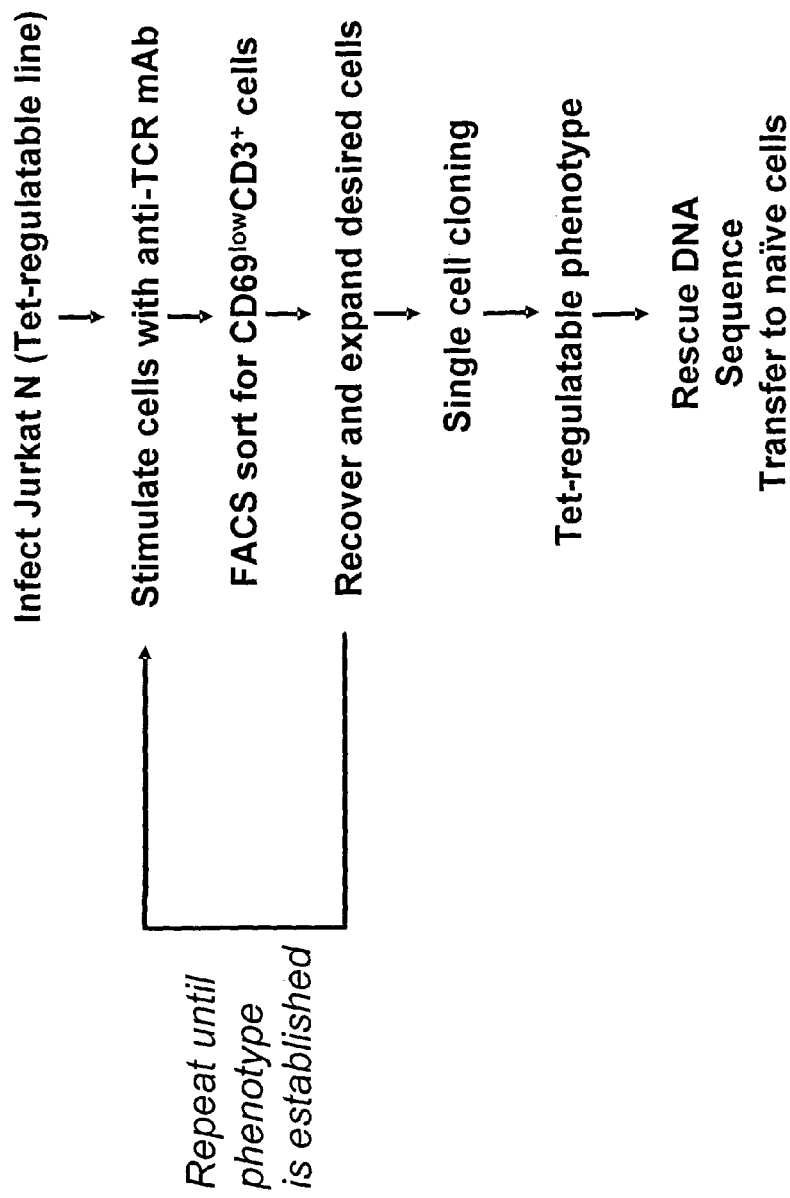
FIG. 4 shows a schematic of TCR activation-induced expression of CD69.
Figure 5:
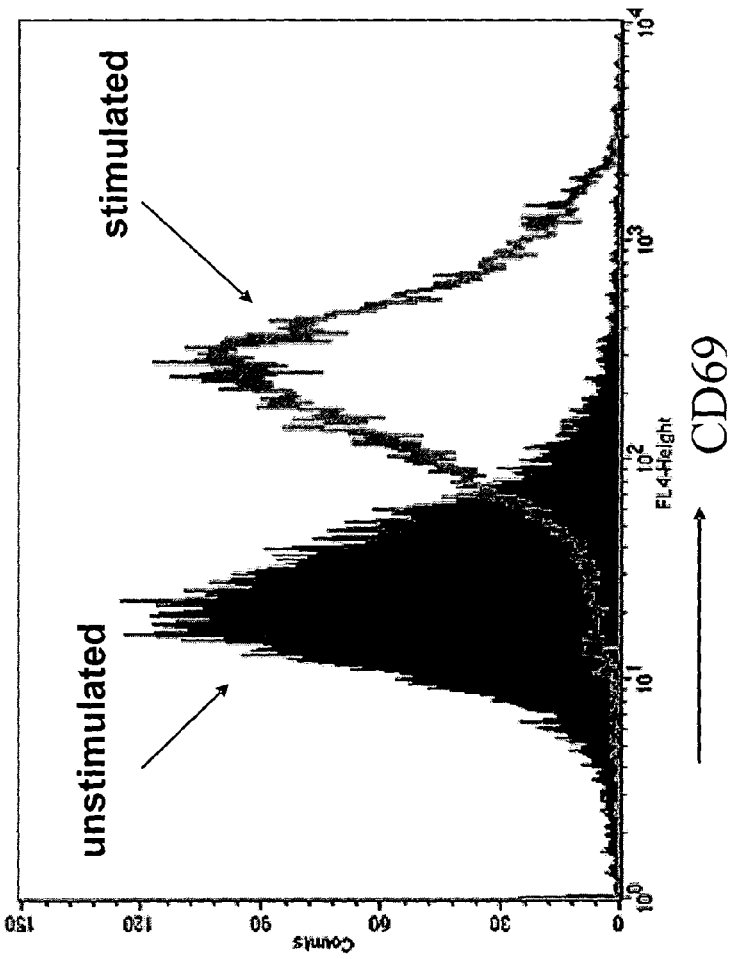
FIG. 5 shows induction of endogenous CD69 by anti-TCR.
Figure 6:
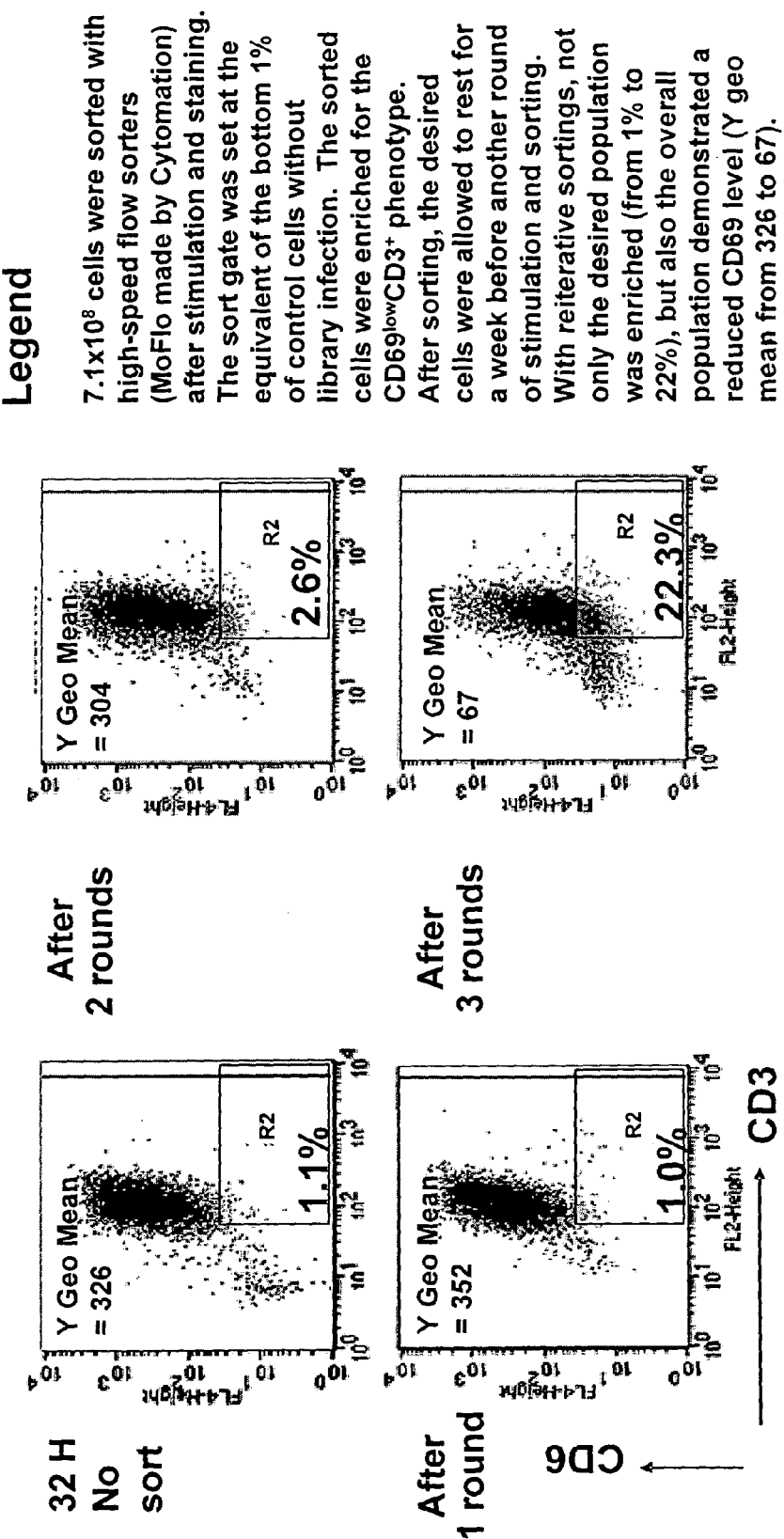
FIG. 6 shows phenotypic enrichment through sequential FACS sorting.
Figure 7:
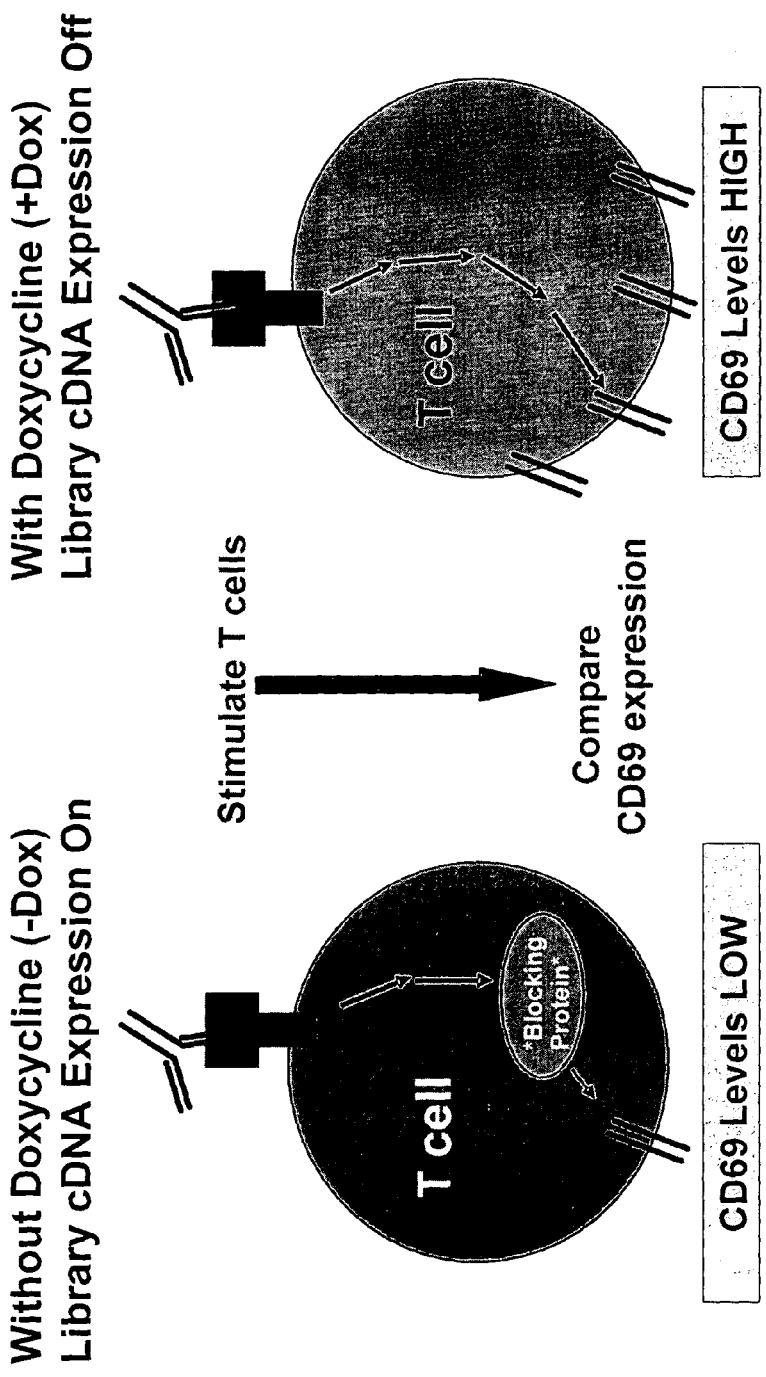
FIG. 7 shows a schematic of the distinction between cDNA-induced phenotypes and somatic mutations.
Figure 8:
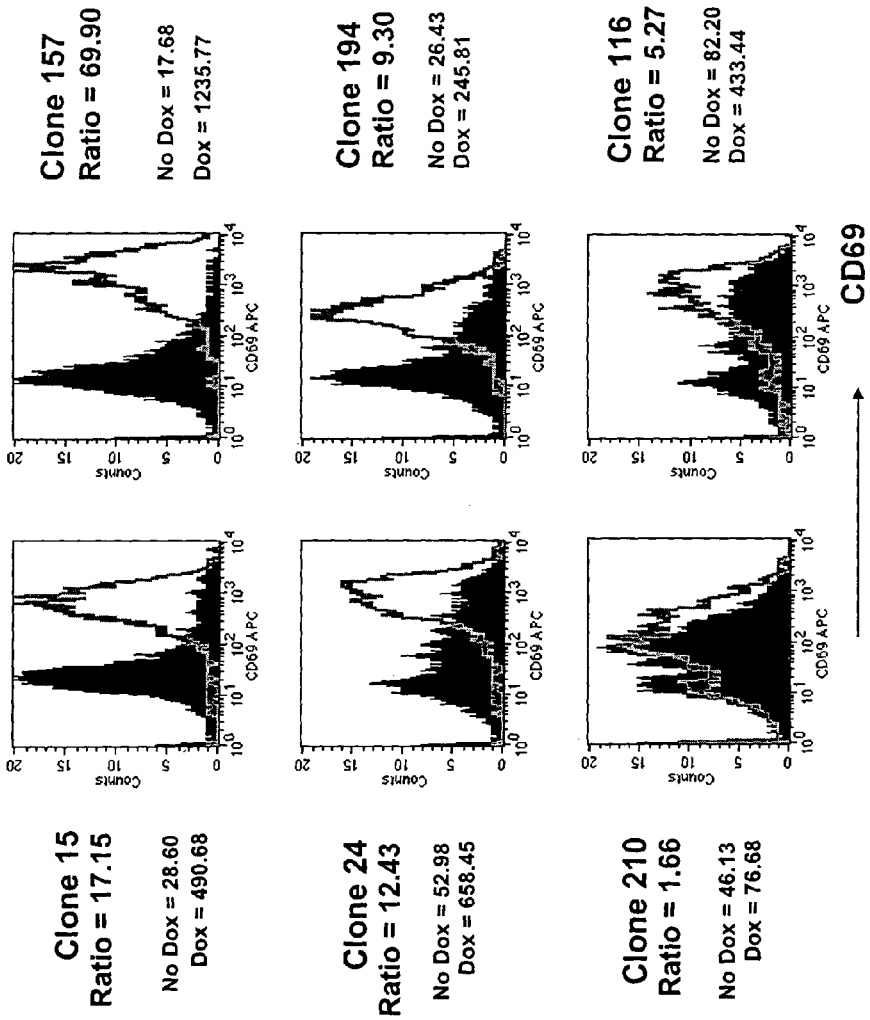
FIG. 8 shows dox-regulatable phenotypes in clones after TCR stimulation.
Figure 9:
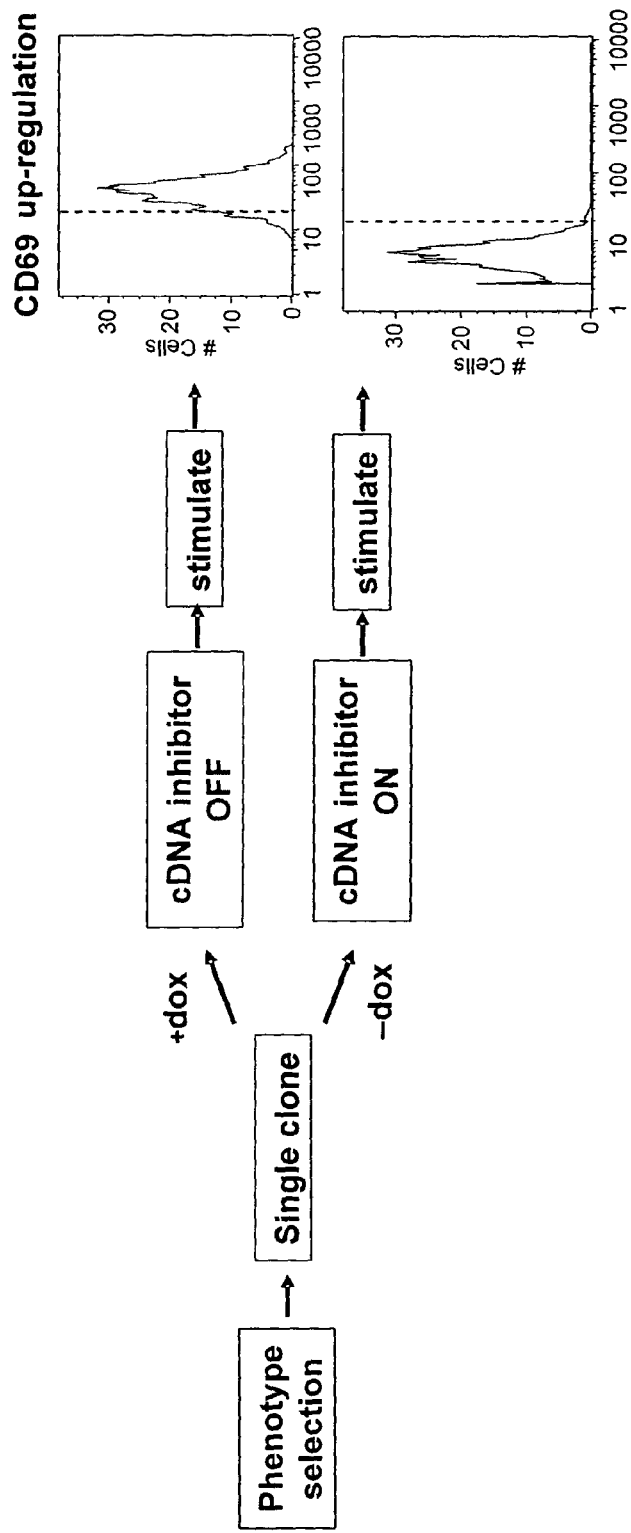
FIG. 9 shows a schematic of phenotypic assays in Jurkat cells.
Figure 10:
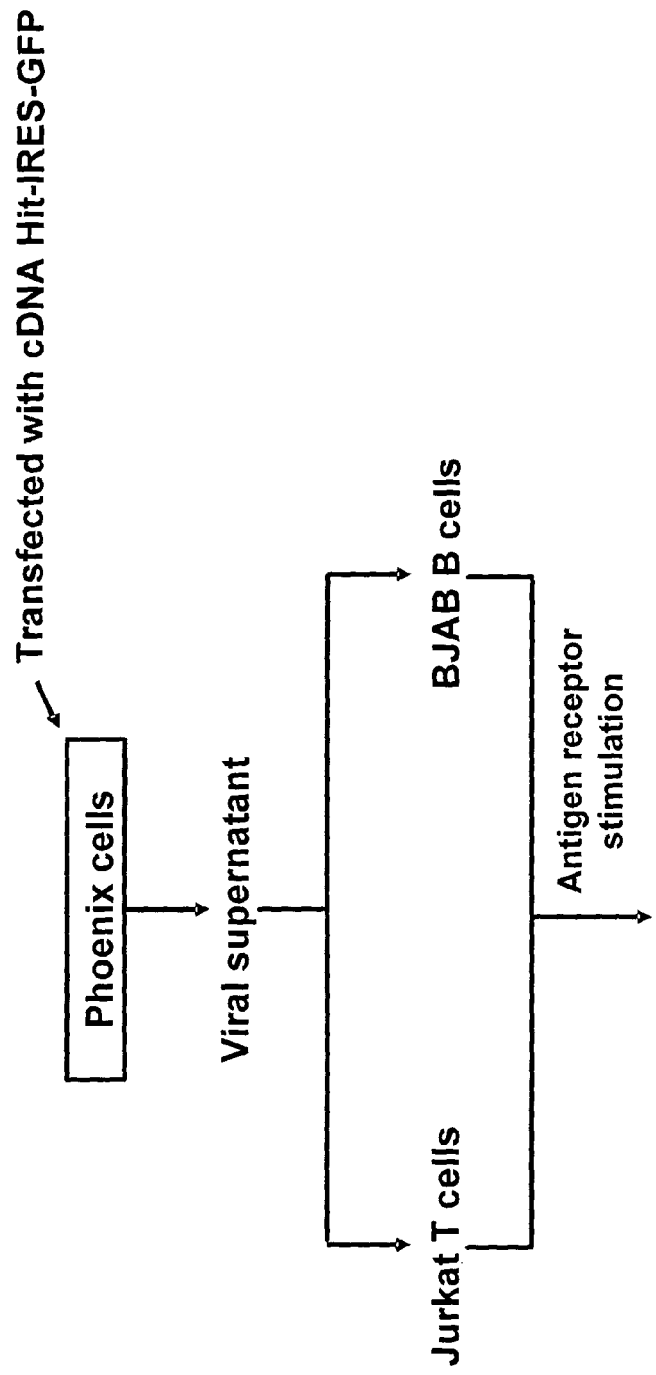
FIG. 10 shows a schematic of cell specificity of potential targets.
Figure 11:
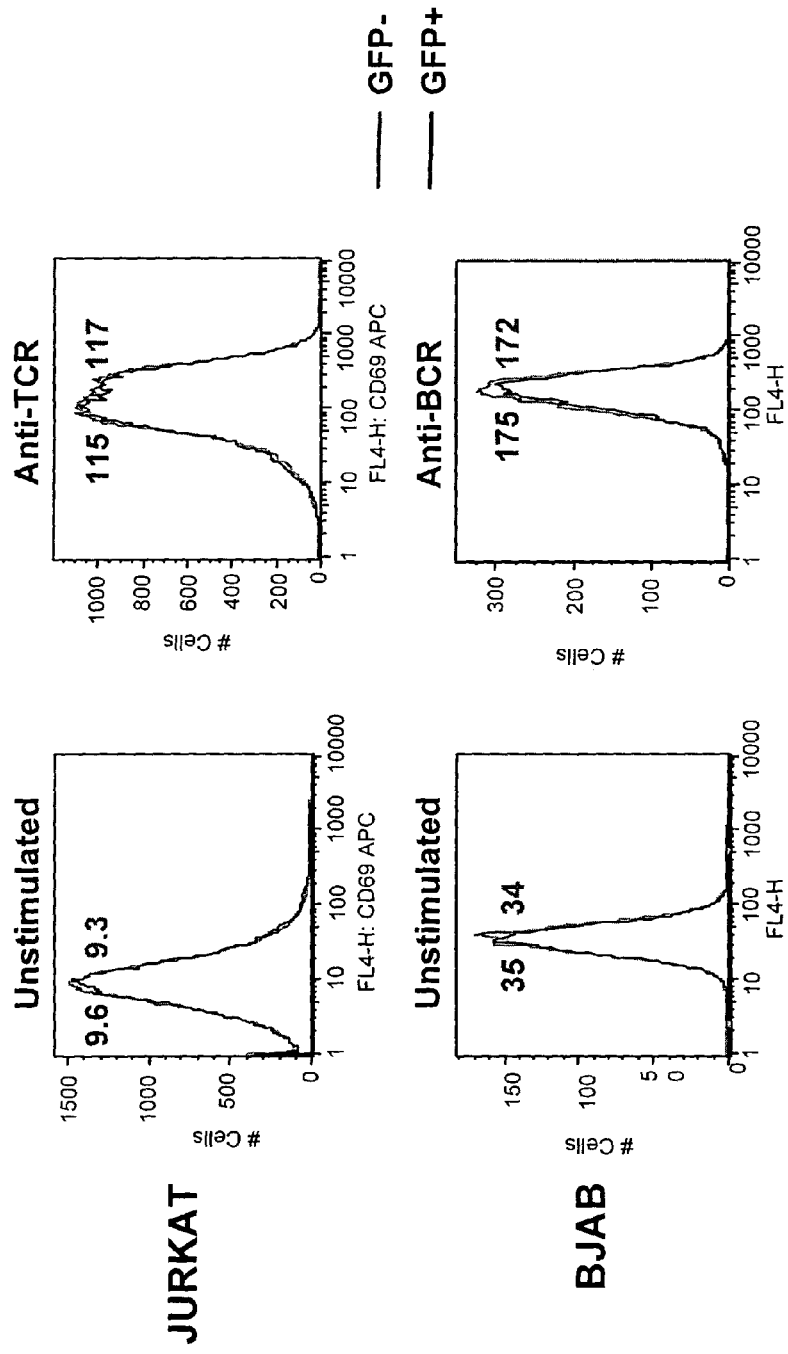
FIG. 11 shows TCR induced CD69 upregulation: IRES-GFP vector control.
Figure 12:
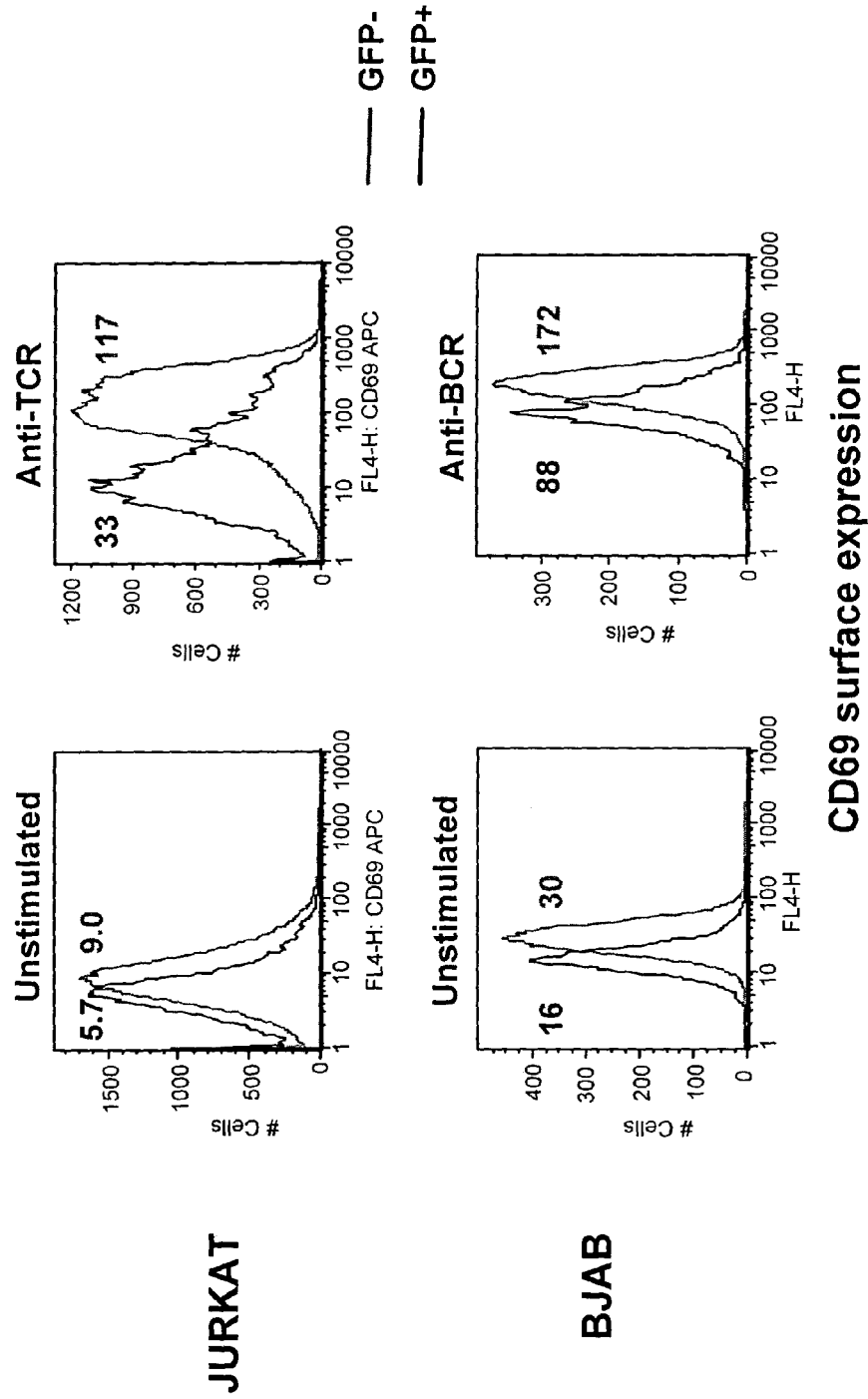
FIG. 12 shows that dn-syk inhibits both TCR and BCR signaling.
Figure 15:
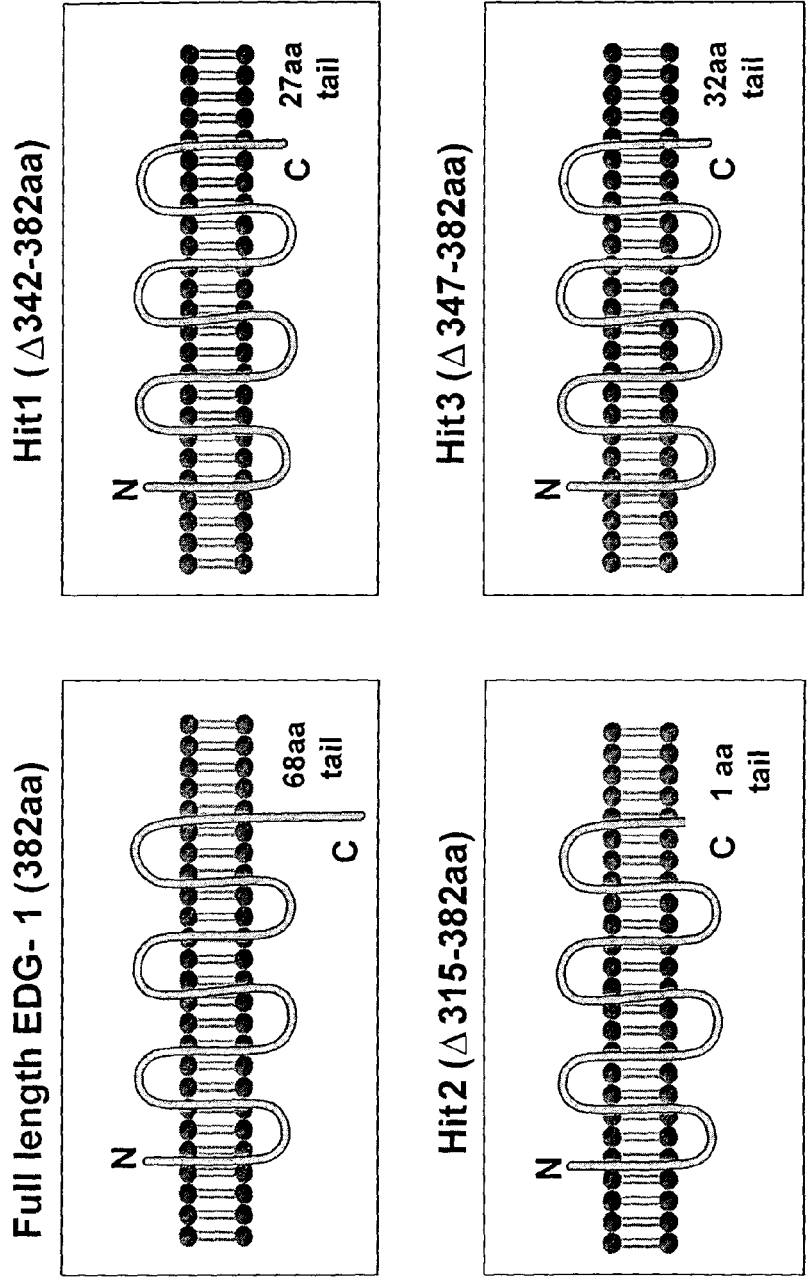
FIG. 15 shows a schematic of EDG-1 and C-terminally truncated variants.
Figure 16:
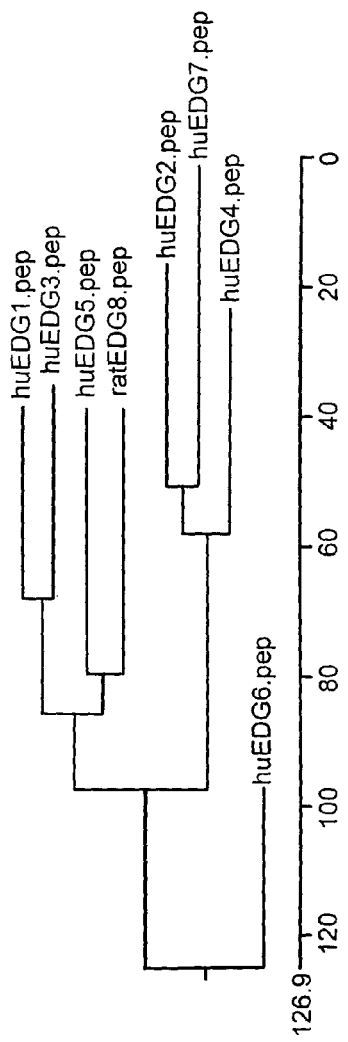
FIG. 16 shows a dendogram of EDG family members.
Figure 17A:
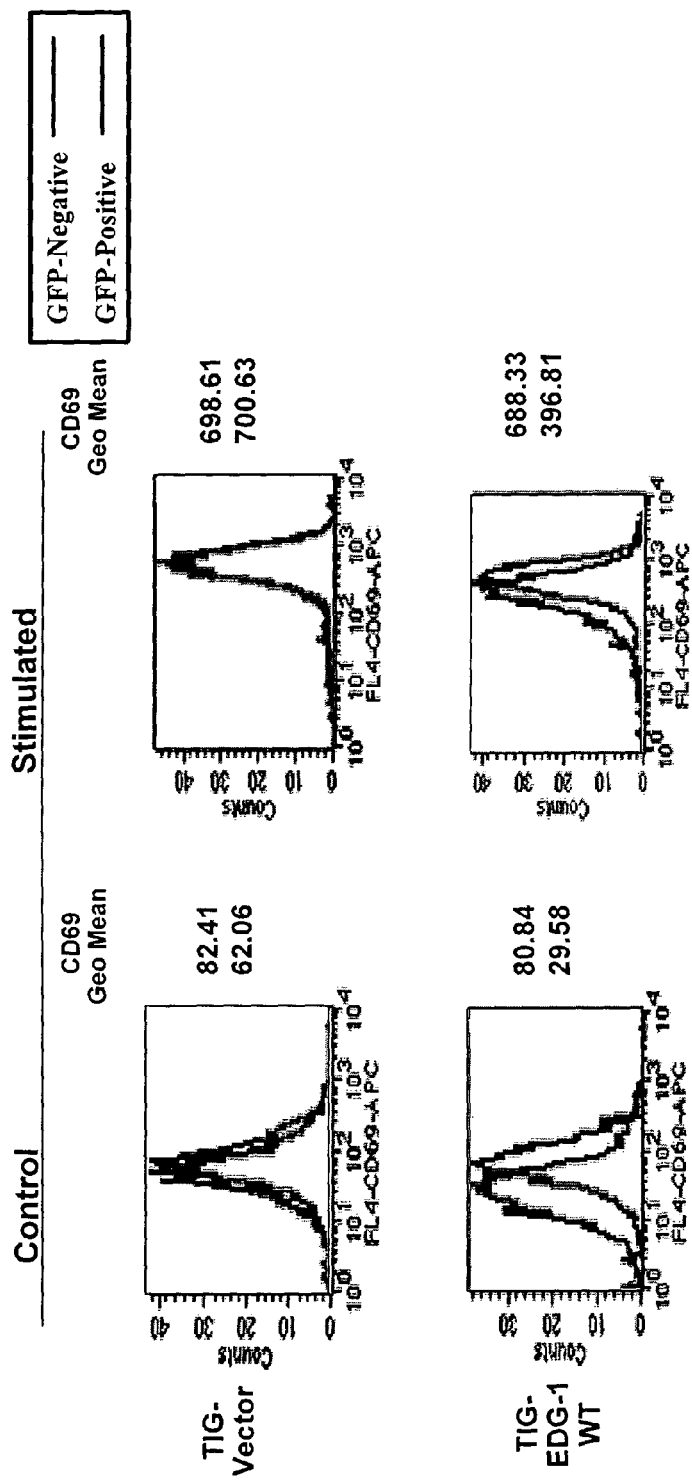
FIG. 17 shows that wild-type EDG-1 and the c-terminally truncated variants inhibit anti-BCR-induced CD69 upregulation in BJAB cells.
Figure 17B:
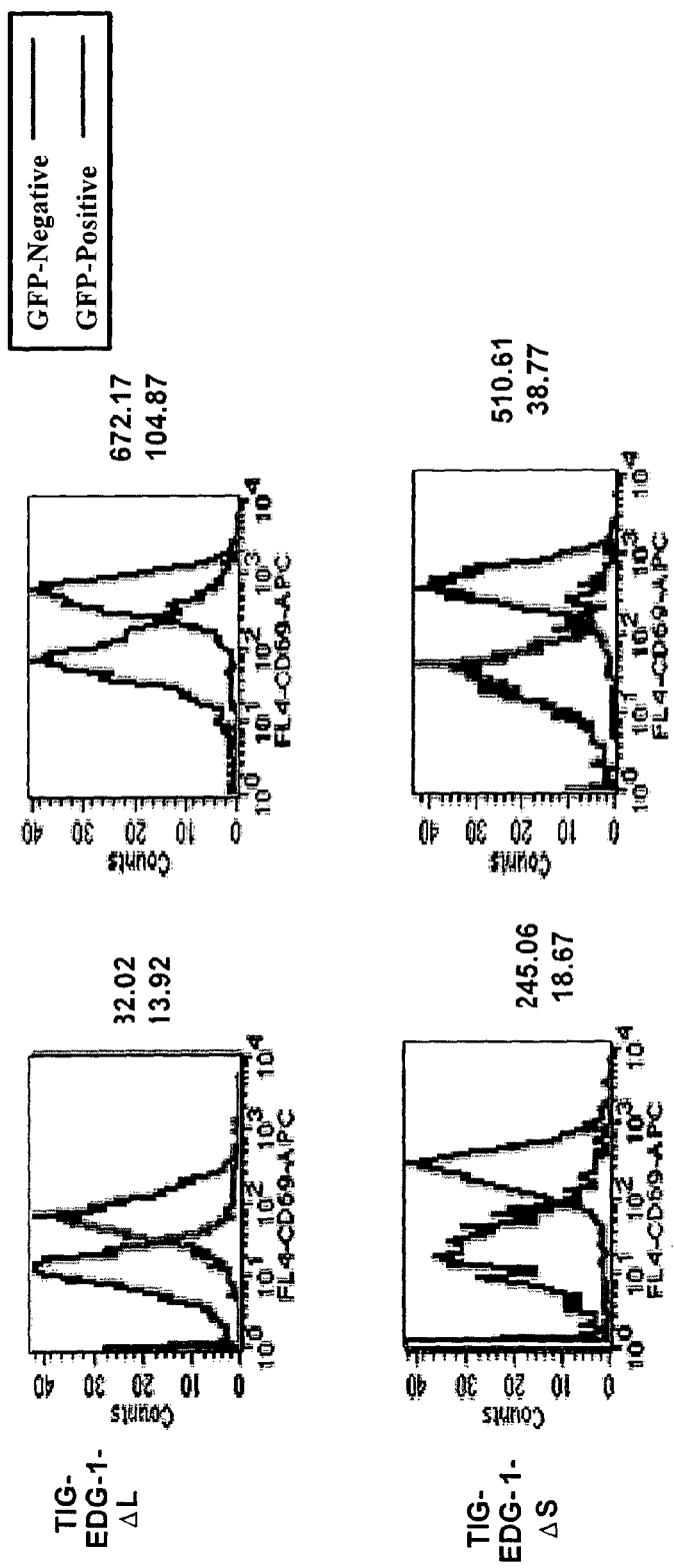
Figure 18:
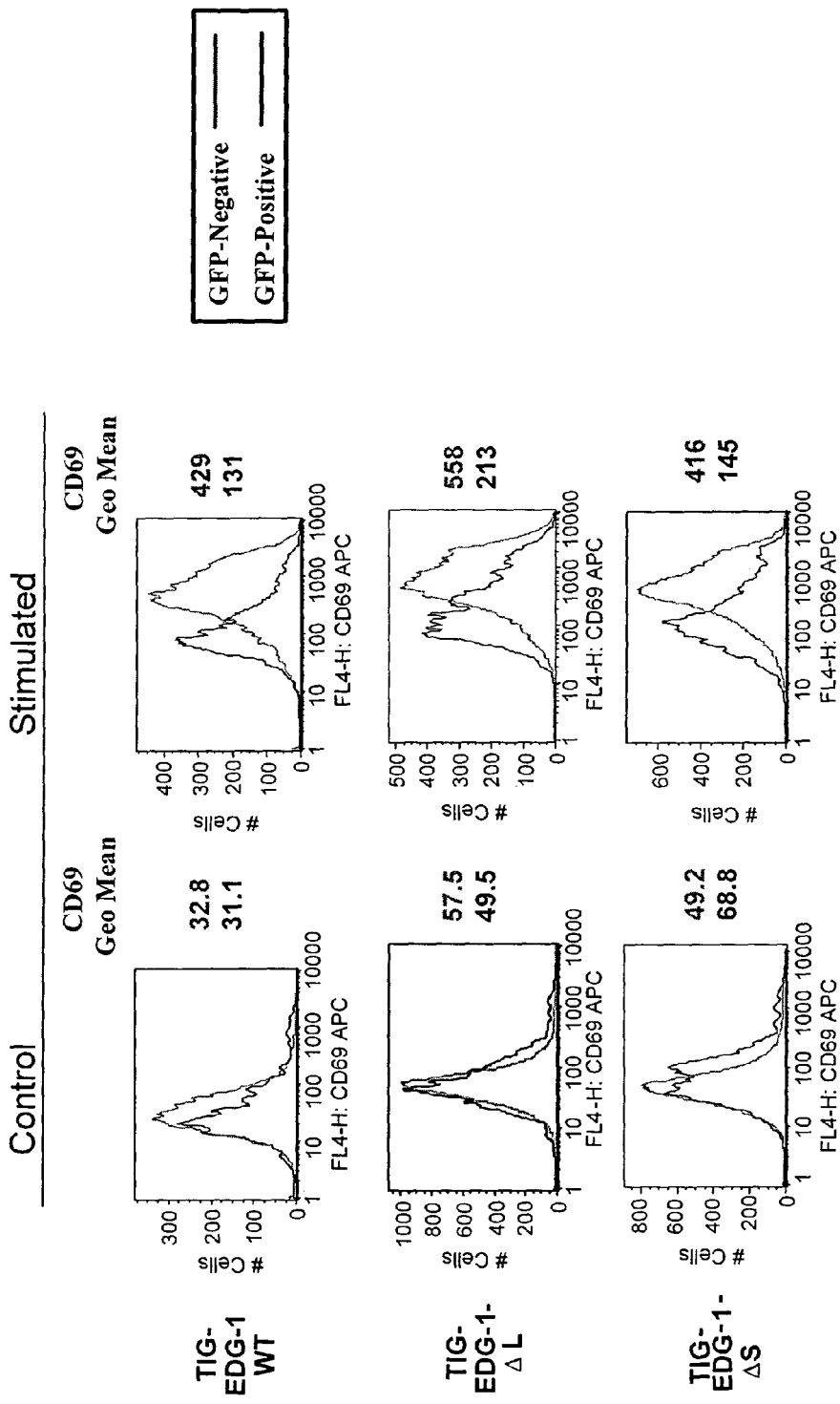
FIG. 18 shows that wild-type EDG-1 and the c-terminally truncated variants inhibit anti-TCR-induced CD69 upregulation in Jurkat cells.
Figure 19:
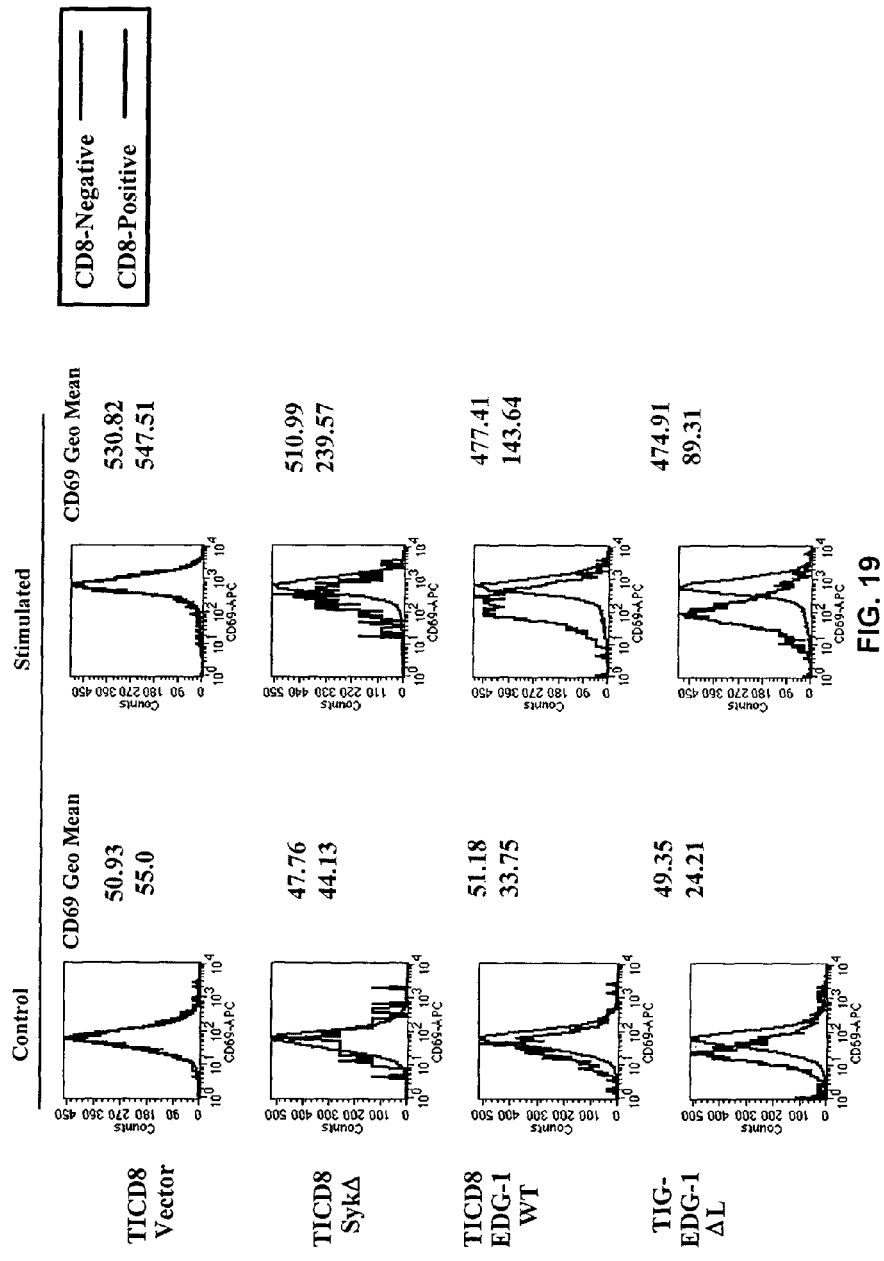
FIG. 19 shows that wild-type EDG-1 and the c-terminally truncated variants inhibit anti-BCR-induced CD69 upregulation in BJAB cells in TICD8.
Figure 20:
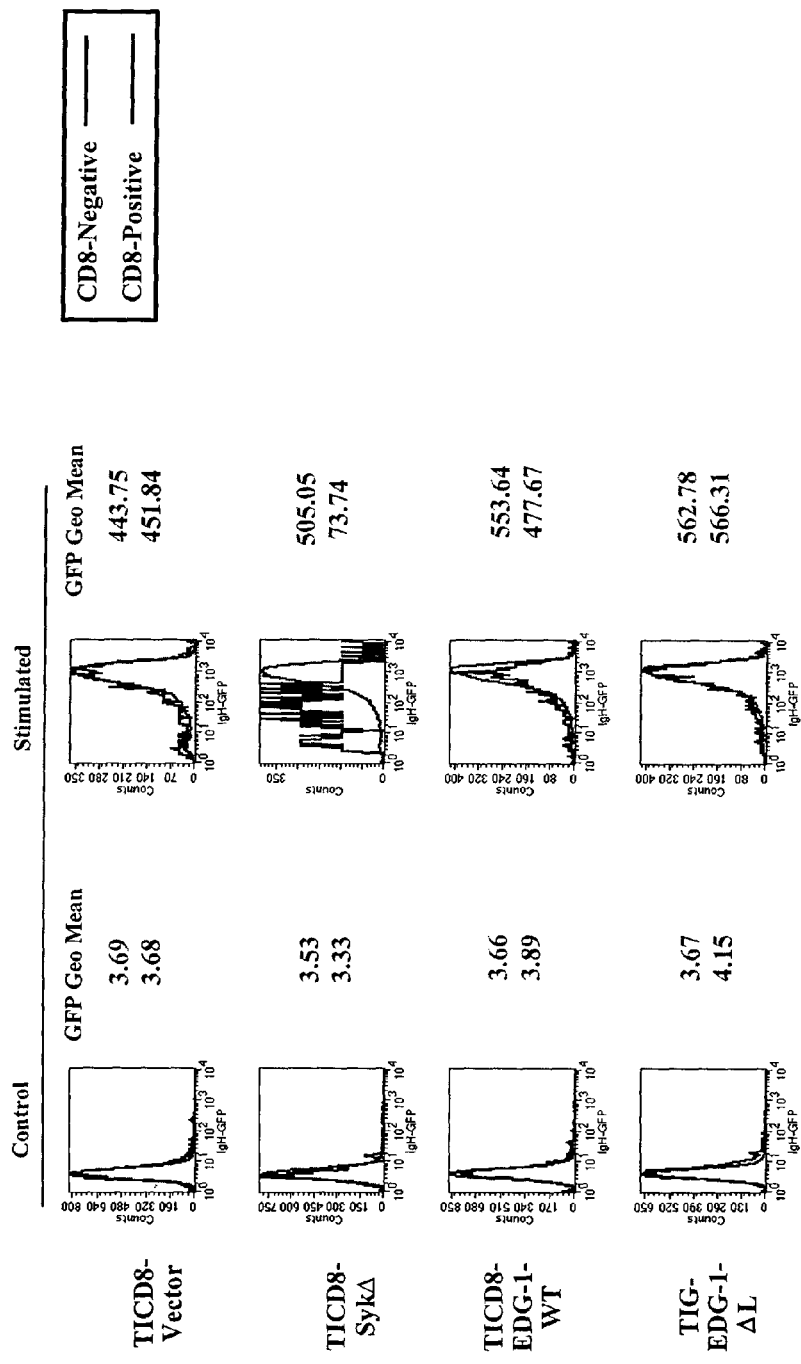
FIG. 20 shows that wild-type EDG-1 and the c-terminally truncated variants have no effect on anti-BCR-induced NFAT upregulation in BJAB/NFAT cells
Figure 21:
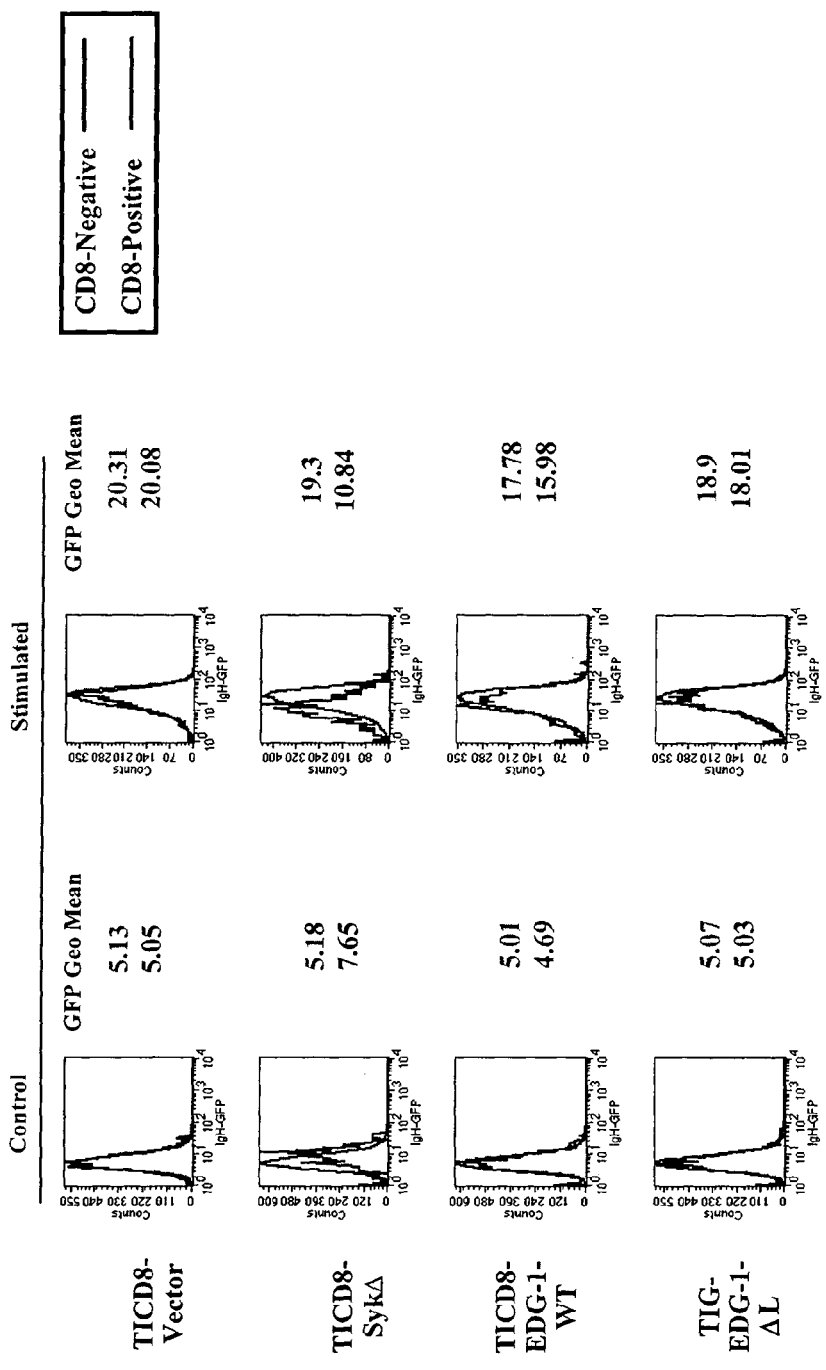
FIG. 21 shows that wild-type EDG-1 and the c-terminally truncated variants have no effect on anti-BCR-induced IgH promoter activation in BJAB/IgH cells.
Figure 22:
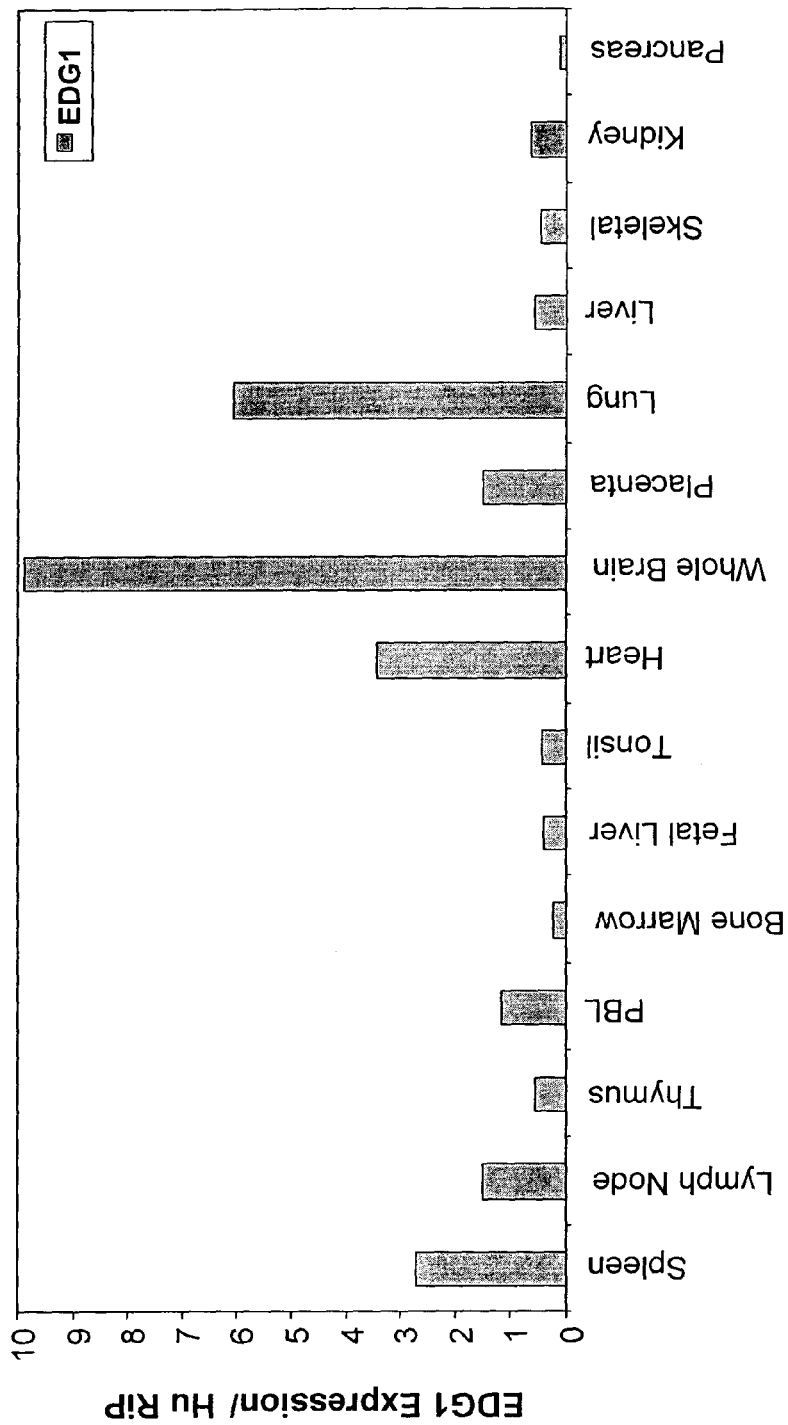
FIG. 22 shows the relative level of EDG-1 message in selected human tissues.
Figure 23:
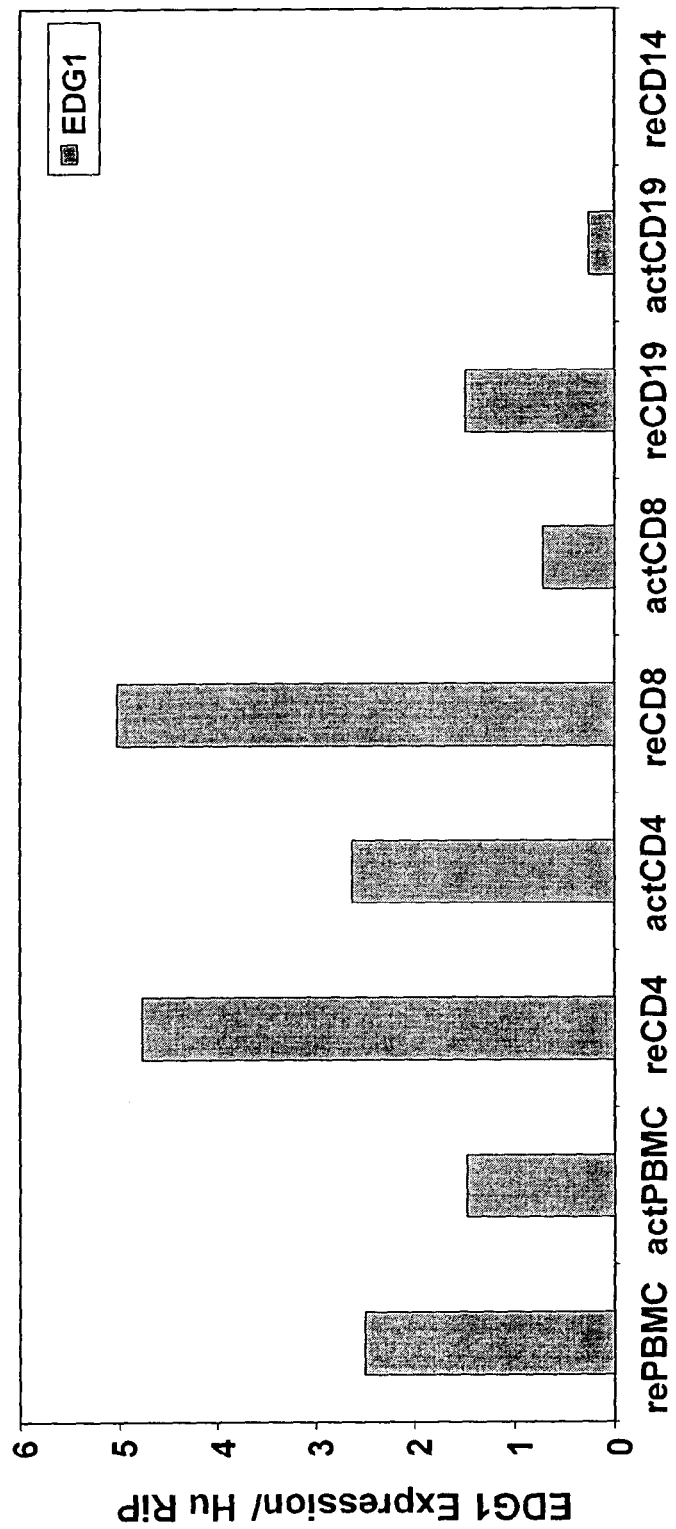
FIG. 23 shows the relative level of EDG-1 message in selected, purified human cells.
Figure 24:
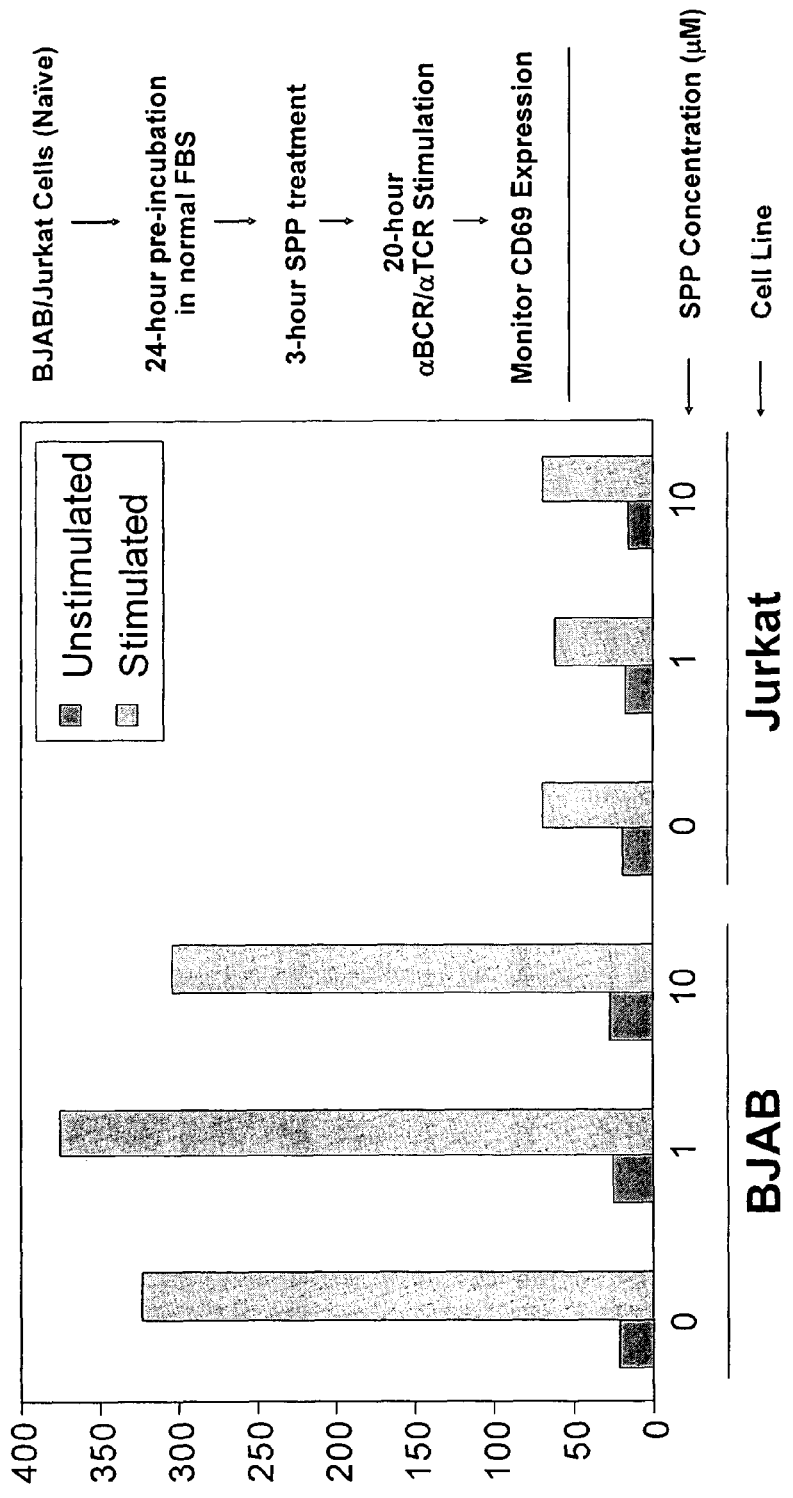
FIG. 24 shows that in regular serum, SPP has no effect on anti-BCR/TCR-induced CD69 upregulation in naive BJAB and Jurkat cells.
Figure 25:
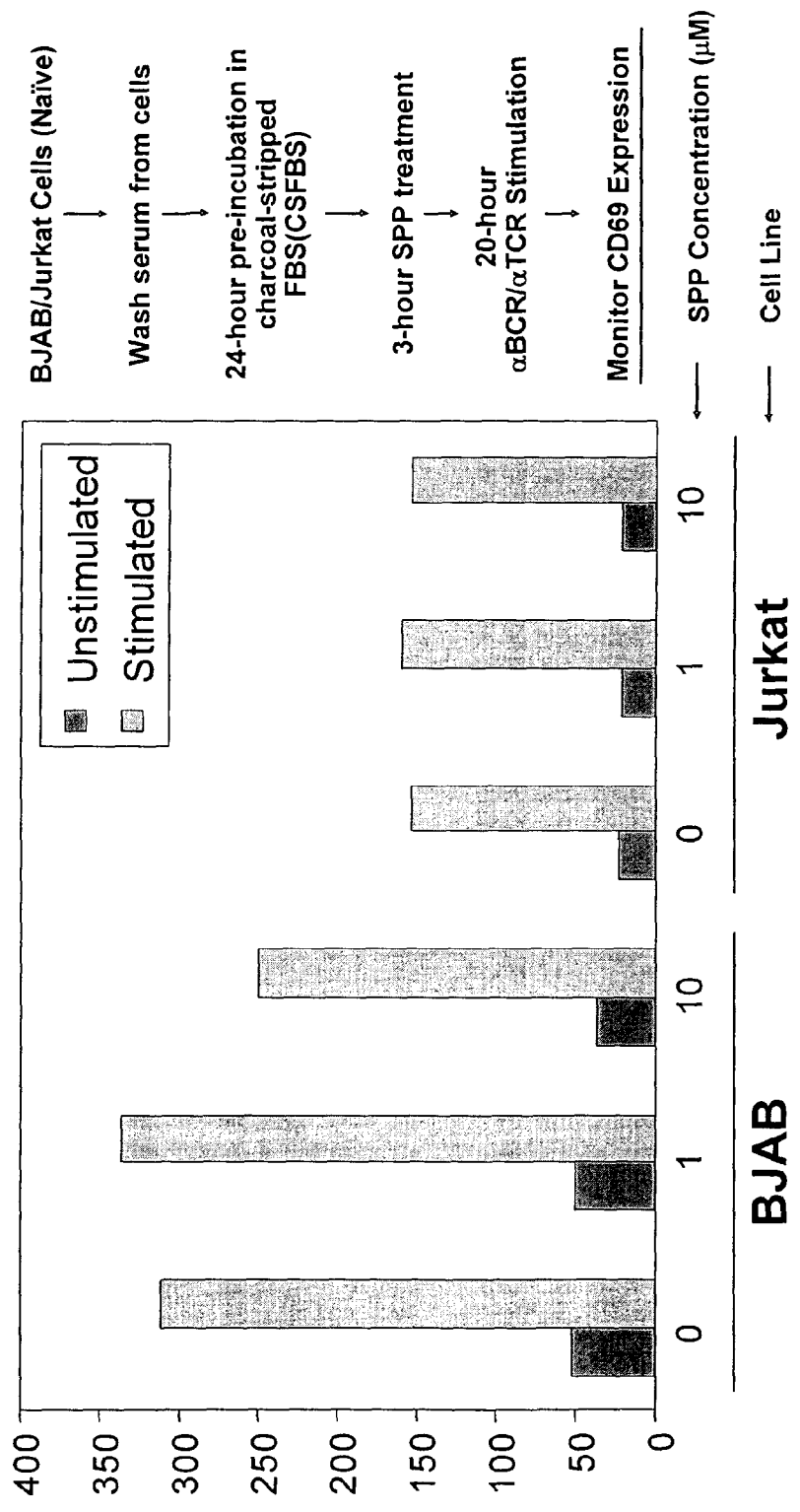
FIG. 25 shows that SPP has no effect on anti-BCR/TCR-induced CD69 upregulation in naïve BJAB and Jurkat cells in the presence of CS-FBS.
Figure 26:
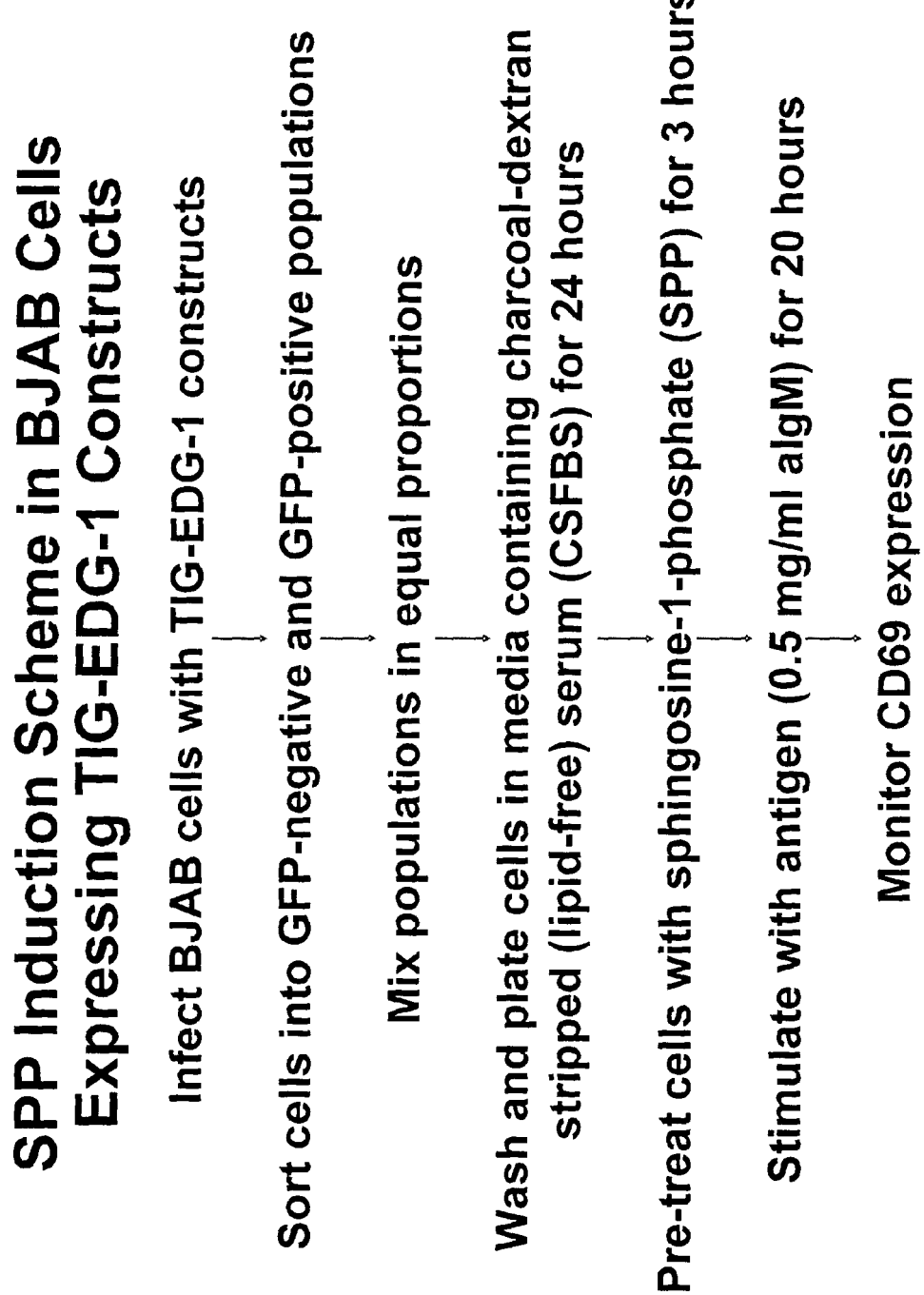
FIG. 26 shows a schematic of SPP induction in BJAB cells expressing TIG-EDG-1 constructs.
Figure 27:
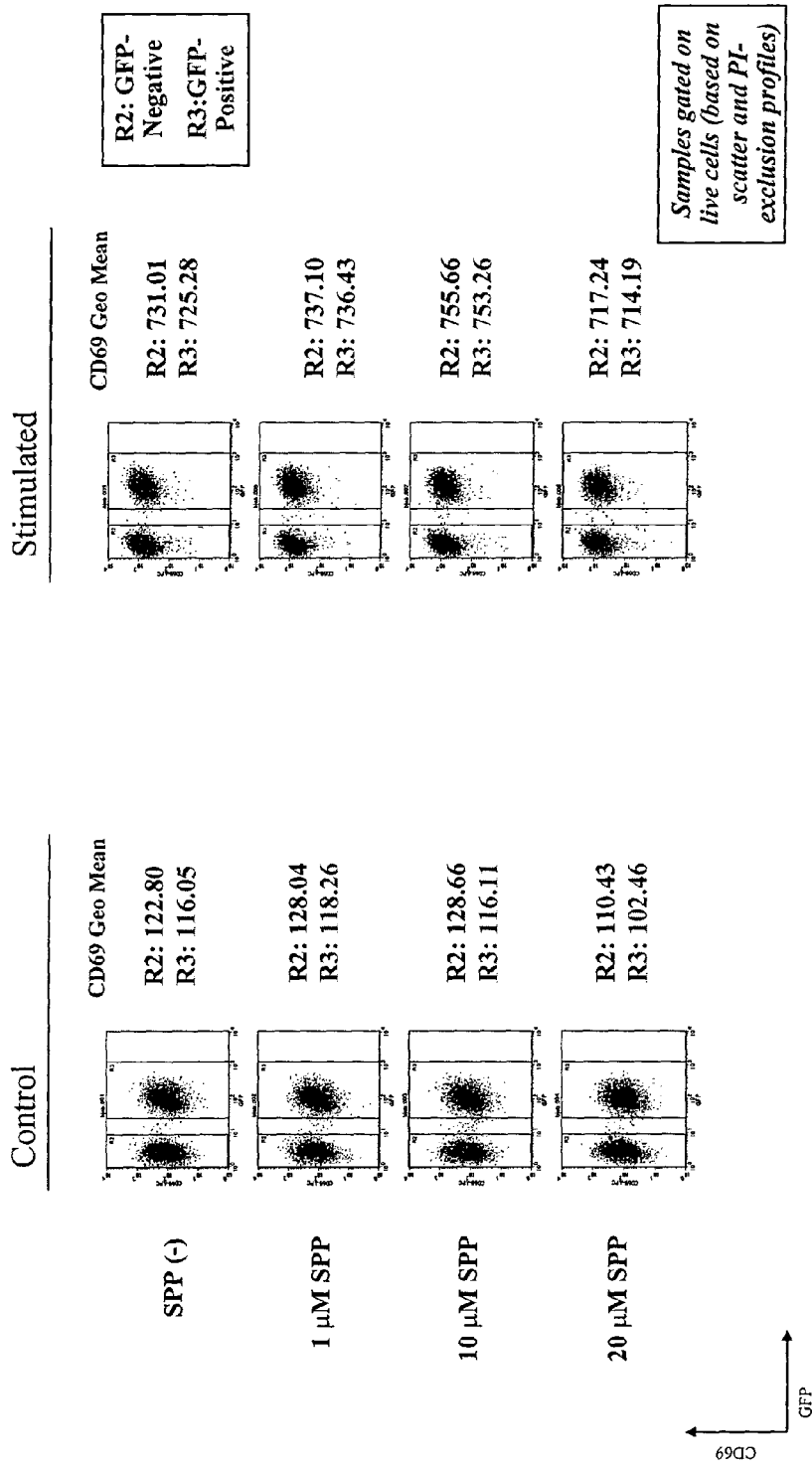
FIG. 27 shows that SPP has no effect on anti-BCR induced CD69 upregulation in BJAB cells expressing TIG vector.
Figure 28:
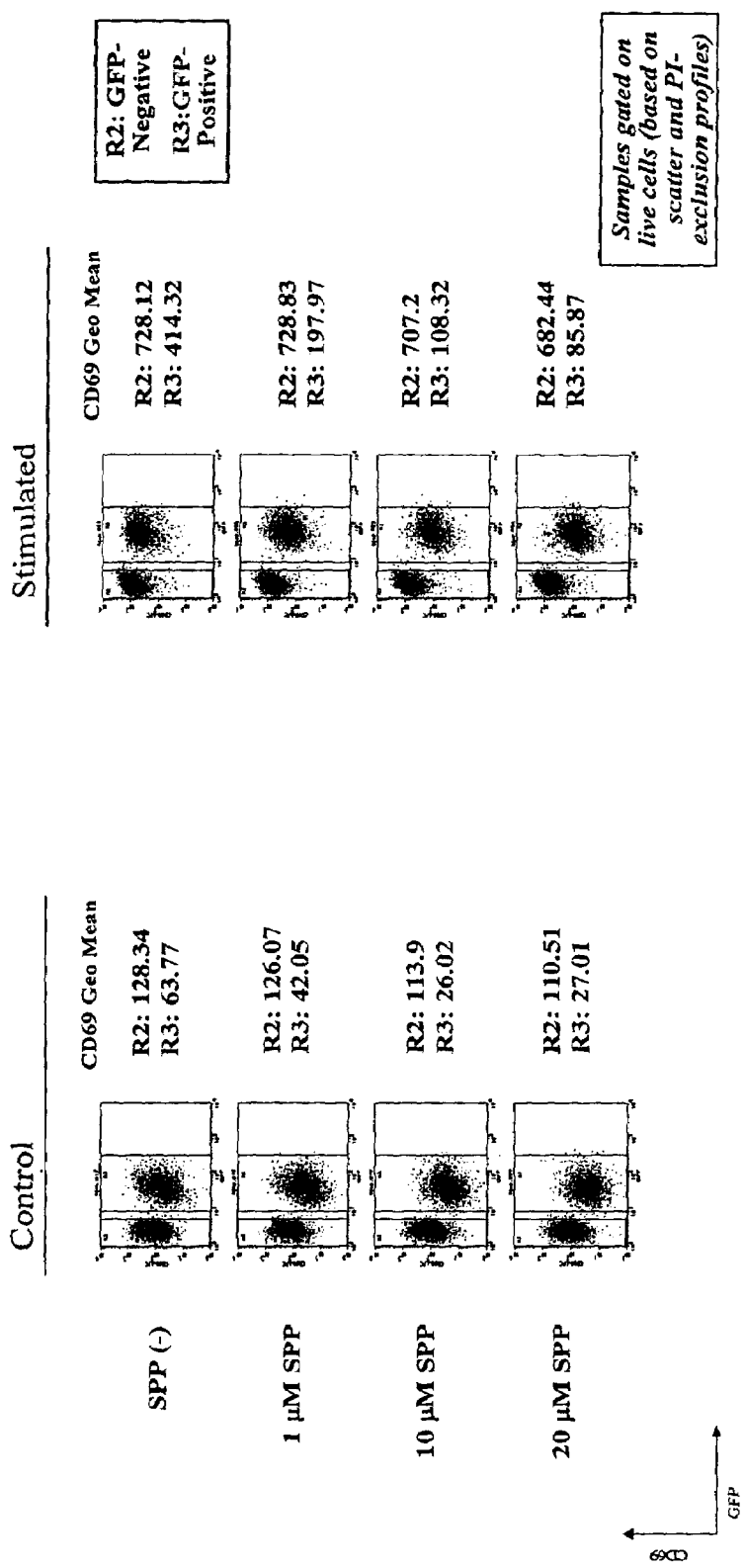
FIG. 28 shows that SPP potentiates wild-type EDG-1 inhibition of anti-BCR induced CD69 upregulation in BJAB cells.
Figure 29:
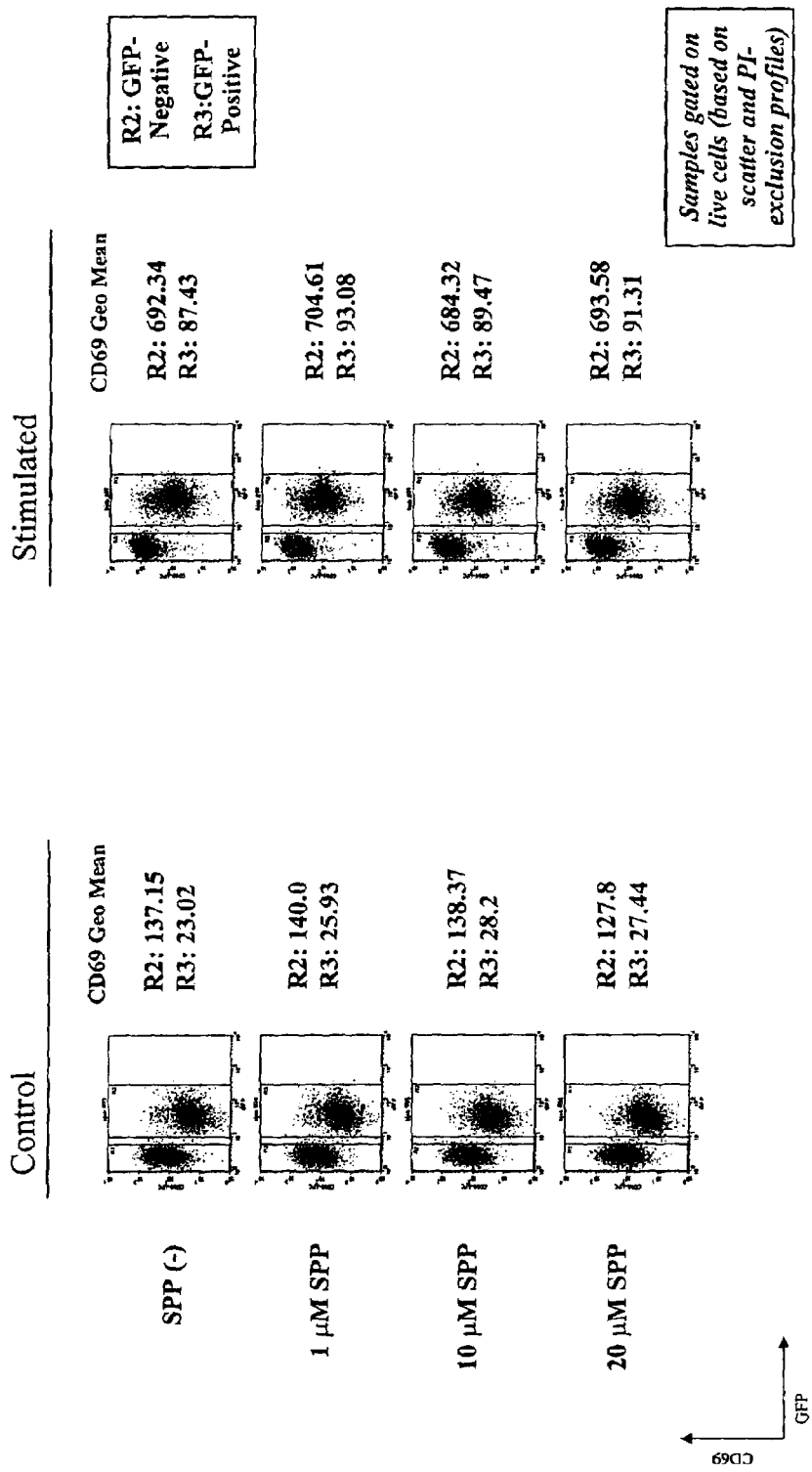
FIGS. 29 and 30 show that SPP has no effect on the inhibition of EDG-1 mediated anti-BCR induced CD69 upregulation in BJAB cells.
Figure 30:
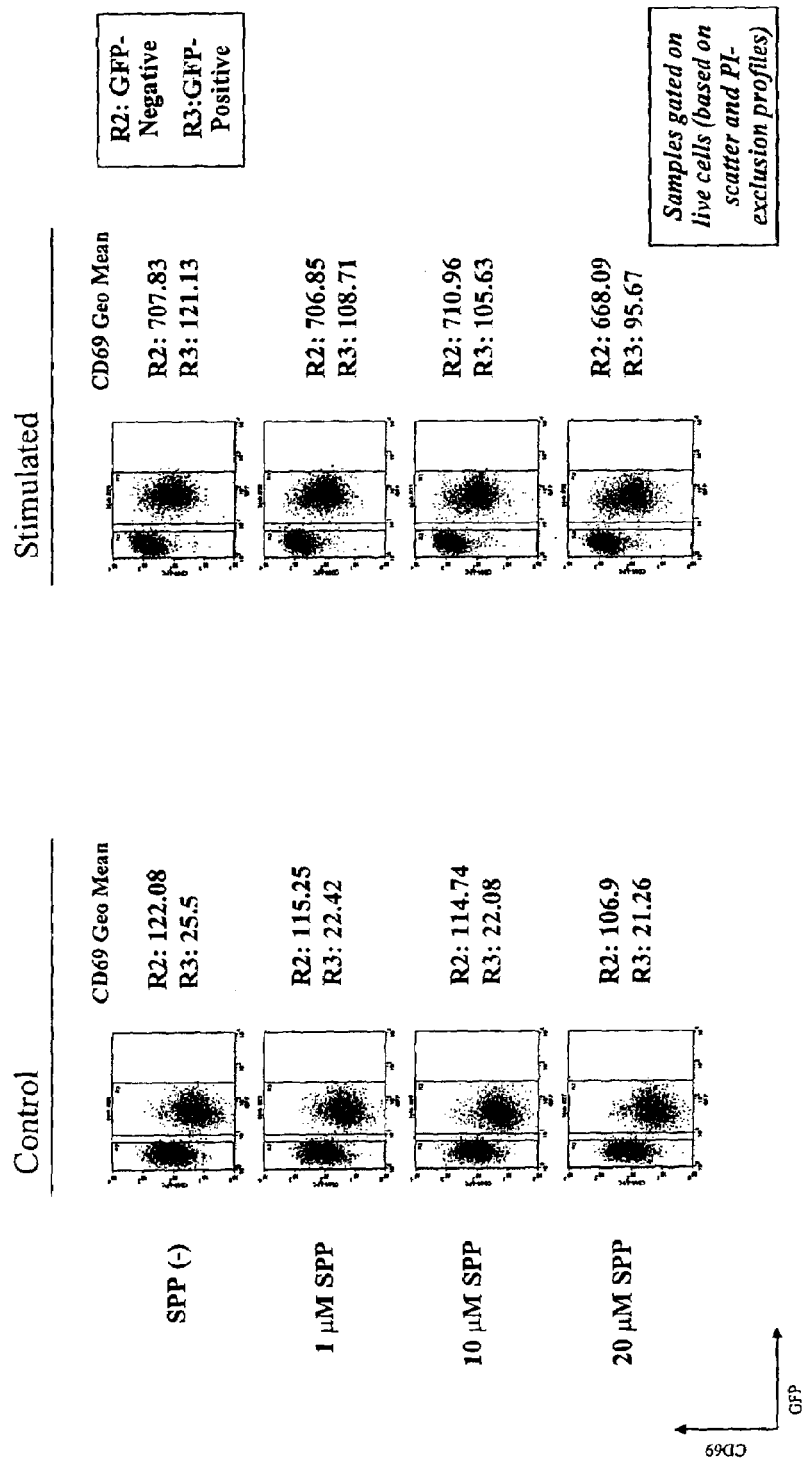
Figure 31:
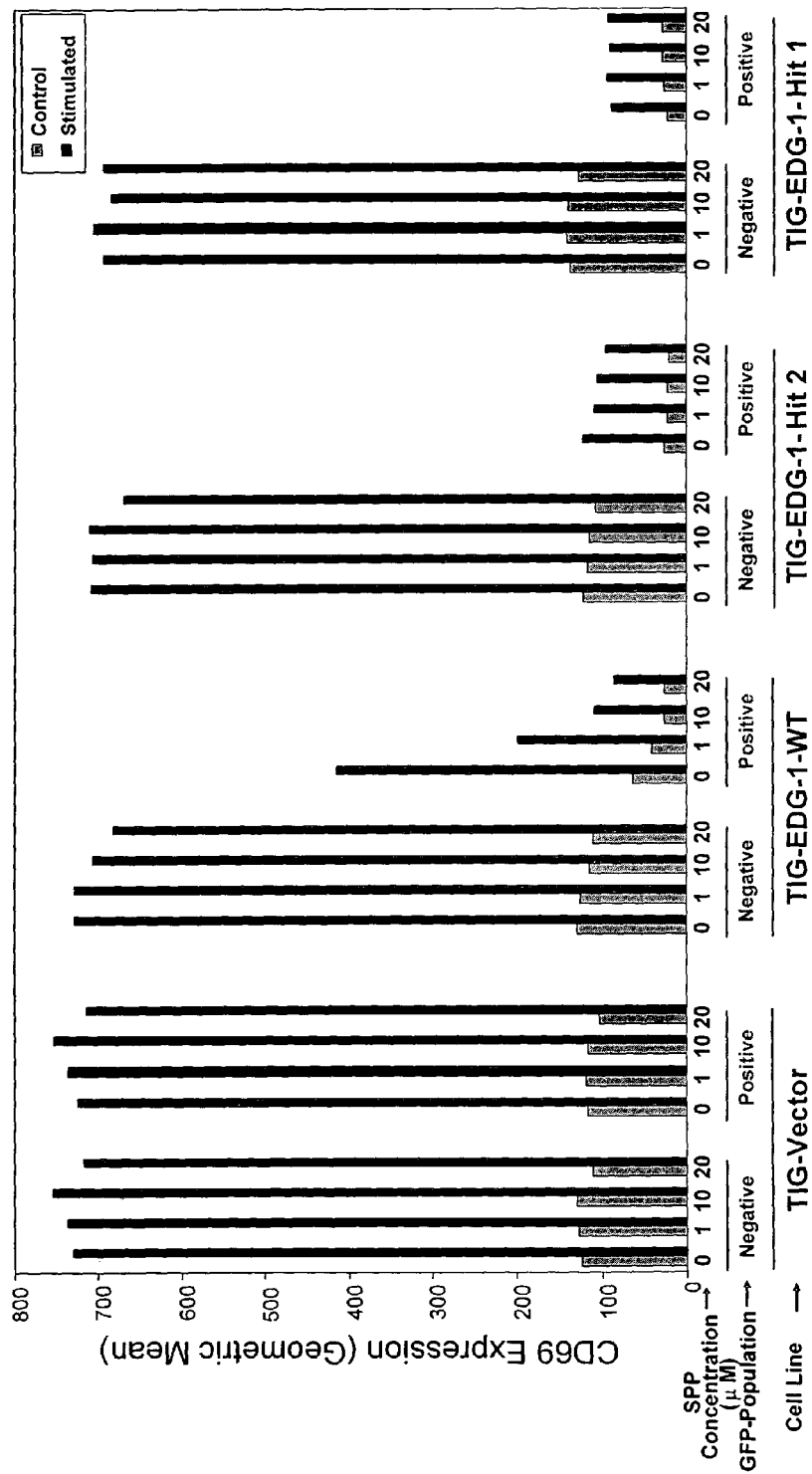
FIG. 31 shows a summary of SPP effect on wild-type EDG-1 and the c-truncated variants in BJAB cells.
Figure 32:
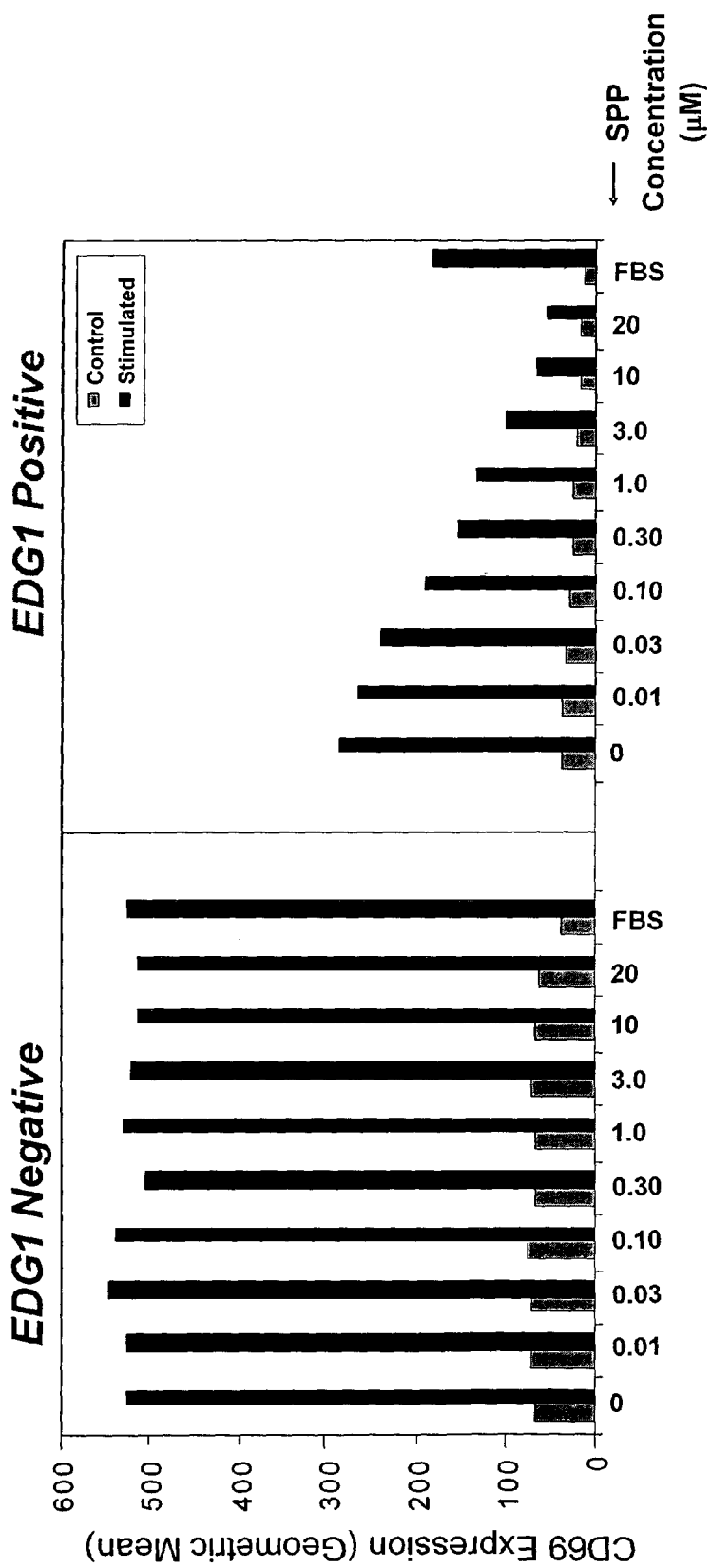
FIG. 32 shows that wild-type EDG-1 inhibits anti-BCR induced CD69 upregulation in an SPP dose-dependent manner.

For the first time, a protein from the EDG G-protein coupled receptor (GPCR) family has been functionally identified as a protein involved in regulating lymphocyte activation and migration. EDG-1 was identified in a functional genetic screen using CD 69 as a readout of lymphocyte activation. Truncated forms of nucleic acids encoding C-terminally truncated variants of EDG-1 (SEQ ID NOS:2-4) were recovered as inhibitors of lymphocyte activation-induced CD69 expression. Wild type EDG-1 was also found to inhibit T cell activation-induced CD69 expression. EDG-1 expression also inhibited IL-2 production in human primary lymphocytes. In the absence of SPP, a ligand for wild-type EDG-1, truncated forms of EDG-1 inhibited B cell activation-induced CD69 upregulation, while wild-type EDG-1 had a similar but weaker effect. However, when SPP was added to the overexpressing wild-type EDG-1, the wild type EDG-1 inhibited B cell activation-induced CD69 expression in a dose dependent manner. These results indicate that EDG-1, other EDG family members such as EDG 8, and EDG family modulators, e.g., agonists or agonists, can be used for inhibition or activation of TCR and BCR signaling and lymphocyte activation. In one embodiment, modulators of EDG family proteins are used to inhibit lymphocyte activation. In one embodiment, agonists of EDG-1 are used for inhibition of lymphocyte activation.

In addition, EDG-1 mediates SPP-induced lymphocyte migration, which is blocked by 2-amino-2(2-[4-octylphenyl] ethyl)-1,3-propanediol hydrochloride (FTY720). The mutant EDG-1 protein lacking amino acids 315-382 (only one remaining amino acid of the C-terminal cytoplasmic tail) does not mediate ligand-induced migration, demonstrating that the C-terminal tail of EDG-1 is required for SPP-induced migration. EDG-5 blocks SPP mediated migration. These results indicate that EDG-1, other EDG family members such as EDG-5, and EDG modulators, e.g., antagonists or agonists, can be used for inhibition or activation of lymphocyte migration. In one embodiment, modulators of EDG family proteins are used to inhibit lymphocyte migration. In one embodiment, antagonists of EDG-1 are used for inhibition of lymphocyte migration.

Previously, EDG family proteins were known to be G-protein coupled receptors (GPCR, see, e.g., WO 94/05695 and U.S. Pat. No. 5,508,384) that are expressed in a wide variety of cells (see, e.g., Goetzl et al., J. Immunol. 164:4669-4999 (2000)). However, the function of EDG proteins was unknown. EDG-1 was identified as expressed in endothelial cells as well as in many other cells, and a role in angiogenesis has been proposed for this protein (see, e.g., WO 91/15583; Bornfeldt et al., J. Cell Biol. 130:193-206 (1995); and Wang et al., J. Biol. Chem. 274:35343-35350 (1999)). It has also been speculated that EDG-1 is involved in numerous diverse disease states (see, e.g., WO 99/46277). EDG-1 is ubiquitously expressed. EDG-4 has been identified as expressed in T lymphocytes, among other cells (see, e.g., Goetzl et al., J. Immunol. 164:4669-4999 (2000)). A role for EDG-2 and other EDG family members in apoptosis, e.g., in lymphocytes, has also been proposed (see, e.g., WO 99/19513).

EDG-1 and other EDG family members EDG-2 to -8 were known to bind sphingolipid ligands, e.g., sphingosine-1-phosphate (SPP, EDG-1, 3, 5, 6, and 8) or lysophosphatidic acid (LPA), EDG-2, 4, and 7) (see, e.g., Okamoto et al., *J. Biol. Chem.* 273:27104-27110 (1998); Lee et al., *Science* 279:1552-1555 (1998); Lee et al., *J. Biol. Chem.* 273:22105-22112 (1998); Pyne & Pyne, *Biochem. J.* 349:385-402 (2000); and Windh et al., *J. Biol. Chem.* 274:27351-27358 (1999); and Prieschl & Baumruker, *Immunology Today* 21:555-560 (2000)). Recent screening for immunosuppressants has re-identified myriocin, a sphingosine-like natural fungal product (Chen et al., *Chemistry & Biology* 6:221-235 (1999)). FTY720 is a synthetic analog of myriocin and has immunosuppressant activity, e.g., for organ transplant and graft vs. host disease (2-amino-2(2-[4-octylphenyl]ethyl)-1, 3-propanediol hydrochloride). Its primary molecular target, however, is unknown (see, e.g., Brinkmann et al., *TIPS* 21:49-52 (2000); Pinschewer et al., *J. Immunol* 164:5761-5770 (2000)). Although extracellular ligands SPP and LPA were known to bind to EDG proteins, the function of the EDG proteins remained unknown.

The present invention, therefore, has functionally identified EDG-1, and other EDG family members such as EDG 3, 5, 6, and 8 and EDG 2, 4, and 7 as drug targets for compounds that suppress or activate lymphocyte activation and migration, e.g., for the treatment of diseases in which modulation of the immune response is desired, e.g., for treating diseases related to lymphocyte activation and migration, such as delayed type hypersensitivity reactions; asthma; allergies; autoimmune diseases such as scleroderma, pernicious anemia, multiple sclerosis, myasthenia gravis, IDDM, rheumatoid arthritis, systemic lupus erythematosus, and Crohn's disease; and conditions related to organ and tissue transplant, such as graft vs. host disease; and acute and chronic inflammation; as well as in diseases in which activation of the immune response and stimulation of lymphocyte migration is desired, e.g., in immunocompromised subjects, e.g., due to HIV infection or cancer; and in infectious disease caused by viral, fungal, protozoal, and bacterial infections. Preferably, EDG-1, 3, 5, 6, 7, and 8 are used as drug targets for compounds that activate or inhibit T cell activation and migration.

Definitions

By "disorder associated with lymphocyte activation or migration" or "disease associated with lymphocyte activation or migration" herein is meant a disease state which is marked by either an excess or a deficit of B or T cell activation or migration. For example, lymphocyte activation disorders associated with increased activation or migration include, but are not limited to, acute and chronic inflammation, asthma, allergies, autoimmune disease and transplant rejection. Pathological states for which it may be desirable to increase lymphocyte activation or migration include HIV infection that results in immunocompromise, cancer, and infectious disease such as viral, fungal, protozoal, and bacterial infections. Different compounds may be used to modulate lymphocyte activation and migration, or the same compound may be used to modulate lymphocyte activation and migration.

Figure 33A:
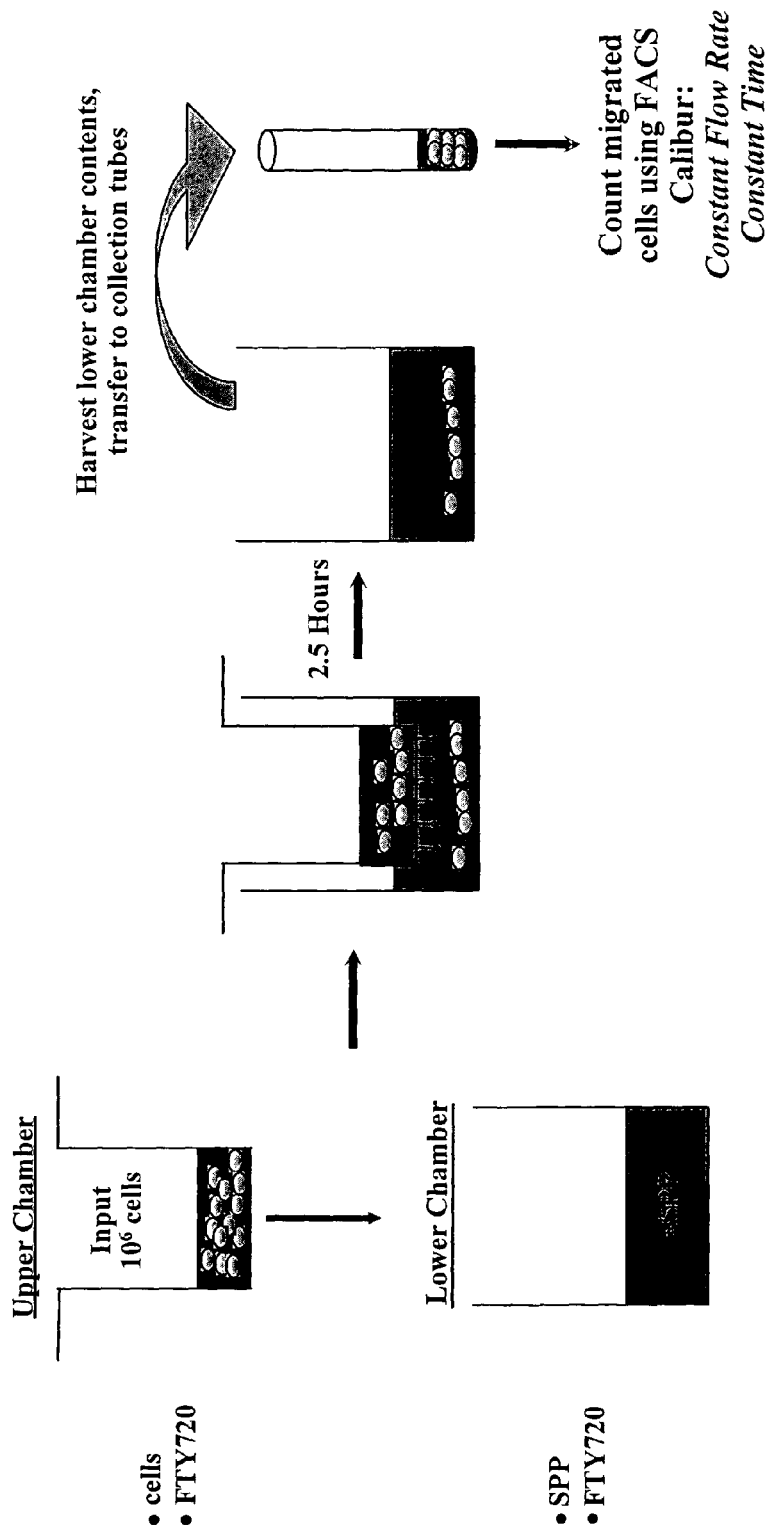
FIG. 33A shows a migration assay in Jurkat cells.
Figure 33B:
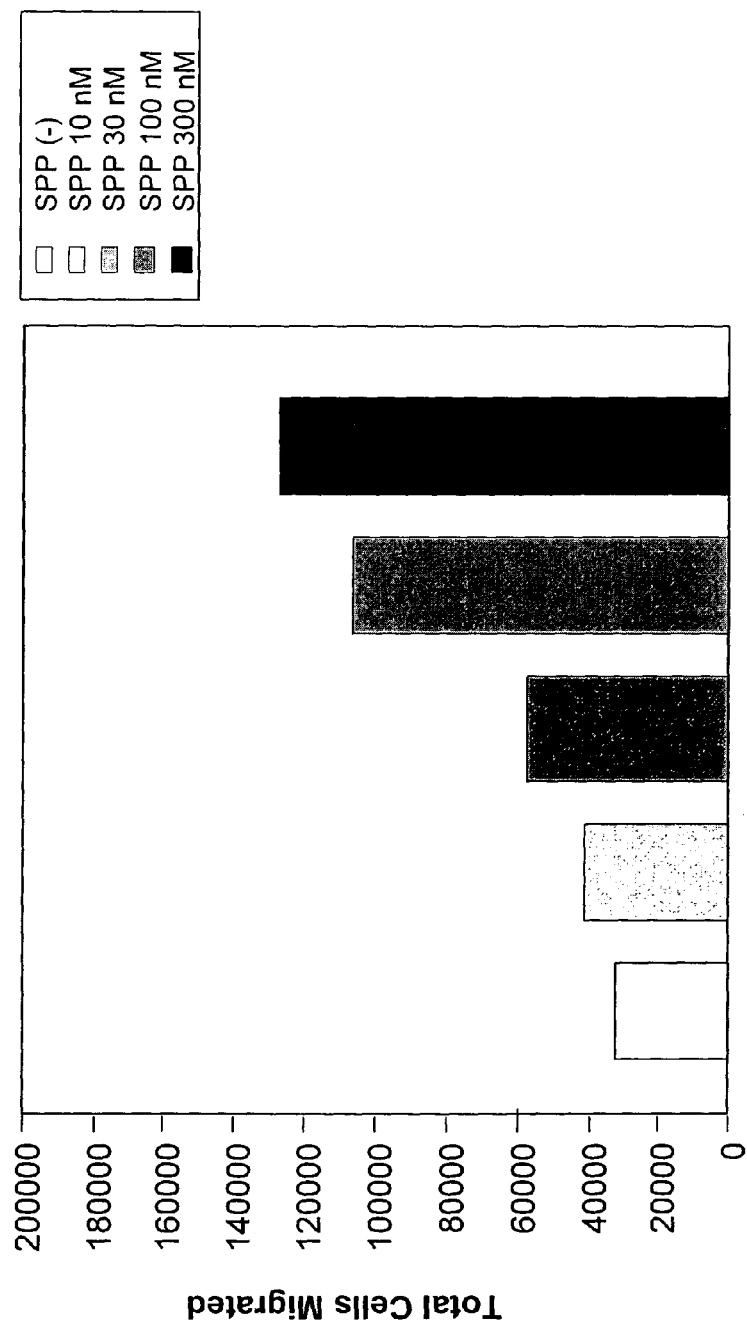
FIG. 33B shows SPP-induced migration of Jurkat cells.
Figure 34A:
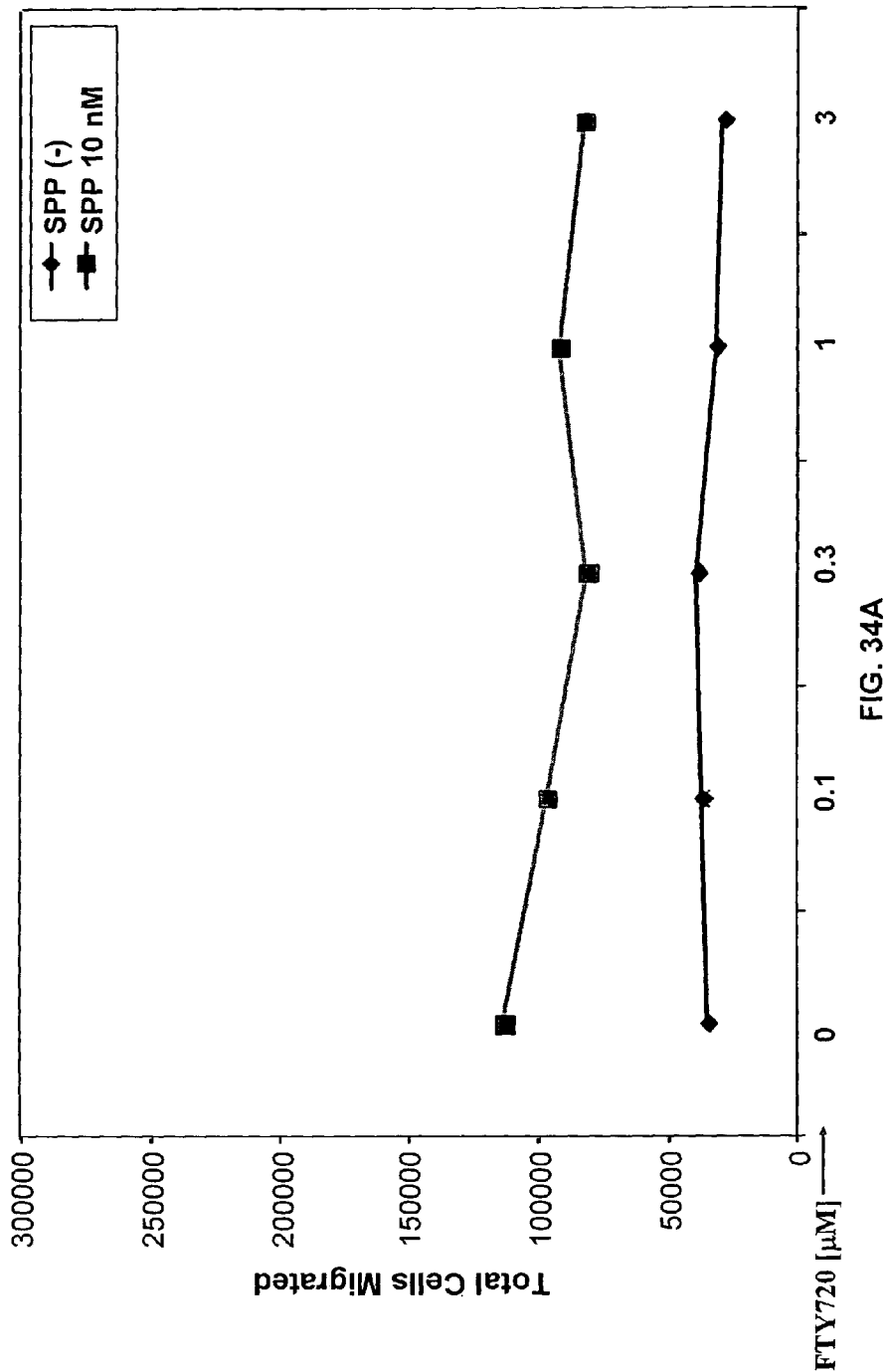
FIG. 34A demonstrates that FTY720 has no effect on SPP-induced migration in Jurkat cells.
Figure 34B:
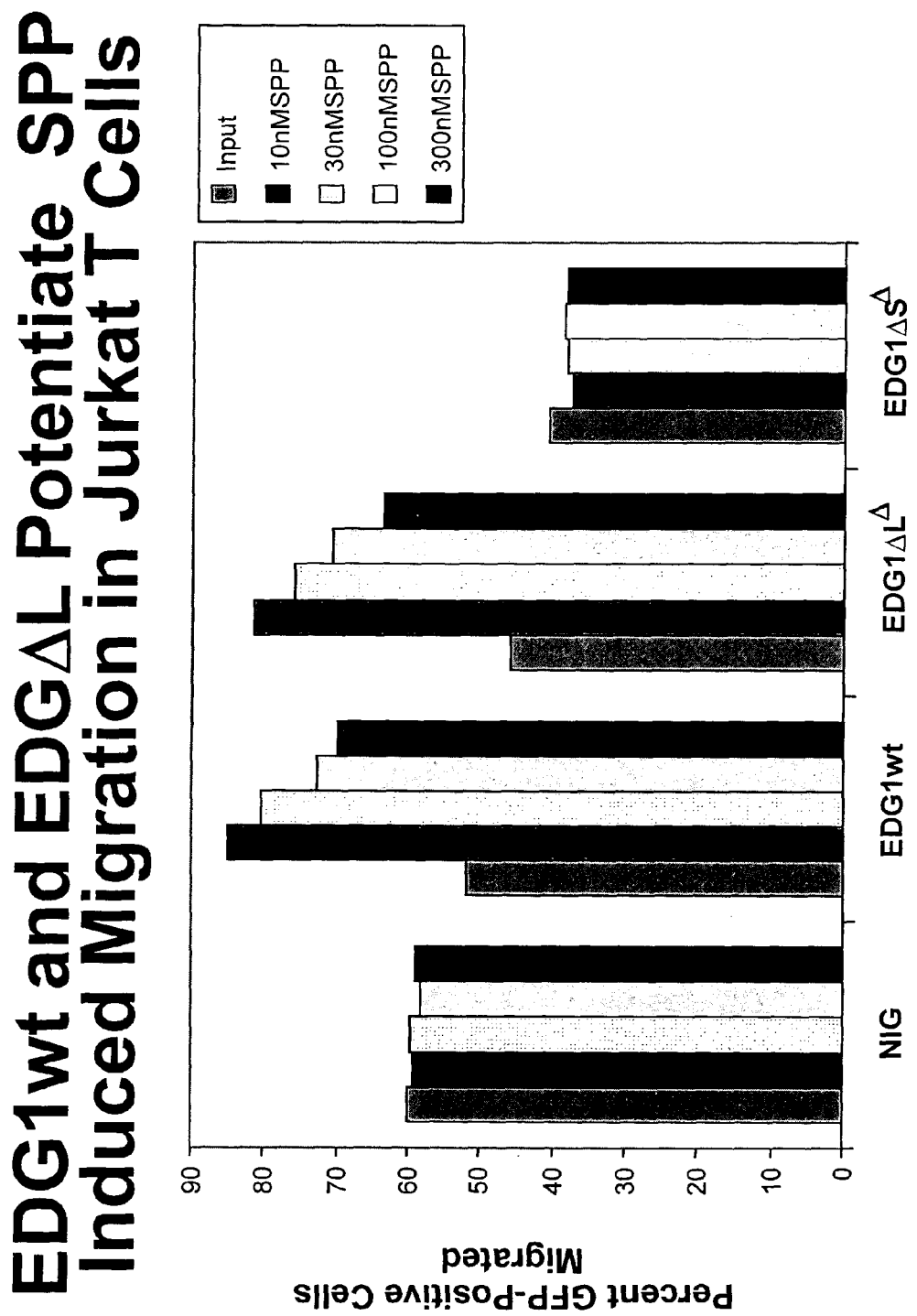
FIG. 34B demonstrates that EDG-1 wild-type and EDG-1ΔL potentiates SPP induced migration in Jurkat cells.
Figure 35:
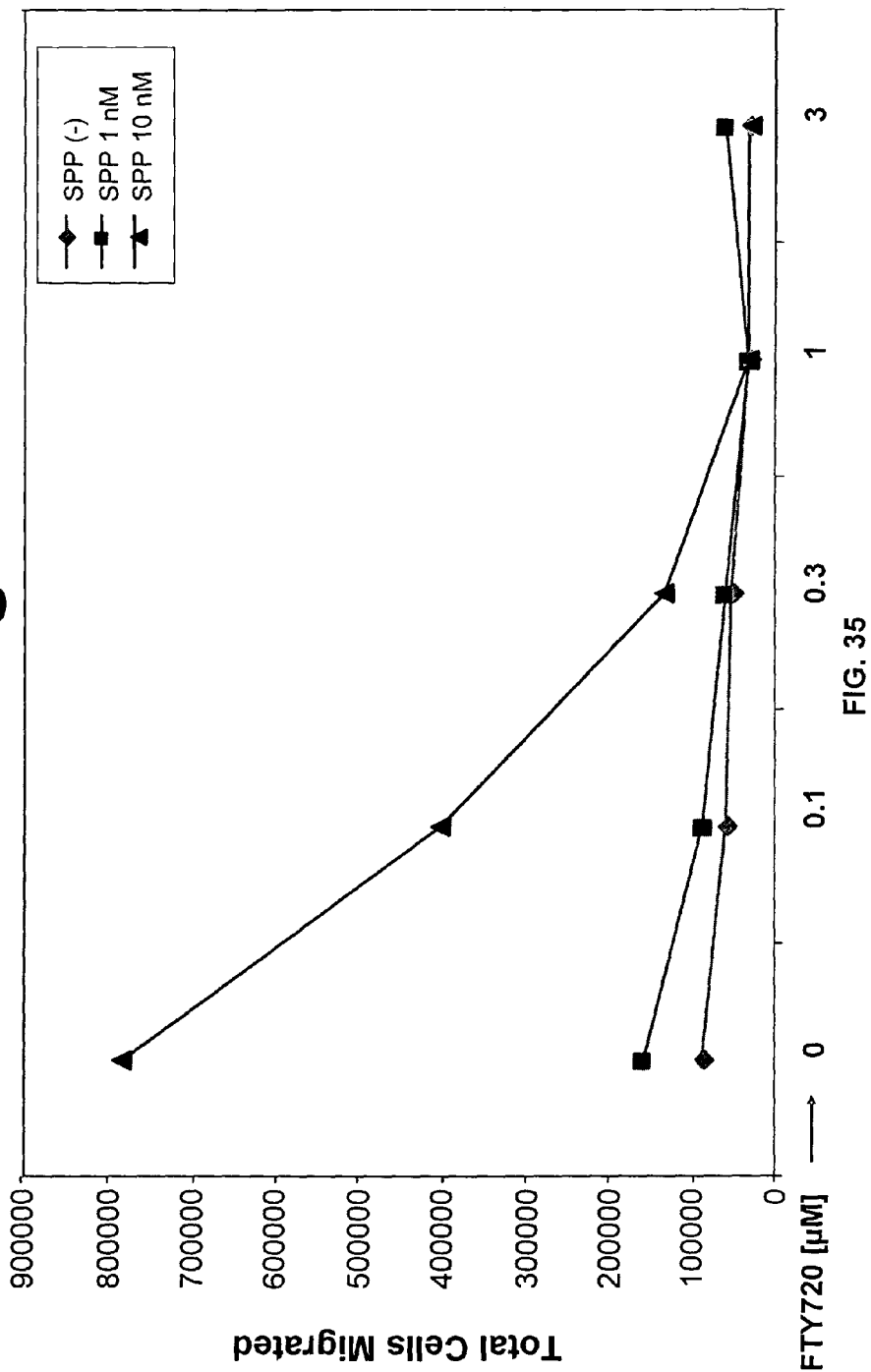
FIG. 35 demonstrates that FTY720 inhibits SPP-induced primary T cell migration.
Figure 36A:
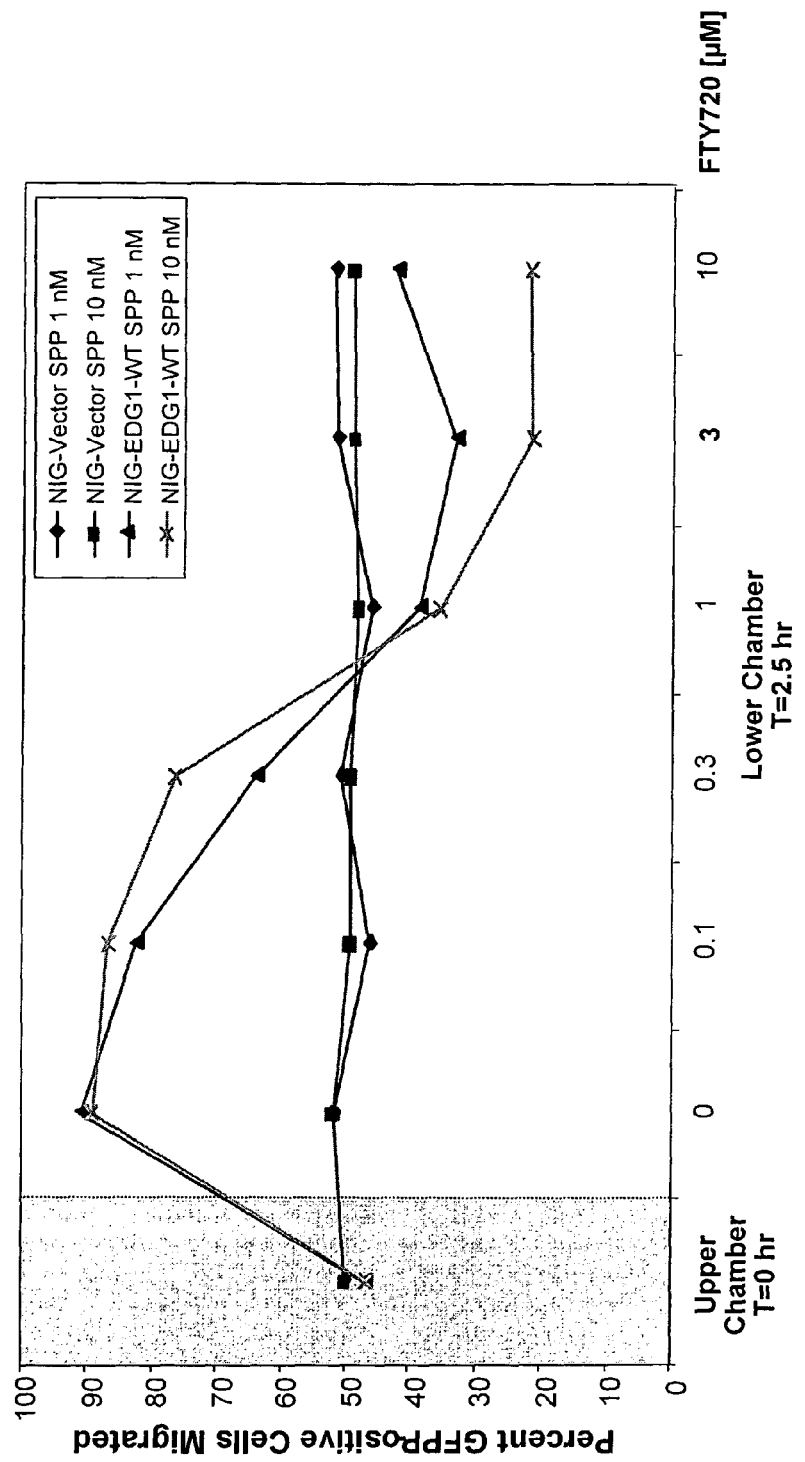
FIG. 36A shows that FTY720 inhibits EDG-1 wild-type enhanced SPP-induced migration in Jurkat cells.
Figure 36B:
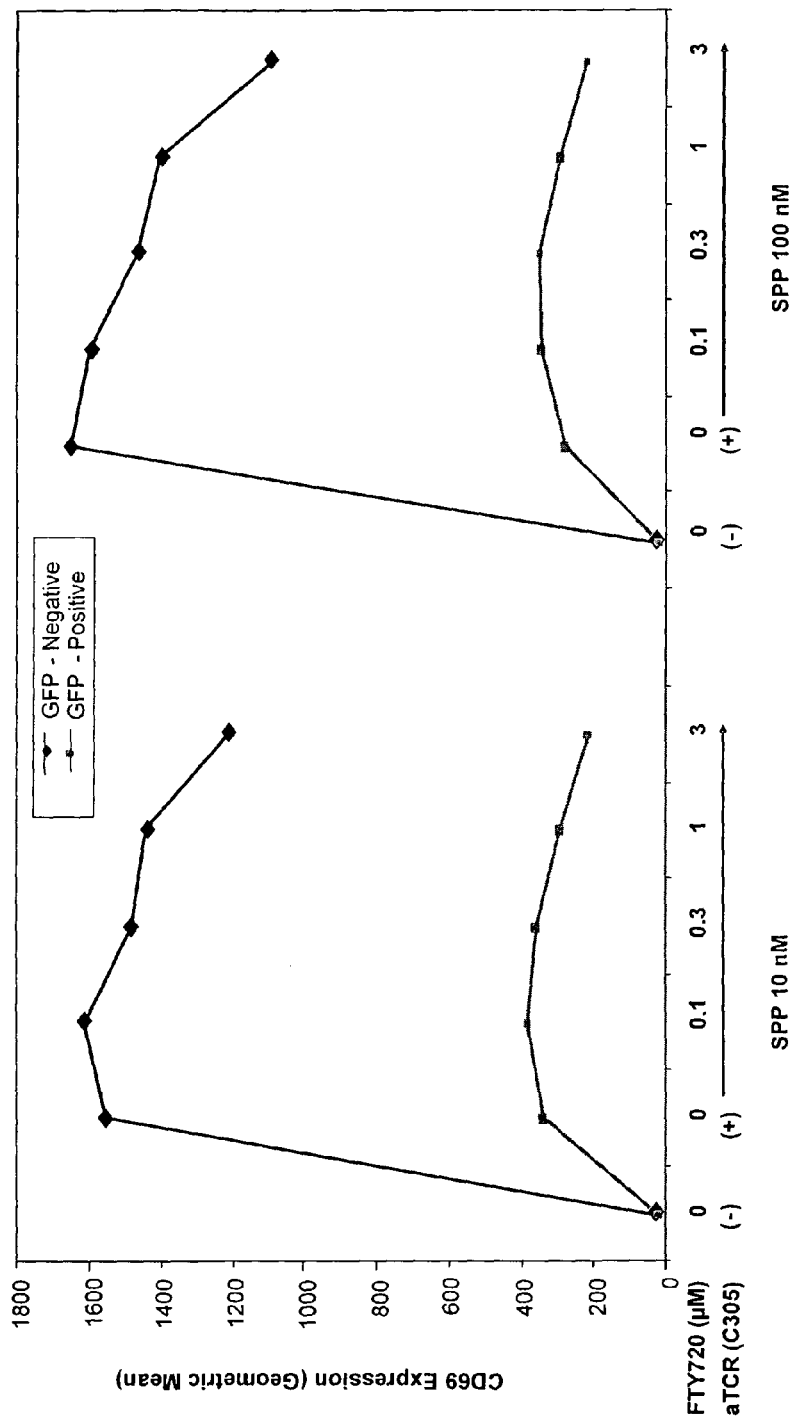
FIG. 36B shows that FTY720 has no effect on EDG-1 wild-type induced CD69 inhibition in Jurkat cells.
Figure 37:
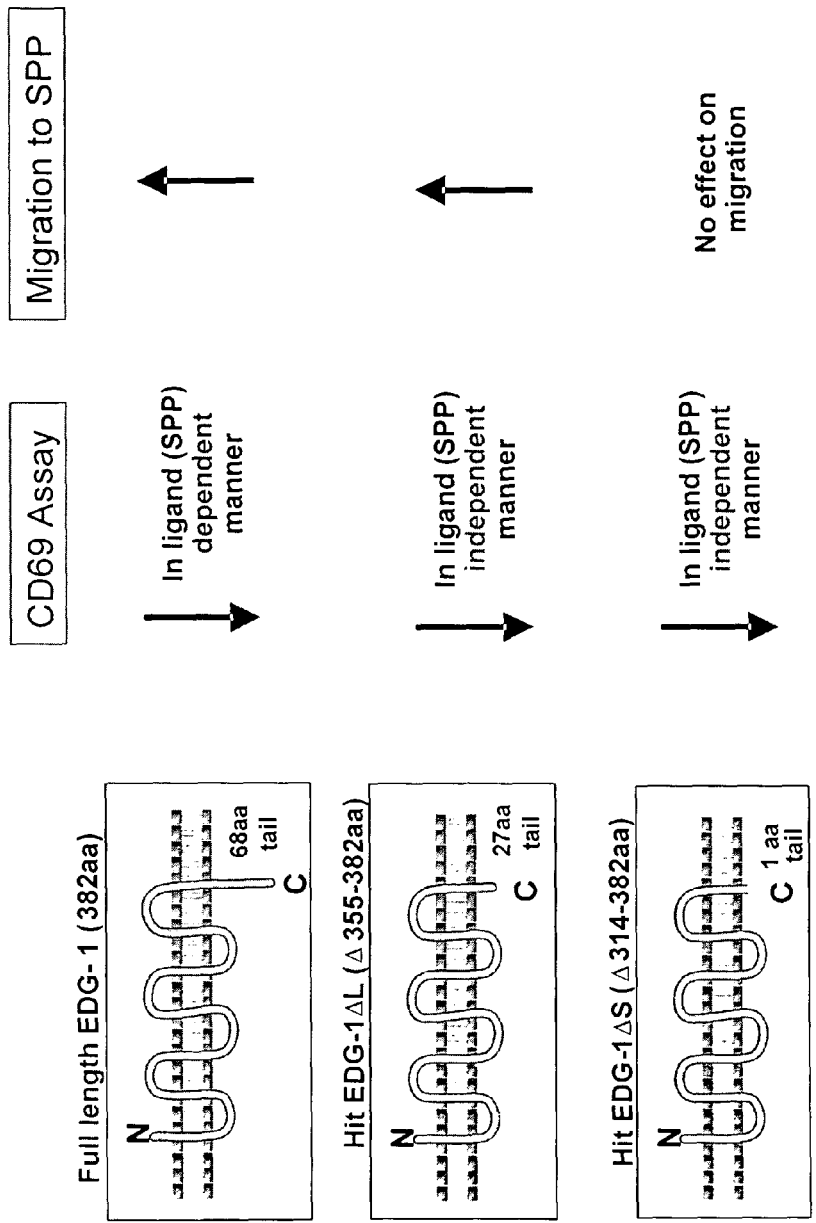
FIG. 37 shows a summary of EDG-1 effects.
Figure 38:
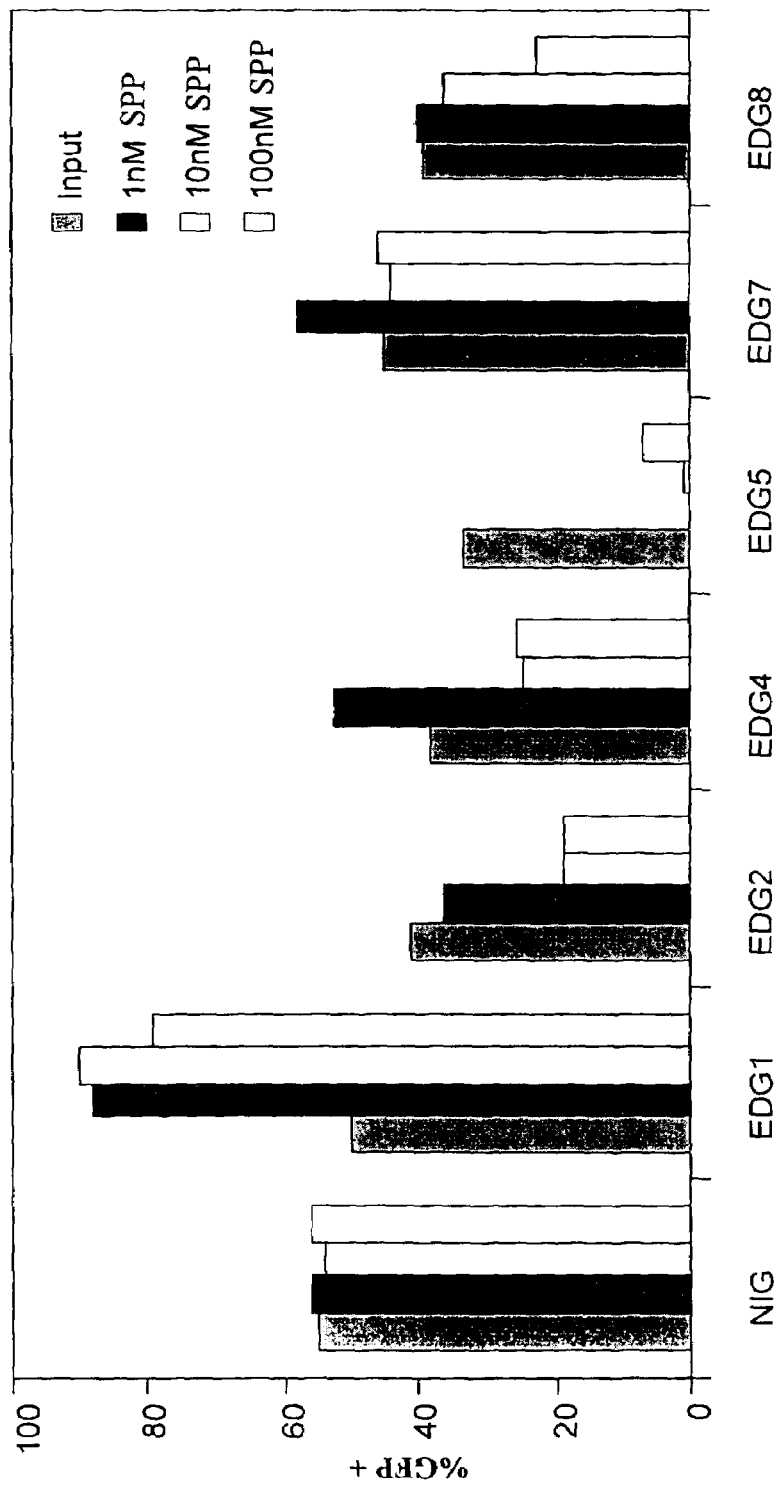
FIG. 38 shows the effect of EDG-1, 2, 4, 5, 7, and 8 on SPP induced migration.

"Lymphocyte migration" refers to migration of B and T lymphocytes to and from primary and secondary lymphoid organs (e.g., bone marrow, thymus, lymph nodes, spleen, Peyer's patch, and tonsils), the periphery, and non-lymphoid tissues via the blood stream, lymphatic vessels, and by penetration of capillary walls (see, e.g., Paul, *Immunology* (3$^{rd}$ ed., 1993) (Chapters 4 and 6)). Without being bound to a particular theory, the present invention demonstrates that EDG proteins, e.g., EDG-1 and EDG-5, participate in the process of lymphocyte migration via ligand binding to and or activation of the EDG protein (e.g., using SPP or LPA or analogs thereof, and/or cytokines). SPP and LPA are present in serum and are produced by a number of cells, including platelets and fibroblasts. Ligand-induced lymphocyte migration can be measured using the assay described in FIG. 33A, in which lymphocytes migrate toward the ligand from an upper to a lower chamber. The sphingolipid analog compound 2-amino-2(2-[4-octylphenyl]ethyl)-1,3-propanediol hydrochloride and analogs thereof inhibit such migration. The C-terminus of EDG-1 appears to be involved in migration. Such domains (e.g., the cytoplasmic tail of EDG-1) can be used in high throughput binding assays for compounds that modulate lymphocyte migration.

"Lymphocyte activation" refers to the process of stimulating quiescent ($G_0$ phase of cell cycle), mature B and T cells by encounter with antigen, either directly or indirectly (e.g., via a helper cell and antigen presenting cells as well as via direct antigen contact with a cell surface molecule of the lymphocyte). Characteristics of activation can include, e.g., increase in cell surface markers such as CD69, entry into the $G_1$ phase of the cell cycle, cytokine production, and proliferation (see, e.g., Paul, *Immunology* (3$^{rd}$ ed., 1993) (Chapters 13 and 14)). Without being bound to a particular theory, the present invention demonstrates that EDG proteins, e.g., EDG-1, participate in modulation of lymphocyte activation, e.g., EDG-1 and EDG-8 inhibit lymphocyte activation.

The terms "EDG" protein or fragment thereof, or a nucleic acid encoding "EDG" or a fragment thereof refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by an EDG nucleic acid or amino acid sequence of an EDG protein, e.g., EDG-1, 3, 5, 6, 8, or EDG-2, 4, and 7; (2) specifically bind to antibodies, e.g., polyclonal antibodies, raised against an immunogen comprising an amino acid sequence of an EDG protein, e.g., EDG-1, 3, 5, 6, 8, or EDG-2, 4, and 7, immunogenic fragments thereof, and conservatively modified variants thereof; (3) specifically hybridize under stringent hybridization conditions to an anti-sense strand corresponding to a nucleic acid sequence encoding an EDG protein, e.g., EDG-1, 3, 5, 6, 8, or EDG-2, 4, and 7, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to an EDG nucleic acid, e.g., EDG-1, 3, 5, 6, 8, or EDG-2,4, and 7.

An EDG polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. The EDG polypeptide further has the ability to bind its naturally occurring ligand, e.g., SPP or LPA, as well as other naturally occurring and synthetic EDG family ligands and their analogs, including sphingolipid-like compounds. The ability to bind an EDG family protein identifies a compound as a sphingolipid analog, e.g., a sphingolipid-like compound. EDG proteins often have GPCR activity, e.g., the ability to transduce a signal via a G protein in response to extracellular ligand binding. For example, EDG-1 is coupled to $G_i$, a pertussis toxin-sensitive G protein. Binding of SPP to EDG-1 results in inhibition of adenylate cyclase and activation of MAPK (both $G_1$-mediated) as well as upregulation of P- and E-cadherin expression and Rho-dependent morphogenesis.

The terms "EDG-1 " protein or a fragment thereof, or a nucleic acid encoding "EDG-1" protein or a fragment thereof refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by SEQ ID NO:1, 2, 3, or 4; (2) specifically bind to antibodies, e.g., polyclonal antibodies, raised against an immunogen comprising an amino acid sequence encoded by SEQ ID NO:1, 2, 3, or 4, immunogenic fragments thereof, and conservatively modified variants thereof; (3) specifically hybridize under stringent hybridization conditions to an antisense strand corresponding to a nucleic acid sequence encoding an EDG protein, e.g., SEQ ID NO:1, 2, 3, or 4, or their complements, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to SEQ ID NO:1, 2, 3, or 4 or their complements. The EDG-1 polypeptide further has the ability to bind its naturally occurring ligand, e.g., SPP, as well as other naturally occurring and synthetic EDG-1 ligands and their analogs, including sphingolipid-like compounds.

The Unigene number for EDG-1 is Hs.154210, and GenBank accession numbers for exemplary nucleotide and amino acids sequences are NM_001400, XM_001499, NP_001391, XP_00149, AAC51905, AAF43420, and AAA52336. The chromosomal location is Chr 1p21. The OMIM reference number for EDG-1 is 601974. EDG-1 is expressed in, e.g., in endothelial cells, vascular smooth muscle cells, fibroblasts, melanocytes and cells of epithelioid origin (see, e.g., Hla & Maciag, *J. Biol. Chem.* 265:9308-9313 (1990); Hobson et al., *Science* 291:1800-1803 (2001); and Lee et al., *Science* 279:1552-1555 (1998)).

Exemplary wild type nucleic acid and protein sequences for additional members of the EDG family are provided by the following OMIM reference numbers (see also FIG. 2 for exemplary amino acid sequences of EDG family members):

For EDG-2, OMIM reference number 602282. The GenBank accession numbers for exemplary nucleotide and amino acids sequences are NM_001401, XM_005557, XM_036690, XM_036691, NP_001392, XP)—5557, XP_036690, XP_036691, AAC00530, AAC51139, CAA70686, and CAA70687. (see, e.g., An et al., *Molec. Pharm.* 54:881-888 (1998); An et al., *Biochem. Biophys. Res. Commun.* 231:619-622 (1997); Contos et al., *Genomics* 51:364-378 (1998); Hecht et al., *J. Cell. Biol.* 135:1071-1083 (1996); and Moolenaar et al., *Curr. Opin. Cell* Biol. 9:168-173 (1997)).

For EDG-3, OMIM reference number 601965. The GenBank accession numbers for exemplary nucleotide and amino acids sequences are NM_005226, NP_005217, CAA58744 and AAC51906. (see, e.g., An et al., *FEBS Lett.* 417:279-282 (1997); and Yamaguchi et al., *Biochem. Biophys. Res. Commun.* 227:608-614 (1996)).

For EDG-4, OMIM reference number 605110. The GenBank accession numbers for exemplary nucleotide and amino acids sequences are NM_004720, XM_012893, XM_048494, XM_048495, NP_004711, XP_012893, XP_048494, XP_048495, AAB61528, AAC27728 and AAF43409. (see, e.g., An et al., *J. Biol. Chem.* 273:7906-7910 (1998); An et al., *Molec. Pharm.* 54:881-888 (1998); Contos et al., *Genomics* 64:155-169 (2000); and Goetzl et al., *J. Immunol.* 164:4996-4999 (2000)).

For EDG-5, OMIM reference number 605111. The GenBank accession numbers for exemplary nucleotide and amino acids sequences are NM_004230, XM_008898, NP_004221, XP_008898, and AAC98919. (see, e.g., An et al., *J. Biol. Chem.* 275:288-296 (2000); Kupperman et al., *Nature* 406:192-195 (2000); and MacLennan et al., *Molec. Cell. Neurosci.* 5:201-209 (1994)).

For EDG-6, OMIM reference number 603751. The GenBank accession numbers for exemplary nucleotide and amino acids sequences are NM_003775, XM_009219, NP_003766, XP_009219, and CAA04118. (see, e.g., Graler et al., *Genomics* 53:164-169 (1998); and Jedlicka et al., *Cytogenet. Cell. Genet.* 65:140 (1994)).

For EDG-7, OMIM reference number 605106. The GenBank accession numbers for exemplary nucleotide and amino acids sequences are NM_012152, XM_002057, XM_035234, NP_036284, XP_002057, XP_035234, AAD56311, AAF00530, and AAF91291. (see, e.g., Bandoh et al, *J. Biol. Chem.* 274:27776-27785 (1999)).

For EDG-8, OMIM reference number 605146. The GenBank accession numbers for exemplary nucleotide and amino acids sequences are NM_030760, XM_049584, NP_110387, XP_049584, and AAG3813. (see, e.g., Im et al., *J. Biol. Chem.* 275:14281-14286 (2000)).

As described above, EDG proteins have "G-protein coupled receptor activity," e.g., they bind to G-proteins in response to extracellular stimuli, such as ligand binding, and promote production of second messengers such as IP3, cAMP, and $Ca^{2+}$ via stimulation of enzymes such as phospholipase C and adenylate cyclase. Such activity can be measured in a heterologous cell, by coupling a GPCR (or a chimeric GPCR) to a G-protein, e.g., a promiscuous G-protein such as G$\alpha$15, and an enzyme such as PLC, and measuring increases in intracellular calcium using (Offermans & Simon, *J. Biol. Chem.* 270:15175-15180 (1995)). Receptor activity can be effectively measured, e.g., by recording ligand-induced changes in $[Ca^{2+}]_i$ and calcium influx using fluorescent $Ca^{2+}$-indicator dyes and fluorometric imaging.

G protein coupled receptors are glycoproteins that share certain structural similarities (see, e.g., Gilman, *Ann. Rev. Biochem.* 56:615-649 (1987), Strader et al., *The FASEB J.* 3:1825-1832 (1989), Kobilka et al., *Nature* 329:75-79 (1985), and Young et al., *Cell* 45:711-719 (1986)). For example, G protein coupled receptors have an extracellular domain, seven hydrophobic stretches of about 20-25 amino acids in length interspersed with eight hydrophilic regions (collectively known as the transmembrane domain), and a cytoplasmic tail. Each of the seven hydrophobic regions forms a transmembrane alpha helix, with the intervening hydrophilic regions forming alternatively intracellular and extracellular loops. The third cytosolic loop between transmembrane domains five and six is involved in G-protein interaction. These transmembrane hydrophobic domains, hydrophilic loop domains, extracellular domains, and cytoplasmic tail domains can be structurally identified using methods known to those of skill in the art, such as sequence analysis programs that identify hydrophobic and hydrophilic domains (see, e.g., Kyte & Doolittle, *J. Mol. Biol.* 157:105-132 (1982)). Such domains are useful for making chimeric proteins and for in vitro assays of the invention (see, e.g., WO 94/05695 and U.S. Pat. No. 5,508,384). Such domains are also considered "fragments" of EDG proteins, and as such are useful in the assays of the invention, e.g., for ligand binding studies, or for signal transduction studies using chimeric proteins.

The phrase "functional effects" in the context of assays for testing compounds that modulate activity of an EDG protein includes the determination of a parameter that is indirectly or directly under the influence of an EDG GPCR, e.g., an indirect, chemical or phenotypic effect such as inhibition of lymphocyte activation or migration represented by a change in expression of a cell surface marker or cytokine production upon TCR stimulation, or changes in cellular proliferation or apoptosis, or signal transduction leading to increases in intracellular calcium; or, e.g., a direct, physical effect such as ligand binding or inhibition of ligand binding or movement from one chamber to another in response to ligand. A functional effect therefore includes ligand binding activity, the ability of cells to proliferate, the ability of cells to migrate, apoptosis, gene expression in cells undergoing activation, expression of cell surface molecules such as CD69, signal transduction, production of cytokines, calcium influx, and other characteristics of activated and/or migrating lymphocytes. "Functional effects" include in vitro, in vivo, and ex vivo activities.

By "determining the functional effect" is meant assaying for a compound that increases or decreases a parameter that is indirectly or directly under the influence of an EDG GPCR protein, e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity, e.g., SPP or LPA or analogs thereof or sphingolipid-like compounds, either naturally occurring or synthetic; measuring cellular proliferation; measuring cellular movement towards a ligand; measuring apoptosis; measuring cell surface marker expression, e.g., CD69; measuring cytokine, e.g., IL-2, production; measurement of calcium influx; measurement of changes in protein levels for EDG-associated sequences; measurement of RNA stability; G-protein binding; GPCR phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

"Inhibitors", "activators", and "modulators" of EDG polynucleotide and polypeptide sequences are used to refer to activating, inhibitory, or modulating molecules identified using in vitro and in vivo assays of EDG polynucleotide and polypeptide sequences. Inhibitors are compounds that, e.g., bind to, partially or totally block activity, decrease, prevent, delay activation, inactivate, desensitize, or down regulate the activity or expression of EDG proteins, e.g., antagonists. "Activators" are compounds that increase, open, activate, facilitate, enhance activation, sensitize, agonize, or up regulate EDG protein activity. Inhibitors, activators, or modulators also include genetically modified versions of EDG proteins, e.g., versions with altered activity, as well as naturally occurring and synthetic ligands, antagonists, agonists, peptides, cyclic peptides, nucleic acids, antibodies, antisense molecules, ribozymes, small organic molecules and the like. Such assays for inhibitors and activators include, e.g., expressing EDG protein in vitro, in cells, cell extracts, or cell membranes, applying putative modulator compounds, and then determining the functional effects on activity, as described above.

Samples or assays comprising EDG proteins that are treated with a potential activator, inhibitor, or modulator are compared to control samples without the inhibitor, activator, or modulator to examine the extent of activation or migration modulation. Control samples (untreated with inhibitors) are assigned a relative protein activity value of 100%. Inhibition of EDG is achieved when the activity value relative to the control is about 80%, preferably 50%, more preferably 25-0%. Activation of EDG is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to directly or indirectly modulation lymphocyte activation or migration. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

"FTY720" refers to a chemical molecule of the formula 2-amino-2(2-[4-octylphenyl]ethyl)-1,3-propanediol hydrochloride. FTY720 is a sphingolipid analog. FTY720 and analogs thereof are useful for inhibiting EDG-1 and EDG family mediated lymphocyte migration. FTY720 and analogs thereof are designed and made according to methods known to those of skill in the art (see, e.g., U.S. Pat. No. 6,004,565, 5,604,229, and PCT application PCT/JP95/01654, and Fujita et al., *J. Antibiotics* 47:216-224 (1994)).

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequences SEQ ID NO:1, 2, 3, or 4), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Bio.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to EDG protein as encoded by SEQ ID NO:1, 2, 3, or 4, polymorphic variants, alleles, orthologs, and conservatively modified variants, or splice variants, or portions thereof, can be selected to obtain only those polyclonal antibodies that are specifically immunoreactive with EDG proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

Assays for Proteins that Modulation Lymphocyte Activation

High throughput functional genomics assays can be used to identify modulators of lymphocyte activation. Such assays can monitor changes in cell surface marker expression, cytokine production, antibody production, proliferation and differentiation, and apoptosis, using either cell lines or primary cells. Typically, the lymphocytes are contacted with a cDNA or a random peptide library (encoded by nucleic acids). The cDNA library can comprise sense, antisense, full length, and truncated cDNAs. The peptide library is encoded by nucleic acids. The lymphocytes are then activated, e.g., by activating either the T cell receptor (TCR, also known as CD3) or the B cell receptor (BCR, also known as surface or mIg), as appropriate, e.g., using antibodies to the receptor. The effect of the cDNA or peptide library on the phenotype of lymphocyte activation is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., EDG) can be isolated using a yeast two-hybrid system, mammalian two hybrid system, or phage display screen, etc. Targets so identified can be further used as bait in these assays to identify additional members of the lymphocyte activation pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable B cell lines include surface Ig(+) lines such as CL-01, LA350, and CA46, as well as other mature and immature B cell lines and primary B cells known to those of skill in the art. Suitable T cell lines include Jurkat, HPB-ALL, HSB-2, and PEER, as well as other mature and immature T cell lines and primary T cells known to those of skill in the art. Suitable B cell surface markers, for assaying B cell activation, include MHC class I, MHC class II, CD23, CD40, CD58, CD69, CD72, CD80, CD86, LFA-1, LFA-3, and ICAM-1, as well as other cell surface markers known to those of skill in the art. Suitable T cell surface markers include MHC class II, CD2, CD3, CD4, CD5, CD8, CD25, CD28, CD69, CD40L, LFA-1, and ICAM-1 as well as other cell surface markers known to those of skill in the art (see, e.g., Yablonski et al., *Science* 281:413-416 (1998)). Suitable cytokines, for measuring either production or response, include IL-2, IL-4, IL-5, IL-6, IL-10, INF-γ, and TGF-β, as well as their corresponding receptors.

Cell surface markers can be assayed using fluorescently labeled antibodies and FACS. Cell proliferation can be measured using $^3$H-thymidine or dye inclusion. Apoptosis can be measured using dye inclusion, or by assaying for DNA laddering or increases in intracellular calcium. Cytokine production can be measured using an immunoassay such as ELISA.

cDNA libraries are made from any suitable source, preferably from primary human lymphoid organs such as thymus, spleen, lymph node, and bone marrow. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

In a preferred embodiment, target proteins that modulate lymphocyte activation, preferably T cell activation, are identified using a high throughput cell based assay (using a microtiter plate format) and FACS screening for CD69 cell surface expression (see FIGS. 3-10 and Example I). cDNA libraries are made from primary lymphocyte organs. These cDNA libraries include, e.g., sense, antisense, full length, and truncated cDNAs. The cDNAs are cloned into a retroviral vector with a tet-regulatable promoter. Jurkat cells are infected with the library, the cells are stimulated with anti-TCR antibodies, and then the cells are sorted using fluorescent antibodies and FACS for CD69 low/CD3+ cells. Cells with the desired phenotype are recovered, expanded, and cloned. A Tet-regulatable phenotype is established to distinguish somatic mutations. The cDNA is rescued. Optionally, the phenotype is validated by assaying for IL-2 production using primary lymphocytes. Optionally, a marker such as GFP can be used to select for retrovirally infected cells. Using this system, cDNAs encoding EDG-1 were identified as inhibitors of T cell activation.

Isolation of Nucleic Acids Encoding EDG Family Members

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al, eds., 1994)).

EDG nucleic acids, polymorphic variants, orthologs, and alleles that are substantially identical to an amino acid sequence encoded by SEQ ID NO:1-4, as well as other EDG family members, can be isolated using EDG nucleic acid probes and oligonucleotides under stringent hybridization conditions, by screening libraries. Alternatively, expression libraries can be used to clone EDG protein, polymorphic variants, orthologs, and alleles by detecting expressed homologs immunologically with antisera or purified antibodies made against human EDG or portions thereof.

To make a cDNA library, one should choose a source that is rich in EDG RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffmnan, Gene 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180-182 (1977). Colony hybridization is carried out as generally described in Grunstein et al., Proc. Natl. Acad. Sci. USA., 72:3961-3965 (1975).

An alternative method of isolating EDG nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of human EDG directly from mRNA, from cDNA, from genomic libraries or cDNA libraries. Degenerate oligonucleotides can be designed to amplify EDG homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of EDG encoding mRNA in physiological samples, for nucleic acid sequencing, or for other purposes. Genes amplified by the PCR reaction can be purified from agarose gels and cloned into an appropriate vector.

Gene expression of EDG can also be analyzed by techniques known in the art, e.g., reverse transcription and amplification of MRNA, isolation of total RNA or poly A$^+$RNA, northern blotting, dot blotting, in situ hybridization, RNase protection, high density polynucleotide array technology, e.g., and the like.

Nucleic acids encoding EDG protein can be used with high density oligonucleotide array technology (e.g., GeneChip™) to identify EDG protein, orthologs, alleles, conservatively modified variants, and polymorphic variants in this invention. In the case where the homologs being identified are linked to modulation of T cell activation and migration, they can be used with GeneChip™ as a diagnostic tool in detecting the disease in a biological sample, see, e.g., Gunthand et al., AIDS Res. Hum. Retroviruses 14: 869-876 (1998); Kozal et al., Nat. Med. 2:753-759 (1996); Matson et al., Anal. Biochem. 224: 110-106 (1995); Lockhart et al., Nat. Biotechnol. 14:1675-1680 (1996); Gingeras et al., Genome Res. 8:435-448 (1998); Hacia et al., Nucleic Acids Res. 26:3865-3866 (1998).

The gene for EDG is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding EDG, one typically subclones EDG into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the EDG protein are available in, e.g., E. coli, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the EDG encoding nucleic acid in host cells. A typical expression cassette thus contains a promoter operably linked to the nucleic acid sequence encoding EDG and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a EDG encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of EDG protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing EDG.

After the expression vector is introduced into the cells, the transfected cells are cultured under conditions favoring expression of EDG, which is recovered from the culture using standard techniques identified below.

Purification of EDG Polypeptides

Either naturally occurring or recombinant EDG can be purified for use in functional assays. Naturally occurring EDG can be purified, e.g., from human tissue. Recombinant EDG can be purified from any suitable expression system.

The EDG protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant EDG protein is being purified. For example, proteins having established molecular adhesion properties can be reversible fused to the EDG protein. With the appropriate ligand, EDG protein can be selectively adsorbed to a purification column and then freed from the column in a relatively pure form. The fused protein is then removed by enzymatic activity. Finally, EDG protein could be purified using immunoaffinity columns.

A. Purification of EDG from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of EDG protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of immunologically and/or biologically active protein. Other suitable buffers are known to those skilled in the art. Human EDG proteins are separated from other bacterial proteins by standard separation techniques, e.g., with Ni-NTA agarose resin.

Alternatively, it is possible to purify EDG protein from bacteria periplasm. After lysis of the bacteria, when the EDG protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying EDG Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the EDG proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The EDG proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of EDG Protein

A. Assays

Modulation of an EDG protein, and corresponding modulation of lymphocyte activation and/or migration, can be assessed using a variety of in vitro and in vivo assays, including cell-based models as described above. Such assays can be used to test for inhibitors and activators of EDG protein or fragments thereof, and, consequently, inhibitors and activators of lymphocyte activation and migration. Such modulators of EDG protein, which is involved in lymphocyte activation and migration, are useful for treating disorders related to T and B cell activation and migration. Modulators of EDG protein are tested using either recombinant or naturally occurring EDG, preferably human EDG.

Preferably, the EDG protein will have the sequence as encoded by SEQ ID NO:1-4, or an exemplary Genbank Accession number as provided herein, or a conservatively modified variant thereof. Alternatively, the EDG protein of the assay will be derived from a eukaryote and include an amino acid subsequence having substantial amino acid sequence identity to a sequence encoded by SEQ ID NO:1-4. Generally, the amino acid sequence identity will be at least 60%, preferably at least 65%, 70%, 75%, 80%, 85%, or 90%, most preferably at least 95%.

Measurement of lymphocyte activation, migration, or loss-of-lymphocyte activation or migration phenotype on EDG protein or cell expressing EDG protein, either recombinant or naturally occurring, can be performed using a variety of assays, in vitro, in vivo, and ex vivo, as described herein. A suitable physical, chemical or phenotypic change that affects activity or binding can be used to assess the influence of a test compound on the polypeptide of this invention. When the functional effects are determined using intact cells or animals, one can also measure a variety of effects such as, in the case of signal transduction, e.g., ligand binding (SPP, LPA, GTP), hormone release, transcriptional changes to both known and uncharacterized genetic markers (e.g., northern blots), cellular movement towards a ligand, movement of labeled cells, changes in cell metabolism such as pH changes, and changes in intracellular second messengers such as $Ca^{2+}$, IP3, cGMP, or cAMP; as well as changes related to lymphocyte activation and migration, e.g., cellular proliferation, cell surface marker expression, e.g., CD69, cytokine production, and apoptosis.

In one preferred embodiment, described herein in Example I, measurement of CD69 activation and FACS sorting is used to identify modulators of lymphocyte, e.g., T cell, activation. In another preferred embodiment, shown in FIG. 33A, measurement of cellular migration toward a ligand is used to identify modulators of lymphocyte, e.g., T cell, migration.

In vitro Assays

Assays to identify compounds with EDG modulating activity can be performed in vitro. Such assays can used full length EDG protein or a variant thereof (see, e.g., SEQ ID NOS:1-4), or a fragment of an EDG protein, such as an extracellular domain or a cytoplasmic domain, optionally fused to a heterologous protein to form a chimera. In one embodiment, different domains can be used to assay for activation and migration. In another embodiment, the same domain can be used to assay for activation and migration. In one embodiment, the C-terminal cytoplasmic tail (e.g., amino acids 315-382) can be used in high throughput binding assays to identify compounds that modulate lymphocyte migration. Purified recombinant or naturally occurring EDG protein can be used in the in vitro methods of the invention. In addition to purified EDG protein or fragment thereof, the recombinant or naturally occurring EDG protein can be part of a cellular lysate or a cell membrane. As described below, the binding assay can be either solid state or soluble. Preferably, the protein, fragment thereof or membrane is bound to a solid support, either covalently or non-covalently. Often, the in vitro assays of the invention are ligand binding or ligand affinity assays, either non-competitive or competitive (with known extracellular ligands SPP or LPA, or with a known intracellular ligand GTP). Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the EDG protein or fragment thereof is contacted with a potential modulator and incubated for a suitable amount of time. In one embodiment, the potential modulator is bound to a solid support, and the EDG protein is added. In another embodiment, the EDG protein is bound to a solid support. A wide variety of modulators can be used, as described below, including small organic molecules, peptides, antibodies, and EDG ligand analogs. A wide variety of assays can be used to identify EDG-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for the EDG family are known (SPP, LPA, and GTP). Either the modulator or the known ligand is bound first, and then the competitor is added. After the EDG protein is washed, interference with binding, either of the potential modulator or of the known ligand, is determined. Often, either the potential modulator or the known ligand is labeled.

Cell-based In vivo Assays

In another embodiment, EDG protein is expressed in a cell, and functional, e.g., physical and chemical or phenotypic, changes are assayed to identify EDG and lymphocyte activation and migration modulators. Cells expressing EDG proteins can also be used in binding assays. Any suitable functional effect can be measured, as described herein. For example, ligand binding, cell surface marker expression, cellular proliferation, apoptosis, cytokine production, and GPCR signal transduction, e.g., changes in intracellular $Ca^{2+}$ levels, are all suitable assays to identify potential modulators using a cell based system. Suitable cells for such cell based assays include both primary lymphocytes and cell lines, as described herein. The EDG protein can be naturally occurring or recombinant. Also, as described above, fragments of EDG proteins or chimeras with GPCR activity can be used in cell based assays. For example, the extracellular domain of an EDG protein can be fused to the transmembrane and/or cytoplasmic domain of a heterologous protein, preferably a heterologous GPCR. Such a chimeric GPCR would have GPCR activity and could be used in cell based assays of the invention. In another embodiment, a domain of the EDG protein, such as the extracellular or cytoplasmic domain, is used in the cell-based assays of the invention.

As described above, in one embodiment, lymphocyte activation is measured by contacting T cells comprising an EDG target with a potential modulator and activating the cells with an anti-TCR antibody. Modulation of T cell activation is identified by screening for cell surface marker expression, e.g., CD69 expression levels, using fluorescent antibodies and FACS sorting. In another embodiment, lymphocyte migration is measured by observing T cell migration from an upper to a lower chamber containing an EDG ligand such as SPP.

In another embodiment, cellular proliferation, migration, or apoptosis can be measured using $^3$H-thymidine incorporation or dye inclusion. Cytokine production can be measured using an immunoassay such as an ELISA.

In another embodiment, cellular EDG polypeptide levels are determined by measuring the level of protein or mRNA. The level of EDG protein or proteins related to EDG signal transduction are measured using immunoassays such as western blotting, ELISA and the like with an antibody that selectively binds to the EDG polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, EDG expression can be measured using a reporter gene system. Such a system can be devised using an EDG protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to GPCR signal transduction can be measured. An activated or inhibited EDG G-coupled protein receptor will alter the properties of target enzymes, second messengers, channels, and other effector proteins. The examples include the activation of cGMP phosphodiesterase, adenylate cyclase, phospholipase C, IP3, and modulation of diverse channels by G proteins. Downstream consequences can also be examined such as generation of diacyl glycerol and IP3 by phospholipase C, and in turn, for calcium mobilization by IP3. Activated GPCR receptors become substrates for kinases that phosphorylate the C-terminal tail of the receptor (and possibly other sites as well). Thus, activators will promote the transfer of $^{32}$P from gamma-labeled GTP to the receptor, which can be assayed with a scintillation counter. The phosphorylation of the C-terminal tail will promote the binding of arrestin-like proteins and will interfere with the binding of G-proteins. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

As described above, activation of some G-protein coupled receptors stimulates the formation of inositol triphosphate (IP3) through phospholipase C-mediated hydrolysis of phosphatidylinositol (Berridge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

In one example, EDG GPCR activity is measured by expressing an EDG GPCR in a heterologous cell with a promiscuous G-protein that links the receptor to a phospholipase C signal transduction pathway (see Offermanns & Simon, *J. Biol. Chem.* 270:15175-15180 (1995)). Modulation of signal transduction is assayed by measuring changes in intracellular $Ca^{2+}$ levels, which change in response to modulation of the GPCR signal transduction pathway via administration of a molecule that associates with an EDG GPCR. Changes in $Ca^{2+}$ levels are optionally measured using fluorescent $Ca^{2+}$ indicator dyes and fluorometric imaging.

In another example, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

Other assays can involve determining the activity of receptors which, when activated, result in a change in the level of intracellular cyclic nucleotides, e.g., cAMP or cGMP, by activating or inhibiting enzymes such as adenylate cyclase. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay.

In one example, the changes in intracellular cAMP or cGMP can be measured using immunoassays. The method described in Offermanns & Simon, *J. Biol. Chem.* 270:15175-15180 (1995) may be used to determine the level of CAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference.

In one example, assays for G-protein coupled receptor activity include cells that are loaded with ion or voltage sensitive dyes to report receptor activity, e.g., by observing calcium influx or intracellular calcium release. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as G$\alpha$15 and G$\alpha$16 can be used in the assay of choice (Wilkie et al., *Proc. Nat'l Acad. Sci. USA* 88:10049-10053 (1991)). Such promiscuous G-proteins allow coupling of a wide range of receptors.

Animal Models

Animal models of lymphocyte activation and migration also find use in screening for modulators of lymphocyte activation or migration. Similarly, transgenic animal technology including gene knockout technology, for example as a result of homologous recombination with an appropriate gene targeting vector, or gene overexpression, will result in the absence or increased expression of the EDG protein. The same technology can also be applied to make knock-out cells. When desired, tissue-specific expression or knockout of the EDG protein may be necessary. Transgenic animals generated by such methods find use as animal models of lymphocyte activation and migration and are additionally useful in screening for modulators of lymphocyte activation and migration.

Knock-out cells and transgenic mice can be made by insertion of a marker gene or other heterologous gene into an endogenous EDG gene site in the mouse genome via homologous recombination. Such mice can also be made by substituting an endogenous EDG with a mutated version of the EDG gene, or by mutating an endogenous EDG, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators

The compounds tested as modulators of EDG protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an EDG protein. Typically, test compounds will be small organic molecules, peptides, lipids, and lipid analogs. In one embodiment, the compound is a sphingolipid analog, either naturally occurring or synthetic. In another embodiment, the compound is 2-amino-2(2-[4-octylphenyl]ethyl)-1,3-propanediol hydrochloride (also known as FTY720) or an analog thereof.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries"

or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a EDG protein, or a cell or tissue expressing an EDG protein, either naturally occurring or recombinant. In another embodiment, the invention provides solid phase based in vitro assays in a high throughput format, where the EDG protein or fragment thereof, such as the cytoplasmic domain, is attached to a solid phase substrate. Any one of the assays described herein can be adapted for high throughput screening, e.g., ligand binding, cellular proliferation, cell surface marker flux, e.g., CD-69, screening, radiolabeled GTP binding, second messenger flux, e.g., $Ca^{2+}$, IP3, cGMP, or cAMP, cytokine production, etc. In one preferred embodiment, the cell-based system using CD-69 modulation and FACS assays is used in a high throughput format for identifying modulators of EDG proteins, and therefore modulators of T cell activation.

In the high throughput assays of the invention, either soluble or solid state, it is possible to screen up to several thousand different modulators or ligands in a single day. This methodology can be used for EDG proteins in vitro, or for cell-based or membrane-based assays comprising an EDG protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selection family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of EDG Polypeptides

In addition to the detection of EDG gene and gene expression using nucleic acid hybridization technology, one can also use immunoassays to detect EDG proteins of the invention. Such assays are useful for screening for modulators of EDG and lymphocyte activation and migration, as well as for therapeutic and diagnostic applications. Immunoassays can be used to qualitatively or quantitatively analyze EDG protein. A general overview of the applicable technology can be found in Harlow & Lane, *Antibodies: A Laboratory Manual* (1988).

A. Production of Antibodies

Methods of producing polyclonal and monoclonal antibodies that react specifically with the EDG proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)), A number of immunogens comprising portions of EDG protein may be used to produce antibodies specifically reactive with EDG protein. For example, recombinant EDG protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al, *Science* 246:1275-1281 (1989).

Monoclonal antibodies and polyclonal sera are collected and titered against the imnunogen protein in an immunoassay, for example, a solid phase immunoassay with the immunogen immobilized on a solid support. Typically, polyclonal antisera with a titer of $10^4$ or greater are selected and tested for their cross reactivity against non-EDG proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular EDG family member, such as EDG1, or a particular EDG-1 ortholog, such as human EDG1, can also be made, by subtracting out other cross-reacting EDG family members or orthologs from a species such as a non-human mammal. In this manner, antibodies that bind only to a particular EDG protein or ortholog may be obtained.

Once the specific antibodies against EDG protein are available, the protein can be detected by a variety of immunoassay methods. In addition, the antibody can be used therapeutically as a EDG modulators. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

EDG protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the EDG protein or antigenic subsequence thereof). The antibody (e.g., anti-EDG) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled EDG or a labeled anti-EDG antibody. Alternatively, the labeling agent may be a third moiety, such as a secondary antibody, that specifically binds to the antibody/EDG complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting EDG in samples may be either competitive or noncompetitive. Noncompetitive immunoassays are assays in which the amount of antigen is directly measured. In one preferred "sandwich" assay, for example, the anti-EDG antibodies can be bound directly to a solid substrate on which they are immobilized. These immobilized antibodies then capture EDG present in the test sample. EDG proteins thus immobilized are then bound by a labeling agent, such as a second EDG antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of EDG protein present in the sample is measured indirectly by measuring the amount of a known, added (exogenous) EDG protein displaced (competed away) from an anti-EDG antibody by the unknown EDG protein present in a sample. In one competitive assay, a known amount of EDG protein is added to a sample and the sample is then contacted with an antibody that specifically binds to EDG protein. The amount of exogenous EDG protein bound to the antibody is inversely proportional to the concentration of EDG protein present in the sample. In a particularly preferred embodiment, the antibody is immobilized on a solid substrate. The amount of EDG protein bound to the antibody may be determined either by measuring the amount of EDG present in EDG protein/antibody complex, or alternatively by measuring the amount of remaining uncomplexed protein. The amount of EDG protein may be detected by providing a labeled EDG molecule.

A hapten inhibition assay is another preferred competitive assay. In this assay the known EDG protein is immobilized on a solid substrate. A known amount of anti-EDG antibody is added to the sample, and the sample is then contacted with the immobilized EDG. The amount of anti-EDG antibody bound to the known immobilized EDG is inversely proportional to the amount of EDG protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, an EDG protein can be immobilized to a solid support. Proteins (e.g., EDG and homologs) are added to the assay that compete for binding of the antisera to the immobilized antigen. The ability of the added proteins to compete for binding of the antisera to the immobilized protein is compared to the ability of the EDG protein to compete with itself. The percent cross-reactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an EDG protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the EDG protein that is required to inhibit 50% of binding, then the second protein is said to specifically bind to the polyclonal antibodies generated to EDG immunogen.

Other Assay Formats

Western blot (immunoblot) analysis is used to detect and quantify the presence of EDG in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind EDG. The anti-EDG antibodies specifically bind to the EDG on the solid support. These antibodies may be directly labeled or alternatively may be subsequently detected using labeled antibodies (e.g., labeled sheep anti-mouse antibodies) that specifically bind to the anti-EDG antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize EDG protein, or secondary antibodies that recognize anti-EDG.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodainine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of EDG protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a EDG protein of the present invention, thereby mitigating the effects of absent, partial inactivation, or abnormal expression of an EDG gene, particularly as it relates to T cell activation and migration. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the EDG protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of EDG1 and Other Genes Involved in Modulation of T Cell Activation and Migration A. Introduction In this study, an approach to identify new targets for immune suppressive drugs is provided. It is known that following T cell activation, expression of numerous cell surface markers such as CD25, CD69, and CD40L are upregulated. CD69 has been shown to be an early activation marker in T, B, and NK cells. CD69 is a disulfide-linked dimer. It is not expressed in resting lymphocytes but appears on T, B and NK cells after activation in vitro. Its relevance as a TCR signaling outcome has been validated using T cell deficient in certain key signaling molecules such as LAT and SLP76 (Yablonski, supra). Furthermore, re-introducing SLP76 to the deficient cells results in restoration of CD69 expression. CD69 upregulation was therefore to be used to monitor TCR signal transduction. The rationale of the functional genomics screen was then to identify cell clones whose CD69 upregulation was repressed following introduction of a retroviral cDNA library. The library members conferring such repression would then represent immune modulators that function to block TCR signal transduction.

b. Results

Several T cell lines, including Jurkat, HPB-ALL, HSB-2 and PEER were tested for the presence of surface CD3, CD25, CD28, CD40L, CD69, CD95, and CD95L. Those that express CD3 were cultured with anti-CD3 or anti-TCR to crosslink the TCR and examined for the upregulation of CD69. Jurkat T cell line was selected for its ability to upregulate CD69 in response to crosslinking of their TCR with a kinetics mimicking that of primary T lymphocytes (data not shown). The population of Jurkat cells was sorted for low basal and highly inducible CD69 expression following anti-TCR stimulation. Clone 4D9 was selected because CD69 in this clone was uniformly and strongly induced following TCR stimulation in 24 hours.

In order to regulate the expression of the retroviral library, the Tet-Off system was used. Basically, cDNA inserts in the retroviral library were cloned behind the tetracycline regulatory element (TRE) and the minimal promoter of TK. Transcription of the cDNA inserts were then dependent on the presence of tetracycline-controlled trans-activator (tTA), a fusion of Tet repression protein and the VP16 activation domain, and the absence of tetracyaline or its derivatives such as doxycycline (Dox). To shut off the cDNA expression, one can simply add doxycycline in the medium. To obtain a Jurkat clone stably expresses tTA, retroviral LTR-driven tTA was introduced in conjunction with a TRE-dependent reporter construct, namely TRA-Lyt2. Through sorting of Lyt2 positive cells in the absence of Dox and Lyt2 negative cells in the presence of Dox, coupled with clonal evaluation, a derivative of Jurkat clone 4D9 was obtained, called 4D9#32, that showed the best Dox regulation of Lyt2 expression.

Positive controls: ZAP70 is a positive regulator of T cell activation. A kinase-inactivated (KI) ZAP70 and a truncated ZAP70 (SH2 N+C) were subcloned into the retroviral vector under TRE control. ZAP70 SH2 (N+C) and ZAP70 KI both inhibited TCR-induced CD69 expression. Consistent with the published report on dominant negative forms of ZAP70 on NFAT activity, the truncated protein is also a more potent inhibitor of CD69 induction. In addition, the higher protein expression, as shown by adjusting GFP-gating, the stronger the inhibition was. When one puts the marker M1 at bottom 1% of the uninfected cells, one has a 40% likelihood of obtaining cells whose phenotype resembled that of ZAP70 SH2 (N+C). This translates into a 40:1 enrichment of the desired phenotype.

The CD69 inhibitory phenotype is dependent on expression of dominant negative forms of ZAP70. When Dox was added for 7 days before TCR was stimulated, there was no inhibition of CD69 expression. Analysis of cellular phenotype by FACS of GFP, which was produced from the bicistronic mRNA ZAP70 SH2 (N+C)-IRES-GFP, revealed a lack of GFP+ cells. The lack of ZAP70 SH2 (N+C) expression in the presence of Dox was confirmed by Western.

Screening for cells lacking CD69 upregulation: Jurkat 4D9#32 cells were infected with cDNA libraries made form primary human lymphoid organs such as thymus, spleen, lymph node and bone marrow. The library complexity was $5 \times 10^7$ and was built on the TRE vector. A total of $7.1 \times 10^8$ cells were screened with an infection rate of 52%, as judged by parallel infection of the same cells with TRA-dsGFP (data not shown). After infection, the cells will be stimulated with the anti-TCR antibody C305 for overnight and sorted for CD69 low and CD3+ phenotype by FACS. If the sorting gate was set to include the bottom 3% cells based on the single parameter of CD69 level, ⅔ cells in the sorting gate lacked TCR/CD3 complex, which explained their refractory to stimulation. The second parameter of CD3 expression was then incorporated. Even though there was a significant reduction of CD3/TCR complex on the surface following receptor-mediated internalization, the CD3− population was still distinguishable from the CD3+ population. The resulting sort gate contained 1% of the total cells, which translated into a 100-fold enrichment based on cell numbers. The recovered cells with CD69 low CD3+ phenotype were allowed to rest in complete medium for 5 days before being stimulated again for a new round of sorting. In subsequent round of sortings, the sort gate was always maintained to contain the equivalent of 1% of the unsorted control population. Obvious enrichment was achieved after 3 rounds of reiterative sorting. Cells with the desired phenotype increased from 1% to 22.3%. In addition, the overall population's geometric mean for CD69 was also reduced.

In order to ascertain that the phenotype was due to expression of the cDNA library rather than entirely due to spontaneous or retroviral insertion-mediated somatic mutation, the cells recovered after the third round of sorting were split into two halves. One half of the cells were grown in the absence of Dox while the other half in the presence of Dox. A week later, CD69 expression was compared following anti-TCR stimulation. There was a significant numbers of cells (11%) whose CD69 repression was lost in the presence of Dox, suggesting that the CD69 inhibition phenotype was indeed caused by the expression of library members. Single cell clones in conjunction with the fourth round of CD69 low CD3+ sorting (LLLL) were deposited.

In order to reduce the number of cells whose phenotype was not Dox-regulatable, the half of the cells grown in the presence of Dox were subjected to a fourth round of sorting for enrichment of CD69 high phenotype (LLLH). The cells recovered from LLLH sort were cultured in the absence of Dox for subsequence sorting and single cell cloning of CD69 low CD3+ phenotypes.

Dox regulation of CD69 expression was expressed as the ratio of geometric mean fluorescent intensity (GMFI) in the presence of Dox over that in the absence of Dox. In uninfected cells, Dox had limited effect on the induction of CD69 expression so that the ratio of GMFI (+Dox)/GMFI (−Dox) remained to be 1.00+/−0.25. The 2x standard deviation was therefore used as a cut-off criterion and clones with a ratio above 1.5 were regarded as Dox-regulated clones.

RNA samples were prepared from clones with Dox-regulatable phenotypes. Using primers specific for the vector sequence flanking the cDNA library insert, the cDNA insert of selected clones were captured by RT-PCR. Most clones generated only on DNA band, whereas a few clones generated two or more bands. Sequencing analysis revealed that the additional bands were caused by double or multiple insertions.

Characterization of proteins involved in T cell activation: Known TCR regulators such as Lck, ZAP70, PLCγ1 and Raf were obtained. In addition, the BCR regulator SYK was also uncovered. EDG1, a GPCR not previously known to be involved in B and T cell activation, was also identified using this assay (see FIGS. 14-32).

Lck is a non-receptor protein tyrosine kinase. Its role in T cell development and activation has been widely documented. So far, dominant negative form of Lck has no been reported. Our discovery that over expression of the kinase-truncated form of Lck caused inhibition of CD69, similar to the phenotype of Jurkat somatic mutant lacking Lck, suggests that kinase deletion of Lck could also work as a dominant negative form of Lck.

The two ZAP70 hits ended at aa 262 and 269, respectively. They both missed the catalytic domain. The deletions are very close to the positive control for the screen, ZAP70 SH2 (N+C), which ended at aa 276. Since ZAP70 SH2 (N+C) was shown to be a dominant negative protein, it appears that the two ZAP70 hits also behaved as dominant negative proteins of ZAP70.

SYK is a non-receptor tyrosine kinase belonging to the SYK/ZAP70 family of kinases. Since it has also been shown that the lack of SYK expression in Jurkat cells did not appear to significantly alter the TCR-mediated responses compared with Jurkat clones expressing SYK, it appears that the SYK hit obtained from our screen worked mainly to block ZAP70 function. SYK's similarity to ZAP70 and its ability to associate with phosphorylated TCR zeta chains also support this notion.

PLCγ1 plays a crucial role in coupling T cell receptor ligation to IL-2 gene expression in activated T lymphocytes. TCR engagement leads to rapid tyrosine phosphorylation and activation of PLCγ1. The activated enzyme converts phosphatidylinositol-4,5-bisphosphate (PIP2) to inositol-1,3,5-trisphosphate ((IP3) and diacylglycerol (DAG). IP3 triggers intracellular Ca2+ increase and DAG is a potent activator of protein kinase C (PKC). PLCγ1 has a split catalytic domain comprised of conserved X and Y subdomains. Single point mutation in the catalytic X box completely abolished the enzyme activity and also blocked IL-2 reporter gene expression when introduced into PLCγ-deficient Jurkat cells. Our hit contained the PH domain and the N and C terminal SH2 domains of PLCγ1. Significantly this hit also deleted the crucial tyrosine Y783 between the SH2 and SH3 domains. It was reported that Y783 was essential for coupling of TCR stimulation to IL-2 promoter activation and that mutation of Y783 to F (phenylalanine) generated a very potent dominant negative form of PLCγ1. Indeed, the original clone encoding the PLCγ1 hit had the highest Dox +/− ratio for CD69 expression among all clones from the cDNA screen, indicating the strong repression of CD69 induction by the hit as well as the total de-repression in the absence of the hit. When introduced to naive Jurkat cells, this fragment caused severe block of TCR-induced CD69 expression.

Raf is a MAP kinase kinase kinase. It interacts with Ras and leads to activation of the MAP kinase pathway. The Raf hit obtained also had a truncation of the kinase domain, creating a dominant negative form of the kinase. Other signaling molecules known to involve in TCR pathway were also discovered in our screen. They included PAG, CSK, SHP-1 and nucleolin.

Function in primary T lymphocytes: The relevance of the CD69 screen hits to physiological function of T cells was investigated in primary T lymphocytes. The hit was subcloned into a retroviral vector under a constitutively active promoter, followed by IRES-GFP. A protocol was also developed to couple successful retroviral infection to subsequence T cell activation. Primary T lymphocytes are at the quiescent stage when isolated from healthy donors. In order to be infected by retrovirus, primary lymphocytes need to be activated to progress in cell cycle. Fresh peripheral blood lymphocytes (PBL) contained typically T cells and B cells. The combined CD4+ and CD8+ cells represented total T cell percentage, which was 81% in this particular donor. The remaining 19% CD4-CD8-cells were B cells as stained by CD19 (data not shown). Upon culturing on anti-CD3 and anti-CD28 coated dishes, primary T lymphocytes were expanded and primary B cells and other cell types gradually died off in the culture. After infection, the culture contained virtually all T cells. Furthermore, primary T lymphocytes were successfully infected by retroviruses.

As seen with Jurkat cells (data not shown), GFP translated by way of IRES was not as abundant as GFP translated using the conventional Kozak sequence (comparing GFP geometric mean from CRU5-IRES-GFP and CRU5-GFP). Nevertheless the percentage infection remained similar. Insertion of a gene in front of IRES-GFP further reduced the expression level of GFP, which was observed with cell lines (data not shown) and here primary T lymphocytes. After allowing cells to rest following infection, FACS sorted cells were divided into two populations: GFP− and GFP+. The sorted cells were immediately put into culture. Anti-CD3 alone did not induce IL-2 production. This observation was consistent with previous report on freshly isolated primary T lymphocytes and confirmed the notion that prior culture and retroviral infection did not damage the physiological properties of these primary T lymphocytes. Addition of anti-CD28 in conjunction with anti-CD3 led to robust IL-2 production with vector-infected cells and the GFP− population of LckDN and PLCγ1 DN-infected cells. The GFP+ cell population from LckDN and PLCγ1DN-infected cells, however, were severely impaired in IL-2 production. As expect, the defect caused by LckDN and PLCγ1DN can be completely rescued by stimulation using PMA and ionomycin. Taken together, these results showed that Lck and PLCγ1 plays a role in IL-2 production from primary T lymphocytes, consistently with their involvement membrane proximal signaling events of T cell activation. These results also demonstrated a successful system to quickly validate hits from our functional genetic screens in primary cells.

Use of CD69 upregulation in drug screening: The discovery of important immune regulatory molecules from the B and T cell activation-induced CD69 upregulation validated the relevance of this cell-based assay. Essentially such a cell-based assay offers the opportunity to discover inhibitors of multiple targets such as Lck, ZAP70, PLCγ1, and EDG family proteins such as EDG1. It is the equivalent of multiplexing enzymatic assays with the additional advantage of cell permeability of compounds. It may even be possible to identify novel compounds that block adaptor protein functions. Towards this end, the FACS assay of cell surface CD69 expression was converted to a micro-titer plate based assay, for both T and B cell regulation assays.

In conclusion, the strategy presented in this study demonstrates a successful approach to discover and validate important immune regulators on a genome-wide scale. This approach, which requires no prior sequence information, provides a tool for functional cloning of regulators in numerous signal transduction pathways. For example, B cell activation-induced CD69 expression, IL-4-induced IgE class switch and TNF-induced NF-KB reporter gene expression are all amendable to the genetic perturbation following introduction of retroviral cDNA libraries. The outlined strategy is less biased compared to forced introduction of a handful of signaling molecules discovered in other context such as growth factor signal transduction. It also opens the door for discovering peptide inhibitors of immune modulatory proteins by screening random peptide libraries, including cyclic peptides, expressed from the retroviral vector.

C. Methods

Cell culture: Human Jurkat T cells (clone N) were routinely cultured in RPMI 1640 medium supplemented with 10% fetal calf serum (Hyclone), penicillin and streptamycin. Phoenix A cells were grown in DMEM supplemented with 10% fetal calf serum, penicillin and streptamycin. To produce the tTA-Jurkat cell line, Jurkat cells were infected with a retroviral construct which constitutively expresses the tetracycline transactivator protein and a reporter construct which expresses LyT2 driven by a tetracycline responsive element (TRE). The tTA-Jurkat cell population was optimized by sorting multiple sounds for high TRE-dependent expression of LyT2 in the absence of Dox and strong repression of LyT2 expression in the presence Dox. The cells were also sorted for maximal anti-TCR induced expression of CD69. Doxycycline was used at a final concentration of 10 ng/ml for at least 6 days to downregulate expression of cDNAs from the TRE promoter.

Transfection and infection: Phoenix A packaging cells were transfected with retroviral vectors using calcium phosphate for 6 hours as standard protocols. After 24 hours, supernatant was replaced with complete RPMI medium and virus was allowed to accumulate for an additional 24 hours. Viral supernatant was collected, filtered through a 0.2 μM filter and mixed with Jurkat cells at a density of $2.5 \times 10^5$ cells/ml. Cells were spun at room temperature for 3 hours at 3000 rpm, followed by overnight incubation at 37° C. Transfection and infection efficiencies were monitored by GFP expression and functional analysis was carried out 2-4 days after infection.

Libraries: RNA extracted from human lymph node, thymus, spleen and bone marrow was used to produce two cDNA libraries; one random primed and directionally cloned and the second non-directionally cloned and provided with 3 exogenous ATG in 3 frames. cDNAs were cloned into the pTRA-exs vector giving robust doxycycline-regulable transcription of cDNAs from the TRE promoter. The total combined library complexity was 5×10⁷ independent clones.

Stimulation: For CD69 upregulation experiments, tTA-Jurkat cells were split to 2.5×10⁵ cells/ml 24 hours prior to stimulation. Cells were spun and resuspended at 5×10⁵ cells/ml in fresh complete RPMI medium in the presence of 100 ng/ml C305 (anti-Jurkat clonotypic TCR) or 5 ng/ml PMA hybridoma supernatant for 20-26 hours at 37° C., and then assayed for surface CD69 expression.

Cell surface marker analysis: Jurkat-N cells were stained with an APC-conjugated mouse monoclonal anti-human CD69 antibody (Caltag) at 4° C. for 20 minutes and analyzed using a Facscalibur instrument (Becton Dickinson) with Cellquest software. Cell sorts were performed on a MoFlo (Cytomation).

cDNA screen: Phoenix A packaging cells were transfected with a mixture of the two tTA regulated retroviral pTRA-exs cDNA libraries. Supernatant containing packaged viral particles was used to infect tTA-Jurkat cells with an efficiency of ~85%. After 4 days of cDNA expression, library infected cells were stimulated with 0.3 µg/ml C305 for 20-26 hours, stained with APC-conjugated anti-CD69, and lowest CD69-expressing cells still expressing CD3 (CD69$^{low}$CD3$^+$) were isolated using a fluorescence activated cell sorter. Sorting was repeated over multiple rounds with a 6-day rest period between stimulations until the population was significantly enriched for non-responders. Single cells were deposited from 4 separate rounds of sorting. Cell clones were expanded in the presence and absence of Dox, stimulated and analyzed for CD69 upregulation.

Isolation of cDNA inserts: PCR primers were designed to amplify cDNA inserts from both libraries and did not amplify Lyt2 that was also under TRE regulation. The primers used contained flanking BstXI sites for subsequent cloning to pTRA-IRES-GFP vector. RT-PCR cloning was achieved with kits from Clontech or Life Technologies. The gel-purified RT-PCR products were submitted for sequencing directly and simultaneously digested for subcloning. Dominant negative ZAP70 (KI) and ZAP70SH2 (N+C) as well as selected hits from cDNA screens were subcloned to the retroviral pTRA-TRES-GFP vector. Selected hits form cDNA screens were also subcloned to CRU5-IRES-GFP for infection of human primary T lymphocytes and examination of IL-2 production.

Example 2

Identification of Additional EDG Family Genes Involved in Modulation of T Cell Activation Using the CD69 lymphocyte activation assays and other methods described in Example 1, nucleic acids encoding EDG 2-8 are tested, and EDG2-8 are identified as proteins involved in modulation of lymphocyte activation. Wild-type EDG 2-8 nucleotide sequences are described herein. EDG 2-8 are therefore useful in assays to identify compounds that modulate lymphocyte activation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that modulates EDG-modulated lymphocyte activation, the method comprising the steps of:
   (i) contacting a lymphocyte comprising a recombinant EDG polypeptide with the compound, the EDG polypeptide having at least 95% identity to an amino acid sequence of SEQ ID NO:5 and further wherein the EDG polypeptide inhibits lymphocyte activation-induced upregulation of CD69 expression;
   (ii) stimulating a T cell receptor or a B cell receptor on said lymphocyte, thereby activating the lymphocyte; and
   (iii) determining the effect of the compound upon EDG-modulated activation of the activated lymphocyte comprising the EDG polypeptide in comparison to an activated lymphocyte comprising a recombinant EDG polypeptide not contacted by the compound, thereby identifying a compound that modulates EDG-modulated lymphocyte activation.

2. The method of claim 1, wherein the lymphocyte is a B lymphocyte.

3. The method of claim 2, wherein the lymphocyte is a cultured B lymphocyte.

4. The method of claim 3, wherein the lymphocyte is a BJAB cell.

5. The method of claim 1, wherein the lymphocyte is a T lymphocyte.

6. The method of claim 5, wherein the lymphocyte is primary T lymphocyte.

7. The method of claim 5, wherein the lymphocyte is a cultured T lymphocyte.

8. The method of claim 7, wherein the lymphocyte is a Jurkat cell.

9. The method of claim 1, wherein the effect on lymphocyte activation is determined by measuring CD69 expression, IL-2 production, intracellular $Ca^{2+}$ mobilization, or lymphocyte proliferation.

10. The method of claim 1, wherein modulation is potentiated inhibition of lymphocyte activation by an EDG agonist.

11. The method of claim 10, wherein modulation is potentiated inhibition of T lymphocyte activation by an EDG agonist.

12. The method of claim 10, wherein modulation is potentiated inhibition of B lymphocyte activation by an EDG agonist.

13. The method of claim 1, wherein the EDG polypeptide is an EDG-1 polypeptide encoded by a nucleic acid comprising a sequence of SEQ ID NO:1.

14. The method of claim 1, wherein the compound is an antibody.

15. The method of claim 1, wherein the compound is an antisense molecule.

16. The method of claim 1, wherein the compound is a small organic molecule.

17. The method of claim 1, wherein the compound is a sphingolipid.

18. The method of claim 1, wherein the compound is a sphingolipid analog.

19. The method of claim 18, wherein the compound is a synthetic sphingolipid analog.

20. The method of claim 18, wherein the compound is a naturally occurring sphingolipid analog.

21. The method of claim 1, wherein the EDG polypeptide comprises an amino acid sequence of SEQ ID NO:5.

22. The method of claim 1, wherein the lymphocyte is activated using an antigen.

23. The method of claim 22, wherein the antigen is an antibody directed to the T cell receptor or the B cell receptor.

* * * * *

SEQUENCE LISTING

<160> NUMBER OF SEQ ID NOS: 15

<210> SEQ ID NO 1
<211> LENGTH: 1149
<212> TYPE: DNA
<213> ORGANISM: Homo sapiens
<220> FEATURE:
<223> OTHER INFORMATION: wild-type human endothelial differentiation
      G-protein coupled receptor (GPCR) 1 (EDG1)
<220> FEATURE:
<221> NAME/KEY: CDS
<222> LOCATION: (1)..(1149)
<223> OTHER INFORMATION: wild type human EDG1

<400> SEQUENCE: 1
atggggccca ccagcgtccc gctggtcaag gcccaccgca gctcggtctc tgactacgtc      60
aactatgata tcatcgtccg gcattacaac tacacgggaa agctgaatat cagcgcggac     120
aaggagaaca gcattaaact gacctcggtg gtgttcattc tcatctgctg ctttatcatc     180
ctggagaaca tctttgtctt gctgaccatt tggaaaacca agaaattcca ccgacccatg     240
tactatttta ttggcaatct ggccctctca gacctgttgg caggagtagc ctacacagct     300
aacctgctct tgtctggggc caccacctac aagctcactc ccgcccagtg gtttctgcgg     360
gaagggagta tgtttgtggc cctgtcagcc tccgtgttca gtctcctcgc catcgccatt     420
gagcgctata tcacaatgct gaaaatgaaa ctccacaacg ggagcaataa cttccgcctc     480
ttcctgctaa tcagcgcctg ctgggtcatc tccctcatcc tgggtggcct gcctatcatg     540
ggctggaact gcatcagtgc gctgtccagc tgctccaccg tgctgccgct ctaccacaag     600

| | |
|---|---|
| cactatatcc tcttctgcac cacggtcttc actctgcttc tgctctccat cgtcattctg | 660 |
| tactgcagaa tctactcctt ggtcaggact cggagccgcc gcctgacgtt ccgcaagaac | 720 |
| atttccaagg ccagccgcag ctctgagaag tcgctggcgc tgctcaagac cgtaattatc | 780 |
| gtcctgagcg tcttcatcgc ctgctgggca ccgctcttca tcctgctcct gctggatgtg | 840 |
| ggctgcaagg tgaagacctg tgacatcctc ttcagagcgg agtacttcct ggtgttagct | 900 |
| gtgctcaact ccggcaccaa ccccatcatt tacactctga ccaacaagga gatgcgtcgg | 960 |
| gccttcatcc ggatcatgtc ctgctgcaag tgcccgagcg agactctgc tggcaaattc | 1020 |
| aagcgaccca tcatcgccgg catggaattc agccgcagca atcggacaa ttcctcccac | 1080 |
| ccccagaaag acgaagggga caacccagag accattatgt cttctggaaa cgtcaactct | 1140 |
| tcttcctag | 1149 |

<210> SEQ ID NO 2
<211> LENGTH: 1032
<212> TYPE: DNA
<213> ORGANISM: Homo sapiens
<220> FEATURE:
<223> OTHER INFORMATION: mutant #1, C-terminally truncated variant of
      human endothelial differentiation G-protein
      coupled receptor (GPCR) 1 (EDG1)
<220> FEATURE:
<221> NAME/KEY: CDS
<222> LOCATION: (9)..(1031)
<223> OTHER INFORMATION: mutant #1 human EDG1

<400> SEQUENCE: 2

| | |
|---|---|
| ttggcaccat ggggcccacc agcgtcccgc tggtcaaggc ccaccgcagc tcggtctctg | 60 |
| actacgtcaa ctatgatatc atcgtccggc attacaacta cacgggaaag ctgaatatca | 120 |
| gcgcggacaa ggagaacagc attaaactga cctcggtggt gttcattctc atctgctgct | 180 |
| ttatcatcct ggagaacatc tttgtcttgc tgaccatttg gaaaaccaag aaattccacc | 240 |
| gacccatgta ctattttatt ggcaatctgg ccctctcaga cctgttggca ggagtagcct | 300 |
| acacagctaa cctgctcttg tctggggcca ccacctacaa gctcactccc gcccagtggt | 360 |
| ttctgcggga agggagtatg tttgtggccc tgtcagcctc cgtgttcagt ctcctcgcca | 420 |
| tcgccattga gcgctatatc acaatgctga aaatgaaact ccacaacggg agcaataact | 480 |
| tccgcctctt cctgctaatc agcgcctgct gggtcatctc cctcatcctg ggtggcctgc | 540 |
| ctatcatggg ctggaactgc atcagtgcgc tgtccagctg ctccaccgtg ctgccgctct | 600 |
| accacaagca ctatatcctc ttctgcacca cggtcttcac tctgcttctg ctctccatcg | 660 |
| tcattctgta ctgcagaatc tactccttgg tcaggactcg gagccgccgc ctgacgttcc | 720 |
| gcaagaacat ttccaaggcc agccgcagct ctgagaagtc gctggcgctg ctcaagaccg | 780 |
| taattatcgt cctgagcgtc ttcatcgcct gctgggcacc gctcttcatc ctgctcctgc | 840 |
| tggatgtggg ctgcaaggtg aagacctgtg acatcctctt cagagcggag tacttcctgg | 900 |
| tgttagctgt gctcaactcc ggcaccaacc ccatcattta cactctgacc aacaaggaga | 960 |
| tgcgtcgggc cttcatccgg atcatgtcct gctgcaagtg cccgagcgga gactctgctg | 1020 |
| gcaaattcaa gc | 1032 |

<210> SEQ ID NO 3
<211> LENGTH: 1437
<212> TYPE: DNA
<213> ORGANISM: Homo sapiens
<220> FEATURE:

```
<223> OTHER INFORMATION: mutant #2, C-terminally truncated variant of
      human endothelial differentiation G-protein
      coupled receptor (GPCR) 1 (EDG1)
<220> FEATURE:
<221> NAME/KEY: CDS
<222> LOCATION: (495)..(1436)
<223> OTHER INFORMATION: mutant #2 human EDG1

<400> SEQUENCE: 3
gcggccgcgt cgacgtgcgt ctcagcagtt cagatccggg ggcccccagc tgacagaggg      60 cgtgggggt taaggcatta acccctccca gcctcttcct gaagaaacca cccagccttg     120
gcgcggcgct gggtgacttc gcgtagcagg cagggaactg gccgcggcga gcgggactgg    180
ccattggagt gctccgctgc ggagggaggg gaccccgact cgagtaagtt tgcgagagca    240
ctacgcagtc agtcggggc agcagcaaga tgcgaagcga gccgtacaga tcccgggctc     300
tccgaacgca acttcgccct gcttgagcga ggctgcggtt ccgaggccc tctccagcca     360 aggaaaagct acacaaaaag cctggatcac tcatcgaacc accctgaag ccagtgaagg     420 ctctctcgcc tcgccctcta gcgttcgtct ggagtagcgc caccccggct tcctggggac    480
acagggttgg caccatgggg cccaccagcg tcccgctggt caaggcccac cgcagctcgg    540
tctctgacta cgtcaactat gatatcatcg tccggcatta caactacacg ggaaagctga    600
atatcagcgc ggacaaggag aacagcatta aactgacctc ggtggtgttc attctcatct    660
gctgctttat catcctggag aacatctttg tcttgctgac catttggaaa accaagaaat    720
tccaccgacc catgtactat tttattggca atctggccct ctcagacctg ttggcaggag    780
tagcctacac agctaacctg ctcttgtctg ggccaccac ctacaagctc actcccgccc     840
agtggtttct gcgggaaggg agtatgtttg tggccctgtc agcctccgtg ttcagtctcc    900
tcgccatcgc cattgagcgc tatatcacaa tgctgaaaat gaaactccac aacgggagca    960
ataacttccg cctcttcctg ctaatcagcg cctgctgggt catctccctc atcctgggtg   1020
gcctgcctat catgggctgg aactgcatca gtgcgctgtc cagctgctcc accgtgctgc   1080
cgctctacca caagcactat atcctcttct gcaccacggt cttcactctg cttctgctct   1140
ccatcgtcat tctgtactgc agaatctact ccttggtcag gactcggagc cgccgcctga   1200
cgttccgcaa gaacatttcc aaggccagcc gcagctctga aagtcgctg gcgctgcta    1260 agaccgtaat tatcgtcctg agcgtcttca tcgcctgctg gcaccgctc ttcatcctgc     1320 tcctgctgga tgtgggctgc aaggtgaaga cctgtgacat cctcttcaga gcggagtact   1380
tcctggtgtt agctgtgctc aactccggca ccaaccccat catttacact ctgacca      1437

<210> SEQ ID NO 4
<211> LENGTH: 1376
<212> TYPE: DNA
<213> ORGANISM: Homo sapiens
<220> FEATURE:
<223> OTHER INFORMATION: mutant #3, C-terminally truncated variant of
      human endothelial differentiation G-protein
      coupled receptor (GPCR) 1 (EDG1)
<220> FEATURE:
<221> NAME/KEY: CDS
<222> LOCATION: (338)..(1375)
<223> OTHER INFORMATION: mutant #3 human EDG1

<400> SEQUENCE: 4
ggcacgaggc gagcgggact ggccattgga gtgctccgct gcggagggag gggaccccgt     60
actcgagtaa gtttgcgaga gcactacgca gtcagtcggg ggcagcagca agatgcgaag    120
cgagccgtac agatcccggg ctctccgaac gcaacttcgc cctgcttgag cgaggccgcg    180
```

-continued

```
gtttccgagg ccctctccag ccaaggaaaa gctacacaaa aagcctggat cactcatcga    240
accacccctg aagccagtga aggctctctc gcctcgccct ctagcgttcg tctggagtag    300
cgccaccccg gcttcctggg gacacagggt tggcaccatg gggcccacca gcgtcccgct    360
ggtcaaggcc caccgcagct cggtctctga ctacgtcaac tatgatatca tcgtccggca    420
ttacaactac acgggaaagc cgaatatcag cgcggacaag gagaacagca ttaaactgac    480
ctcggtggtg ttcattctca tctgctgctt tatcatcctg gagaacatct ttgtcttgct    540
gaccatttgg aaaaccaaga aattccaccg acccatgtac tatttttattg caatctggc     600 cctctcagac ctgttggcag gagtagccta cacagctaac ctgctcttgt ctggggccac    660
cacctacaag ctcactcccg cccagtggtt tctgcgggaa gggagtatgt ttgtggccct    720
gtcagcctcc gtgttcagtc tcctcgccat cgccattgag cgctatatca caatgctgaa    780
aatgaaactc cacaacggga gcaataactt ccgcctcttc ctgctaatca gcgcctgctg    840
ggtcatctcc ctcatcctgg gtggcctgcc tatcatgggc tggaactgca tcagtgcgct    900
gtccagctgc tccaccgtgc tgccgctcta ccacaagcac tatatcctct tctgcaccac    960
ggtcttcact ctgcttctgc tctccatcgt cattctgtac tgcagaatct actccttggt    1020
caggactcgg agccgccgcc tgacgttccg caagaacatt tccaaggcca gccgcagctc    1080
tgagaagtcg ctggcgctgc tcaggaccgt aattatcgtc ctgagcgtct tcatcgcctg    1140
ctgggcaccg ctcttcatcc tgctcctgct ggatgtgggc tgcaaggtga agacctgtga    1200
catcctcttc agagcggagt acttcctggt gttagctgtg ctcaactccg gcaccaaccc    1260
catcatttac actctgacca acaaggagat gcgtcgggcc ttcatccgga tcatgtcctg    1320
ctgcaagtgc ccgagcggag actctgctgg caaattcaag cgacccatca tcgccg        1376
```

<210> SEQ ID NO 5
<211> LENGTH: 382
<212> TYPE: PRT
<213> ORGANISM: Homo sapiens
<220> FEATURE:
<223> OTHER INFORMATION: wild-type human endothelial differentiation
      G-protein coupled receptor (GPCR) 1 (EDG1)

<400> SEQUENCE: 5

```
Met Gly Pro Thr Ser Val Pro Leu Val Lys Ala His Arg Ser Ser Val
 1               5                  10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140
```

```
Thr Met Leu Lys Met Lys Leu His Asn Gly Ser Asn Phe Arg Leu
145                 150                 155                 160

Phe Leu Leu Ile Ser Ala Cys Trp Val Ile Ser Leu Ile Leu Gly Gly
            165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
            195                 200                 205

Val Phe Thr Leu Leu Leu Ser Ile Val Ile Leu Tyr Cys Arg Ile
        210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Val Lys Thr Cys Asp
        275                 280                 285

Ile Leu Phe Arg Ala Glu Tyr Phe Leu Val Leu Ala Val Leu Asn Ser
290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
            340                 345                 350

Ser Lys Ser Asp Asn Ser Ser His Pro Gln Lys Asp Glu Gly Asp Asn
            355                 360                 365

Pro Glu Thr Ile Met Ser Ser Gly Asn Val Asn Ser Ser Ser
            370                 375                 380

<210> SEQ ID NO 6
<211> LENGTH: 364
<212> TYPE: PRT
<213> ORGANISM: Homo sapiens
<220> FEATURE:
<223> OTHER INFORMATION: human endothelial differentiation G-protein
      coupled receptor (GPCR) 2 (EDG2)

<400> SEQUENCE: 6

Met Ala Ala Ile Ser Thr Ser Ile Pro Val Ile Ser Gln Pro Gln Phe
1               5                   10                  15

Thr Ala Met Asn Glu Pro Gln Cys Phe Tyr Asn Glu Ser Ile Ala Phe
            20                  25                  30

Phe Tyr Asn Arg Ser Gly Lys His Leu Ala Thr Glu Trp Asn Thr Val
        35                  40                  45

Ser Lys Leu Val Met Gly Leu Gly Ile Thr Val Cys Ile Phe Ile Met
    50                  55                  60

Leu Ala Asn Leu Leu Val Met Val Ala Ile Tyr Val Asn Arg Arg Phe
65                  70                  75                  80

His Phe Pro Ile Tyr Tyr Leu Met Ala Asn Leu Ala Ala Ala Asp Phe
                85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
        115                 120                 125
```

```
Asp Thr Ser Leu Thr Ala Ser Val Ala Asn Leu Leu Ala Ile Ala Ile
    130                 135                 140

Glu Arg His Ile Thr Val Phe Arg Met Gln Leu His Thr Arg Met Ser
145                 150                 155                 160

Asn Arg Arg Val Val Val Ile Val Val Ile Trp Thr Met Ala Ile
                165                 170                 175

Val Met Gly Ala Ile Pro Ser Val Gly Trp Asn Cys Ile Cys Asp Ile
            180                 185                 190

Glu Asn Cys Ser Asn Met Ala Pro Leu Tyr Ser Asp Ser Tyr Leu Val
        195                 200                 205

Phe Trp Ala Ile Phe Asn Leu Val Thr Phe Val Val Met Val Val Leu
    210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255

Leu Lys Thr Val Val Ile Val Leu Gly Ala Phe Ile Ile Cys Trp Thr
            260                 265                 270

Pro Gly Leu Val Leu Leu Leu Leu Asp Val Cys Cys Pro Gln Cys Asp
        275                 280                 285

Val Leu Ala Tyr Glu Lys Phe Phe Leu Leu Leu Ala Glu Phe Asn Ser
    290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Ser Glu Asn Pro Thr Gly
                325                 330                 335

Pro Thr Glu Ser Ser Asp Arg Ser Ala Ser Ser Leu Asn His Thr Ile
            340                 345                 350

Leu Ala Gly Val His Ser Asn Asp His Ser Val Val
        355                 360

<210> SEQ ID NO 7
<211> LENGTH: 378
<212> TYPE: PRT
<213> ORGANISM: Homo sapiens
<220> FEATURE:
<223> OTHER INFORMATION: human endothelial differentiation G-protein
      coupled receptor (GPCR) 3 (EDG3)

<400> SEQUENCE: 7

Met Ala Thr Ala Leu Pro Pro Arg Leu Gln Pro Val Arg Gly Asn Glu
1               5                   10                  15

Thr Leu Arg Glu His Tyr Gln Tyr Val Gly Lys Leu Ala Gly Arg Leu
            20                  25                  30

Lys Glu Ala Ser Glu Gly Ser Thr Leu Thr Thr Val Leu Phe Leu Val
        35                  40                  45

Ile Cys Ser Phe Ile Val Leu Glu Asn Leu Met Val Leu Ile Ala Ile
    50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
```

-continued

```
            115                 120                 125
Leu Leu Ala Ile Ala Ile Glu Arg His Leu Thr Met Ile Lys Met Arg
    130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
                180                 185                 190

Ser Lys Lys Tyr Ile Ala Phe Cys Ile Ser Ile Phe Thr Ala Ile Leu
                195                 200                 205

Val Thr Ile Val Ile Leu Tyr Ala Arg Ile Tyr Phe Leu Val Lys Ser
    210                 215                 220

Ser Ser Arg Lys Val Ala Asn His Asn Asn Ser Glu Arg Ser Met Ala
225                 230                 235                 240

Leu Leu Arg Thr Val Val Ile Val Val Ser Val Phe Ile Ala Cys Trp
                245                 250                 255

Ser Pro Leu Phe Ile Leu Phe Leu Ile Asp Val Ala Cys Arg Val Gln
                260                 265                 270

Ala Cys Pro Ile Leu Phe Lys Ala Gln Trp Phe Ile Val Leu Ala Val
    275                 280                 285

Leu Asn Ser Ala Met Asn Pro Val Ile Tyr Thr Leu Ala Ser Lys Glu
    290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Asn Asn Ser Ser His Ser Pro Lys Val Lys
                340                 345                 350

Glu Asp Leu Pro His Thr Asp Pro Ser Ser Cys Ile Met Asp Lys Asn
    355                 360                 365

Ala Ala Leu Gln Asn Gly Ile Phe Cys Asn
    370                 375
```

<210> SEQ ID NO 8
<211> LENGTH: 351
<212> TYPE: PRT
<213> ORGANISM: Homo sapiens
<220> FEATURE:
<223> OTHER INFORMATION: human endothelial differentiation G-protein
      coupled receptor (GPCR) 4 (EDG4)

<400> SEQUENCE: 8

```
Met Val Ile Met Gly Gln Cys Tyr Tyr Asn Glu Thr Ile Gly Phe Phe
  1               5                  10                  15

Tyr Asn Asn Ser Gly Lys Glu Leu Ser Ser His Trp Arg Pro Lys Asp
                 20                  25                  30

Val Val Val Val Ala Leu Gly Leu Thr Val Ser Val Leu Val Leu Leu
             35                  40                  45

Thr Asn Leu Leu Val Ile Ala Ala Ile Ala Ser Asn Arg Arg Phe His
         50                  55                  60

Gln Pro Ile Tyr Tyr Leu Leu Gly Asn Leu Ala Ala Ala Asp Leu Phe
 65                  70                  75                  80

Ala Gly Val Ala Tyr Leu Phe Leu Met Phe His Thr Gly Pro Arg Thr
                 85                  90                  95
```

```
Ala Arg Leu Ser Leu Glu Gly Trp Phe Leu Arg Gln Gly Leu Leu Asp
            100                 105                 110
Thr Ser Leu Thr Ala Ser Val Ala Thr Leu Leu Ala Ile Ala Val Glu
            115                 120                 125
Arg His Arg Ser Val Met Ala Val Gln Leu His Ser Arg Leu Pro Arg
            130                 135                 140
Gly Arg Val Val Met Leu Ile Val Gly Val Trp Val Ala Ala Leu Gly
145                 150                 155                 160
Leu Gly Leu Leu Pro Ala His Ser Trp His Cys Leu Cys Ala Leu Asp
                165                 170                 175
Arg Cys Ser Arg Met Ala Pro Leu Leu Ser Arg Ser Tyr Leu Ala Val
            180                 185                 190
Trp Ala Leu Ser Ser Leu Leu Val Phe Leu Leu Met Val Ala Val Tyr
            195                 200                 205
Thr Arg Ile Phe Phe Tyr Val Arg Arg Arg Val Gln Arg Met Ala Glu
            210                 215                 220
His Val Ser Cys His Pro Arg Tyr Arg Glu Thr Thr Leu Ser Leu Val
225                 230                 235                 240
Lys Thr Val Val Ile Ile Leu Gly Ala Phe Val Val Cys Trp Thr Pro
                245                 250                 255
Gly Gln Val Val Leu Leu Leu Asp Gly Leu Gly Cys Glu Ser Cys Asn
            260                 265                 270
Val Leu Ala Val Glu Lys Tyr Phe Leu Leu Leu Ala Glu Ala Asn Ser
            275                 280                 285
Leu Val Asn Ala Ala Val Tyr Ser Cys Arg Asp Ala Glu Met Arg Arg
            290                 295                 300
Thr Phe Arg Arg Leu Leu Cys Cys Ala Cys Leu Arg Gln Ser Thr Arg
305                 310                 315                 320
Glu Ser Val His Tyr Thr Ser Ser Ala Gln Gly Gly Ala Ser Thr Arg
                325                 330                 335
Ile Met Leu Pro Glu Asn Gly His Pro Leu Met Asp Ser Thr Leu
            340                 345                 350

<210> SEQ ID NO 9
<211> LENGTH: 353
<212> TYPE: PRT
<213> ORGANISM: Homo sapiens
<220> FEATURE:
<223> OTHER INFORMATION: human endothelial differentiation G-protein
      coupled receptor (GPCR) 5 (EDG5)

<400> SEQUENCE: 9

Met Gly Ser Leu Tyr Ser Glu Tyr Leu Asn Pro Asn Lys Val Gln Glu
1               5                   10                  15
His Tyr Asn Tyr Thr Lys Glu Thr Leu Glu Thr Gln Glu Thr Thr Ser
            20                  25                  30
Arg Gln Val Ala Ser Ala Phe Ile Val Ile Leu Cys Cys Ala Ile Val
            35                  40                  45
Val Glu Asn Leu Leu Val Leu Ile Ala Val Ala Arg Asn Ser Lys Phe
        50                  55                  60
His Ser Ala Met Tyr Leu Phe Leu Gly Asn Leu Ala Ala Ser Asp Leu
65              70                  75                  80
Leu Ala Gly Val Ala Phe Val Ala Asn Thr Leu Leu Ser Gly Ser Val
                85                  90                  95
Thr Leu Arg Leu Thr Pro Val Gln Trp Phe Ala Arg Glu Gly Ser Ala
            100                 105                 110
```

```
Ser Ile Thr Leu Ser Ala Ser Val Phe Ser Leu Leu Ala Ile Ala Ile
            115                 120                 125

Glu Arg His Val Ala Ile Ala Lys Val Lys Leu Tyr Gly Ser Asp Lys
        130                 135                 140

Ser Cys Arg Met Leu Leu Ile Gly Ala Ser Trp Leu Ile Ser Leu
145                 150                 155                 160

Val Leu Gly Gly Leu Pro Ile Leu Gly Trp Asn Cys Leu Gly His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Ile Ile Leu Leu Ala Ile Val Ala Leu
        195                 200                 205

Tyr Val Arg Ile Tyr Cys Val Arg Ser Ser His Ala Asp Met Ala
    210                 215                 220

Ala Pro Gln Thr Leu Ala Leu Leu Lys Thr Val Thr Ile Val Leu Gly
225                 230                 235                 240

Val Phe Ile Val Cys Trp Leu Pro Ala Phe Ser Ile Leu Leu Leu Asp
                245                 250                 255

Tyr Ala Cys Pro Val His Ser Cys Pro Ile Leu Tyr Lys Ala His Tyr
            260                 265                 270

Phe Phe Ala Val Ser Thr Leu Asn Ser Leu Leu Asn Pro Val Ile Tyr
        275                 280                 285

Thr Trp Arg Ser Arg Asp Leu Arg Arg Glu Val Leu Arg Pro Leu Gln
    290                 295                 300

Cys Trp Arg Pro Gly Val Gly Val Gln Gly Arg Arg Arg Val Gly Thr
305                 310                 315                 320

Pro Gly His His Leu Leu Pro Leu Arg Ser Ser Ser Leu Glu Arg
                325                 330                 335

Gly Met His Met Pro Thr Ser Pro Thr Phe Leu Glu Gly Asn Thr Val
            340                 345                 350

Val

<210> SEQ ID NO 10
<211> LENGTH: 384
<212> TYPE: PRT
<213> ORGANISM: Homo sapiens
<220> FEATURE:
<223> OTHER INFORMATION: human endothelial differentiation G-protein
      coupled receptor (GPCR) 6 (EDG6)

<400> SEQUENCE: 10

Met Asn Ala Thr Gly Thr Pro Val Ala Pro Glu Ser Cys Gln Gln Leu
1               5                   10                  15

Ala Ala Gly Gly His Ser Arg Leu Ile Val Leu His Tyr Asn His Ser
                20                  25                  30

Gly Arg Leu Ala Gly Arg Gly Gly Pro Glu Asp Gly Gly Leu Gly Ala
            35                  40                  45

Leu Arg Gly Leu Ser Val Ala Ala Ser Cys Leu Val Val Leu Glu Asn
        50                  55                  60

Leu Leu Val Leu Ala Ala Ile Thr Ser His Met Arg Ser Arg Arg Trp
65                  70                  75                  80

Val Tyr Tyr Cys Leu Val Asn Ile Thr Leu Ser Asp Leu Leu Thr Gly
                85                  90                  95

Ala Ala Tyr Leu Ala Asn Val Leu Leu Ser Gly Ala Arg Thr Phe Arg
            100                 105                 110
```

```
Leu Ala Pro Ala Gln Trp Phe Leu Arg Glu Gly Leu Leu Phe Thr Ala
            115                 120                 125
Leu Ala Ala Ser Thr Phe Ser Leu Leu Phe Thr Ala Gly Glu Arg Phe
130                 135                 140
Ala Thr Met Val Arg Pro Val Ala Glu Ser Gly Ala Thr Lys Thr Ser
145                 150                 155                 160
Arg Val Tyr Gly Phe Ile Gly Leu Cys Trp Leu Leu Ala Ala Leu Leu
                165                 170                 175
Gly Met Leu Pro Leu Leu Gly Trp Asn Cys Leu Cys Ala Phe Asp Arg
            180                 185                 190
Cys Ser Ser Leu Leu Pro Leu Tyr Ser Lys Arg Tyr Ile Leu Phe Cys
            195                 200                 205
Leu Val Ile Phe Ala Gly Val Leu Ala Thr Ile Met Gly Leu Tyr Gly
        210                 215                 220
Ala Ile Phe Arg Leu Val Gln Ala Ser Gly Gln Lys Ala Pro Arg Pro
225                 230                 235                 240
Ala Ala Arg Arg Lys Ala Arg Arg Leu Leu Lys Thr Val Leu Met Ile
                245                 250                 255
Leu Leu Ala Phe Leu Val Cys Trp Gly Pro Leu Phe Gly Leu Leu Leu
            260                 265                 270
Ala Asp Val Phe Gly Ser Asn Leu Trp Ala Gln Glu Tyr Leu Arg Gly
            275                 280                 285
Met Asp Trp Ile Leu Ala Leu Ala Val Leu Asn Ser Ala Val Asn Pro
        290                 295                 300
Ile Ile Tyr Ser Phe Arg Ser Arg Glu Val Cys Arg Ala Val Leu Ser
305                 310                 315                 320
Phe Leu Cys Cys Gly Cys Leu Arg Leu Gly Met Arg Gly Pro Gly Asp
                325                 330                 335
Cys Leu Ala Arg Ala Val Glu Ala His Ser Gly Ala Ser Thr Thr Asp
            340                 345                 350
Ser Ser Leu Arg Pro Arg Asp Ser Phe Arg Gly Ser Arg Ser Leu Ser
            355                 360                 365
Phe Arg Met Arg Glu Pro Leu Ser Ser Ile Ser Ser Val Arg Ser Ile
        370                 375                 380

<210> SEQ ID NO 11
<211> LENGTH: 353
<212> TYPE: PRT
<213> ORGANISM: Homo sapiens
<220> FEATURE:
<223> OTHER INFORMATION: human endothelial differentiation G-protein
      coupled receptor (GPCR) 7 (EDG7)

<400> SEQUENCE: 11

Met Asn Glu Cys His Tyr Asp Lys His Met Asp Phe Phe Tyr Asn Arg
1               5                   10                  15
Ser Asn Thr Asp Thr Val Asp Asp Trp Thr Gly Thr Lys Leu Val Ile
            20                  25                  30
Val Leu Cys Val Gly Thr Phe Phe Cys Leu Phe Ile Phe Phe Ser Asn
        35                  40                  45
Ser Leu Val Ile Ala Ala Val Ile Lys Asn Arg Lys Phe His Phe Pro
    50                  55                  60
Phe Tyr Tyr Leu Leu Ala Asn Leu Ala Ala Ala Asp Phe Phe Ala Gly
65                  70                  75                  80
Ile Ala Tyr Val Phe Leu Met Phe Asn Thr Gly Pro Val Ser Lys Thr
```

```
                    85                  90                  95
Leu Thr Val Asn Arg Trp Phe Leu Arg Gln Gly Leu Leu Asp Ser Ser
                100                 105                 110

Leu Thr Ala Ser Leu Thr Asn Leu Leu Val Ile Ala Val Glu Arg His
                115                 120                 125

Met Ser Ile Met Arg Met Arg Val His Ser Asn Leu Thr Lys Lys Arg
            130                 135                 140

Val Thr Leu Leu Ile Leu Leu Val Trp Ala Ile Ala Ile Phe Met Gly
145                 150                 155                 160

Ala Val Pro Thr Leu Gly Trp Asn Cys Leu Cys Asn Ile Ser Ala Cys
                165                 170                 175

Ser Ser Leu Ala Pro Ile Tyr Ser Arg Ser Tyr Leu Val Phe Trp Thr
                180                 185                 190

Val Ser Asn Leu Met Ala Phe Leu Ile Met Val Val Val Tyr Leu Arg
            195                 200                 205

Ile Tyr Val Tyr Val Lys Arg Lys Thr Asn Val Leu Ser Pro His Thr
        210                 215                 220

Ser Gly Ser Ile Ser Arg Arg Arg Thr Pro Met Lys Leu Met Lys Thr
225                 230                 235                 240

Val Met Thr Val Leu Gly Ala Phe Val Val Cys Trp Thr Pro Gly Leu
                245                 250                 255

Val Val Leu Leu Leu Asp Gly Leu Asn Cys Arg Gln Cys Gly Val Gln
                260                 265                 270

His Val Lys Arg Trp Phe Leu Leu Leu Ala Leu Leu Asn Ser Val Val
            275                 280                 285

Asn Pro Ile Ile Tyr Ser Tyr Lys Asp Glu Asp Met Tyr Gly Thr Met
290                 295                 300

Lys Lys Met Ile Cys Cys Phe Ser Gln Glu Asn Pro Glu Arg Arg Pro
305                 310                 315                 320

Ser Arg Ile Pro Ser Thr Val Leu Ser Arg Ser Asp Thr Gly Ser Gln
                325                 330                 335

Tyr Ile Glu Asp Ser Ile Ser Gln Gly Ala Val Cys Asn Lys Ser Thr
            340                 345                 350

Ser

<210> SEQ ID NO 12
<211> LENGTH: 400
<212> TYPE: PRT
<213> ORGANISM: Rattus norvegicus
<220> FEATURE:
<223> OTHER INFORMATION: rat endothelial differentiation G-protein
      coupled receptor (GPCR) 8 (EDG8)

<400> SEQUENCE: 12

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
                20                  25                  30

Gly Ala Gly Leu Arg Ala Asp Ala Ala Val Cys Leu Ala Val Cys Ala
            35                  40                  45

Phe Ile Val Leu Glu Asn Leu Ala Val Leu Leu Val Leu Gly Arg His
        50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Thr Asn Ile Leu Leu Ser
```

```
                    85                  90                  95
Gly Pro Leu Thr Leu Arg Leu Ser Pro Ala Leu Trp Phe Ala Arg Glu
                100                 105                 110

Gly Gly Val Phe Val Ala Leu Ala Ala Ser Val Leu Ser Leu Leu Ala
            115                 120                 125

Ile Ala Leu Glu Arg His Leu Thr Met Ala Arg Arg Gly Pro Ala Pro
        130                 135                 140

Ala Ala Ser Arg Ala Arg Thr Leu Ala Met Ala Val Ala Ala Trp Gly
145                 150                 155                 160

Leu Ser Leu Leu Leu Gly Leu Leu Pro Ala Leu Gly Trp Asn Cys Leu
                165                 170                 175

Gly Arg Leu Glu Ala Cys Ser Thr Val Leu Pro Leu Tyr Ala Lys Ala
                180                 185                 190

Tyr Val Leu Phe Cys Val Leu Ala Phe Leu Gly Ile Leu Ala Ala Ile
                195                 200                 205

Cys Ala Leu Tyr Ala Arg Ile Tyr Cys Gln Val Arg Ala Asn Ala Arg
        210                 215                 220

Arg Leu Arg Ala Gly Pro Gly Ser Arg Arg Ala Thr Ser Ser Ser Arg
225                 230                 235                 240

Ser Arg His Thr Pro Arg Ser Leu Ala Leu Leu Arg Thr Leu Ser Val
                245                 250                 255

Val Leu Leu Ala Phe Val Ala Cys Trp Gly Pro Leu Phe Leu Leu Leu
                260                 265                 270

Leu Leu Asp Val Ala Cys Pro Ala Arg Ala Cys Pro Val Leu Leu Gln
                275                 280                 285

Ala Asp Pro Phe Leu Gly Leu Ala Met Ala Asn Ser Leu Leu Asn Pro
        290                 295                 300

Ile Ile Tyr Thr Phe Thr Asn Arg Asp Leu Arg His Ala Leu Leu Arg
305                 310                 315                 320

Leu Leu Cys Cys Gly Arg Gly Pro Cys Asn Gln Asp Ser Ser Asn Ser
                325                 330                 335

Leu Gln Arg Ser Pro Ser Ala Val Gly Pro Ser Gly Gly Leu Arg
            340                 345                 350

Arg Cys Leu Pro Pro Thr Leu Asp Arg Ser Ser Ser Pro Ser Glu His
            355                 360                 365

Ser Cys Pro Gln Arg Asp Gly Met Asp Thr Ser Cys Ser Thr Gly Ser
        370                 375                 380

Pro Gly Ala Ala Thr Ala Asn Arg Thr Leu Val Pro Asp Ala Thr Asp
385                 390                 395                 400

<210> SEQ ID NO 13
<211> LENGTH: 341
<212> TYPE: PRT
<213> ORGANISM: Homo sapiens
<220> FEATURE:
<223> OTHER INFORMATION: mutant #1, C-terminally truncated variant of
      human endothelial differentiation G-protein
      coupled receptor (GPCR) 1 (EDG1)

<400> SEQUENCE: 13

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45
```

```
Ser Val Val Phe Ile Leu Ile Cys Cys Phe Ile Ile Leu Glu Asn Ile
        50                  55                  60

Phe Val Leu Leu Thr Ile Trp Lys Thr Lys Phe His Arg Pro Met
65                  70                  75                  80

Tyr Tyr Phe Ile Gly Asn Leu Ala Leu Ser Asp Leu Leu Ala Gly Val
                    85                  90                  95

Ala Tyr Thr Ala Asn Leu Leu Leu Ser Gly Ala Thr Thr Tyr Lys Leu
                100                 105                 110

Thr Pro Ala Gln Trp Phe Leu Arg Glu Gly Ser Met Phe Val Ala Leu
                115                 120                 125

Ser Ala Ser Val Phe Ser Leu Leu Ala Ile Ala Ile Glu Arg Tyr Ile
        130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                    165                 170                 175

Leu Pro Ile Met Gly Trp Asn Cys Ile Ser Ala Leu Ser Ser Cys Ser
                180                 185                 190

Thr Val Leu Pro Leu Tyr His Lys His Tyr Ile Leu Phe Cys Thr Thr
                195                 200                 205

Val Phe Thr Leu Leu Leu Ser Ile Val Ile Leu Tyr Cys Arg Ile
        210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                    245                 250                 255

Thr Val Ile Ile Val Leu Ser Val Phe Ile Ala Cys Trp Ala Pro Leu
                260                 265                 270

Phe Ile Leu Leu Leu Leu Asp Val Gly Cys Lys Val Lys Thr Cys Asp
                275                 280                 285

Ile Leu Phe Arg Ala Glu Tyr Phe Leu Val Leu Ala Val Leu Asn Ser
                290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                    325                 330                 335

Ala Gly Lys Phe Lys
                340

<210> SEQ ID NO 14
<211> LENGTH: 314
<212> TYPE: PRT
<213> ORGANISM: Homo sapiens
<220> FEATURE:
<223> OTHER INFORMATION: mutant #2, C-terminally truncated variant of
      human endothelial differentiation G-protein
      coupled receptor (GPCR) 1 (EDG1)

<400> SEQUENCE: 14

Met Gly Pro Thr Ser Val Pro Leu Val Lys Ala His Arg Ser Ser Val
1                   5                   10                  15

Ser Asp Tyr Val Asn Tyr Asp Ile Ile Val Arg His Tyr Asn Tyr Thr
                20                  25                  30

Gly Lys Leu Asn Ile Ser Ala Asp Lys Glu Asn Ser Ile Lys Leu Thr
            35                  40                  45
```

```
Ser Val Val Phe Ile Leu Ile Cys Cys Phe Ile Ile Leu Glu Asn Ile
 50                  55                  60

Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
                 85                  90                  95

Ala Tyr Thr Ala Asn Leu Leu Ser Gly Ala Thr Thr Tyr Lys Leu
                100                 105                 110

Thr Pro Ala Gln Trp Phe Leu Arg Glu Gly Ser Met Phe Val Ala Leu
            115                 120                 125

Ser Ala Ser Val Phe Ser Leu Leu Ala Ile Ala Ile Glu Arg Tyr Ile
130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
                195                 200                 205

Val Phe Thr Leu Leu Leu Leu Ser Ile Val Ile Leu Tyr Cys Arg Ile
210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Val Lys Thr Cys Asp
                275                 280                 285

Ile Leu Phe Arg Ala Glu Tyr Phe Leu Val Leu Ala Val Leu Asn Ser
            290                 295                 300

Gly Thr Asn Pro Ile Ile Tyr Thr Leu Thr
305                 310

<210> SEQ ID NO 15
<211> LENGTH: 346
<212> TYPE: PRT
<213> ORGANISM: Homo sapiens
<220> FEATURE:
<223> OTHER INFORMATION: mutant #3, C-terminally truncated variant of
      human endothelial differentiation G-protein
      coupled receptor (GPCR) 1 (EDG1)

<400> SEQUENCE: 15

Met Gly Pro Thr Ser Val Pro Leu Val Lys Ala His Arg Ser Ser Val
  1               5                  10                  15

Ser Asp Tyr Val Asn Tyr Asp Ile Ile Val Arg His Tyr Asn Tyr Thr
                 20                  25                  30

Gly Lys Pro Asn Ile Ser Ala Asp Lys Glu Asn Ser Ile Lys Leu Thr
             35                  40                  45

Ser Val Val Phe Ile Leu Ile Cys Cys Phe Ile Ile Leu Glu Asn Ile
 50                  55                  60

Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
```

-continued

|  |  |  |  |  | 85 |  |  |  | 90 |  |  |  | 95 |  |
|---|---|---|---|---|---|---|---|---|---|---|---|---|---|---|
| Ala | Tyr | Thr | Ala | Asn | Leu | Leu | Leu | Ser | Gly | Ala | Thr | Tyr | Lys | Leu |
|  |  |  | 100 |  |  |  |  | 105 |  |  |  | 110 |  |  |
| Thr | Pro | Ala | Gln | Trp | Phe | Leu | Arg | Glu | Gly | Ser | Met | Phe | Val | Ala | Leu |
|  |  |  | 115 |  |  |  |  | 120 |  |  |  | 125 |  |  |
| Ser | Ala | Ser | Val | Phe | Ser | Leu | Leu | Ala | Ile | Ala | Ile | Glu | Arg | Tyr | Ile |
|  |  |  | 130 |  |  |  |  | 135 |  |  |  | 140 |  |  |
| Thr | Met | Leu | Lys | Met | Lys | Leu | His | Asn | Gly | Ser | Asn | Asn | Phe | Arg | Leu |
| 145 |  |  |  |  | 150 |  |  |  | 155 |  |  |  | 160 |
| Phe | Leu | Leu | Ile | Ser | Ala | Cys | Trp | Val | Ile | Ser | Leu | Ile | Leu | Gly | Gly |
|  |  |  | 165 |  |  |  |  | 170 |  |  |  | 175 |  |  |
| Leu | Pro | Ile | Met | Gly | Trp | Asn | Cys | Ile | Ser | Ala | Leu | Ser | Ser | Cys | Ser |
|  |  |  | 180 |  |  |  |  | 185 |  |  |  | 190 |  |  |
| Thr | Val | Leu | Pro | Leu | Tyr | His | Lys | His | Tyr | Ile | Leu | Phe | Cys | Thr | Thr |
|  |  |  | 195 |  |  |  |  | 200 |  |  |  | 205 |  |  |
| Val | Phe | Thr | Leu | Leu | Leu | Leu | Ser | Ile | Val | Ile | Leu | Tyr | Cys | Arg | Ile |
|  |  |  | 210 |  |  |  |  | 215 |  |  |  | 220 |  |  |
| Tyr | Ser | Leu | Val | Arg | Thr | Arg | Ser | Arg | Arg | Leu | Thr | Phe | Arg | Lys | Asn |
| 225 |  |  |  |  | 230 |  |  |  | 235 |  |  |  | 240 |
| Ile | Ser | Lys | Ala | Ser | Arg | Ser | Ser | Glu | Lys | Ser | Leu | Ala | Leu | Leu | Arg |
|  |  |  | 245 |  |  |  |  | 250 |  |  |  | 255 |  |  |
| Thr | Val | Ile | Ile | Val | Leu | Ser | Val | Phe | Ile | Ala | Cys | Trp | Ala | Pro | Leu |
|  |  |  | 260 |  |  |  |  | 265 |  |  |  | 270 |  |  |
| Phe | Ile | Leu | Leu | Leu | Leu | Asp | Val | Gly | Cys | Lys | Val | Lys | Thr | Cys | Asp |
|  |  |  | 275 |  |  |  |  | 280 |  |  |  | 285 |  |  |
| Ile | Leu | Phe | Arg | Ala | Glu | Tyr | Phe | Leu | Val | Leu | Ala | Val | Leu | Asn | Ser |
|  |  |  | 290 |  |  |  |  | 295 |  |  |  | 300 |  |  |
| Gly | Thr | Asn | Pro | Ile | Ile | Tyr | Thr | Leu | Thr | Asn | Lys | Glu | Met | Arg | Arg |
| 305 |  |  |  |  | 310 |  |  |  | 315 |  |  |  | 320 |
| Ala | Phe | Ile | Arg | Ile | Met | Ser | Cys | Cys | Lys | Cys | Pro | Ser | Gly | Asp | Ser |
|  |  |  | 325 |  |  |  |  | 330 |  |  |  | 335 |  |  |
| Ala | Gly | Lys | Phe | Lys | Arg | Pro | Ile | Ile | Ala |
|  |  |  | 340 |  |  |  |  | 345 |  |